US009605317B2

(12) United States Patent
Cohen et al.

(10) Patent No.: US 9,605,317 B2
(45) Date of Patent: Mar. 28, 2017

(54) BIOMARKERS FOR ASSESSING PERIPHERAL NEUROPATHY RESPONSE TO CANCER TREATMENT

(75) Inventors: Nadine Cohen, Princeton, NJ (US); Reyna Favis, Phillipsburg, NJ (US); Qingqin Li, Flemington, NJ (US); Deborah Ricci, Ringoes, NJ (US); Yu Sun, Belle Mead, NJ (US); Helgi van de Velde, Retie (BE)

(73) Assignee: Janssen Pharmaceutica NV, Beerse (BE)

( * ) Notice: Subject to any disclaimer, the term of this patent is extended or adjusted under 35 U.S.C. 154(b) by 828 days.

(21) Appl. No.: 12/730,587

(22) Filed: Mar. 24, 2010

(65) Prior Publication Data

US 2010/0249065 A1 Sep. 30, 2010

Related U.S. Application Data

(60) Provisional application No. 61/162,848, filed on Mar. 24, 2009.

(51) Int. Cl.
*A61K 38/05* (2006.01)
*C12Q 1/68* (2006.01)

(52) U.S. Cl.
CPC ..... *C12Q 1/6886* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| 5,780,454 A | 7/1998 | Adams et al. |
| 6,083,903 A | 7/2000 | Adams et al. |
| 6,297,217 B1 | 10/2001 | Adams et al. |
| 6,465,433 B1 | 10/2002 | Adams et al. |
| 6,548,668 B2 | 4/2003 | Adams et al. |
| 6,617,317 B1 | 9/2003 | Adams et al. |
| 6,699,835 B2 | 3/2004 | Plamondon et al. |
| 6,713,446 B2 | 3/2004 | Gupta |
| 6,747,150 B2 | 6/2004 | Adams et al. |
| 6,958,319 B2 | 10/2005 | Gupta |
| 7,109,323 B2 | 9/2006 | Plamondon et al. |
| 7,119,080 B2 | 10/2006 | Adams et al. |
| 7,422,830 B2 | 9/2008 | Nam et al. |

FOREIGN PATENT DOCUMENTS

| WO | WO 2007/067263 A2 | 6/2007 |
| WO | 2008028687 A1 | 3/2008 |

OTHER PUBLICATIONS

Wang et al (BioMed Cent 7: 1-7, 2007).*
Breunis et al. (J. Immunother 31: 586-590, 2008).*
Badros et al. (Cancer 110: 1042-8, 2007).*
Yang et al, Ann Oncol 17: 813-817, 2006.*
Argyriou, et al., Sep. 1, 2008, Bortezomib-Induced Peripheral Neuropathy in Multiple Myeloma: A Comprehensive Review of the Literature, Blood, vol. 112, No. 5, pp. 1593-1599.
Badros, et al., 2007, Neurotoxicity of Bortezomib Therapy in Multiple Myeloma: A Single-Center Experience and Review of the Literature, Cancer, vol. 110, pp. 1042-1049.
Cata, et al., 2007, Quantitative Sensory Findings in Patients with Bortezomib-Induced Pain, The Journal of Pain, vol. 8, No. 4, pp. 296-306.
Corthals, et al., 2009, Genetic Associations with Bortezomib Mediated Neuropathy in Multiple Myeloma, Blood, vol. 114, No. 22, p. 713.
El-Cheikh, et al., 2008, Features and Risk Factors of Peripheral Neuropathy During Treatment with Bortezomib for Advanced Multiple Myeloma, Clinical Lymphona & Myeloma, vol. 8, No. 3, pp. 146-152.
Kuiper, et al., Dec. 5, 2009, Developing a SNP Classifier for Predicting Peripheral Neuropathy by Bortezomib in Multiple Myeloma Patients, Oral and Poster Abstracts, Poster Board I-822, pp. 715-716.
Landowski, et al., May 1, 2005, Mitochondrial-Mediated Disregulation of Ca2+ Is a Critical Determinant of Velcade (PS-341/Bortezomib) Cytotoxicity in Myeloma Cell Lines, Cancer Research, vol. 65, Issue 9, pp. 3828-3836.
Pei, et al., Jun. 1, 2004, Synergistic Induction of Oxidative Injury and Apoptosis in Human Multiple Myeloma Cells by the Proteasome Inhibitor Bortezomib and Histone Deacetylase Inhibitors, Clinical Cancer Research, 10, pp. 3839-3852.
Ricci, et al., 2009, Pharmacogenomic (PGx) Analysis of Bortezomib-Associated Peripheral Neuropathy in the Phase 3 Vista Trial of Bortezomib Plus Melphalan-Prednisone Versus Melphalan-Prednisone in Multiple Myeloma, Blood, vol. 114, No. 22, Abstract 3875.
Richardson, et al., Jul. 1, 2006, Frequency, Characteristics, and Reversibility of Peripheral Neuropathy During Treatment of Advanced Multiple Myeloma with Bortezomib, Journal of Clinical Oncology, vol. 24, No. 19, pp. 3113-3120.
Saxena, et al., 2006, Comprehensive Association Testing of Common Mitochondrial DNA Variation in Metabolic Disease, The American Journal of Human Genetics, vol. 79, pp. 54-61.
Windebank, et al., 2008, Chemotherapy-Induced Neuropathy, Journal of the Peripheral Nervous System, vol. 13, pp. 27-46.
Lichter et al, "Sequence Analysis of β-subunit genes of the 20S proteasome in patients with relasped multiple myeloma treated with bortezomib or dexamethasone.", Blood, 2012, pp. 4513-4516, vol. 120.
Lichter et al, Supplemental Material, 2012.
Lichter, D. I., "Sequence analysis of the 20S proteasome β-subunit genes in tumor tissue and cell lines.", *A Thesis in the Field of Biotechnology for the Degree of Master of Liberal Arts in Extension Studies.*, Nov. 2008, Harvard University.

(Continued)

*Primary Examiner* — Daniel E Kolker
*Assistant Examiner* — Aditi Dutt

(57) ABSTRACT

The present invention provides methods for identifying patients at increased risk of developing an adverse neurological event in response to a cancer treatment. Methods also include modifying the treatment regimen of said patent dependent on the presence or absence of biomarkers in the patient.

7 Claims, No Drawings

(56) References Cited

OTHER PUBLICATIONS

Lichter, D. I., "Sequence analysis of the 20S proteasome β-subunit genes in tumor tissue and cell lines.", *A Thesis in the Field of Biotechnology for the Degree of Master of Liberal Arts in Extension Studies.*, Nov. 2008, Harvard University; Bibliographical information, downloaded from internet Dec. 16, 2013.
Lunetta, K.L., "Genetic Association Studies.", *CirculationAHA*, 2008, pp. 96-101, vol. 118.
Perry et al., "Interrogating Type 2 Diabetes Genome-Wide Association Data Using a Biological Pathway-Based Approach.", *Diabetes*, Jun. 2009, pp. 1463-1467, vol. 58.
Supplemental Tables, Perry et al., "Interrogating Type 2 Diabetes Genome-Wide Association Data Using a Biological Pathway-Based Approach.", *Diabetes*, Jun. 2009, pp. 1463-1467, vol. 58.

\* cited by examiner

BIOMARKERS FOR ASSESSING PERIPHERAL NEUROPATHY RESPONSE TO CANCER TREATMENT

CROSS REFERENCE TO RELATED APPLICATION

This application claims priority to provisional application Ser. No. 61/162,848, filed Mar. 24, 2009.

FIELD OF THE INVENTION

The present invention relates generally to the field of pharmacogenomics, and more specifically to the pharmacogenomic analysis of peripheral neuropathy candidate genes.

BACKGROUND OF THE INVENTION

Treatment with cancer drugs such as bortezomib has been associated with adverse events (AE) such as peripheral neuropathy (PN). Bortezomib-induced peripheral neuropathy typically occurs within the first courses of treatment with bortezomib and generally reaches a plateau at cycle 5 (Windebank & Grisold (2008) J. Peripher. Nerv. Syst. 13:27-46). Primarily, a small fiber and painful, axonal, sensory distal neuropathy is produced. The associated pain has a mean rating of 7.8 (on scale of 0 for no pain and 10 for worst imaginable pain) (Cata et al. (2007) J. Pain 8:296-306).

Bortezomib-induced pain is associated with three major fiber types (Aβ, Aδ and C caliber primary afferent fibers) in sensory nerves. An electrophysiologic nerve conduction study shows low amplitude of sensory action potential (distal, sensory, axonal neuropathy) (Richardson et al. (2006) J. Clin. Oncol 24:3113-3120). Conduction studies are consistent with primary or secondary demyelination process due to primary myelin-Schwann cell damage or degeneration of fast-conducting fibers (demyelination neuropathy noted in ulnar nerves) (Badros et al. (2007) Cancer 110:1042-1049).

Mitochondrial and endoplasmic reticulum damage in addition to other factors may play a key role in bortezomib-induced peripheral neuropathy development in humans. Bortezomib activates the mitochondrial-based apoptotic pathway (Pei et al. (2004) Clin. Cancer Res. 10:3839-3852). Bortezomib may also play a role in disregulation of neurotrophins as evidenced by inhibition of NF-kB activation which has been shown to block transcription of nerve growth factor (NGF) mediated neuron survival (NGF induces differentiation and survival of sensory nerve cells) (Landowski et al. (2005) Cancer Res. 65:3828-3836).

It has been observed that bortezomib-induced peripheral neuropathy is predominately sensory. Patients with pre-existing signs of peripheral neuropathy may experience worsening peripheral neuropathy during treatment. Dose reduction resulted in improvement or resolution of peripheral neuropathy in 51% of patients with >Grade 2 PN in a phase 2 multiple myeloma study. Dose discontinuation resulted in improvement or resolution of peripheral neuropathy in 73% of patients discontinuing due to Grade 2 peripheral neuropathy or who had >Grade 3 peripheral neuropathy in a phase 2 multiple myeloma study.

Adverse responses to drugs constitute a major medical problem. To the extent that some of these adverse events are due to genetically encoded biochemical diversity among patients in pathways that effect drug action, the identification of variances that are predictive of such effects will allow for more effective and safer drug use. Thus, there is a need for biomarkers useful for identifying patients most at risk for bortezomib-induced neuropathy.

SUMMARY OF THE INVENTION

The invention provides a method for identifying whether a patient is at increased risk for developing an adverse neurological event in respond to a cancer treatment, comprising: determining whether or not said patient possesses one or more biomarkers for said increased risk, wherein the presence of said biomarker indicates an increased risk for said adverse neurological event. The presence of biomarkers may be determined by obtaining a biological sample from said patient, and performing genotyping analysis on the sample. In certain embodiments the adverse neurological event is peripheral neuropathy, peripheral sensory neuropahty or neuralgia. The cancer treatment may comprise administration of a proteosome inhibitor, such as bortezomib. The biomarkers may be one or more of rs4553808; rs1474642; rs12568757; rs11974610; or rs1261134.

Also provided are diagnostic kits for identifying patients likely to develop an adverse neurologic event in response to treatment for cancer and methods for treating cancer or individualizing a cancer treatment regimen.

DETAILED DESCRIPTION OF THE INVENTION

The present invention describes the identification of peripheral neuropathy candidate genes that serve as useful molecular tools for predicting an adverse response to cancer drugs. Specifically, the present invention is directed to methods of identifying whether or not a patient is at increased risk of suffering an adverse neurologic event in response to treatment with proteosome inhibitors such as bortezomib.

The present invention involves the identification of genetic variances also referred to herein as "variants", "markers" and/or "biomarkers", that correlate with an increased risk of adverse neurological response to a cancer treatment. The association of patient response to drug treatment with these markers can open up new opportunities for drug development or distinguish a drug's indication among other treatment choices because of higher confidence in the safety and/or efficacy.

The cancer treatment may include administration of a single drug or treatment, or administration of more than one drug or treatment. In certain embodiments, the cancer treatment comprises administering a proteasome inhibitor to a patient. Proteosome inhibitors include bortezomib, and/or compounds having structure similar to that of bortezomib. Proteasome inhibitors having structure similar to bortezomib include those compounds disclosed in U.S. Pat. Nos. 7,119,080; 6,747,150; 6,617,317; 6,548,668; 6,465,433; 6,297,217; 6,083,903; 5,780,454; 7,422,830; 7,109,323; 6,958,319; 6,713,446; and 6,699,835.

The adverse neurological event may be peripheral sensory neuropathy, neuralgia, peripheral neuropathy (NEC). The methods of the invention may identify increased risk of only one neurological event, or increased risk of more than one neurological event.

The increased risk may be any increase over the average risk, including increased risk of developing adverse neurological event in response to any level of treatment, increased risk of developing an adverse neurological event earlier in treatment, or increased risk of developing an adverse event in response to higher treatment doses. The increased risk may be dose-dependent or dose-independent.

The presence or absence of a biomarker may be assessed by obtaining a biological sample from a patient and determining whether said biological sample contains the biomarker. A "biological sample" as used herein refers to a sample containing or consisting of cells or tissue matter, such as cells or biological fluids isolated from a subject. Examples of biological samples include, for example, sputum, blood, blood cells (e.g., white blood cells), amniotic fluid, plasma, serum, semen, saliva, bone marrow, tissue or fine-needle biopsy samples, urine, peritoneal fluid, pleural fluid, and cell cultures. Biological samples may also include sections of tissues such as frozen sections taken for histological purposes. A test biological sample is the biological sample that has been the object of analysis, monitoring, or observation. A control biological sample can be either a positive or a negative control for the test biological sample. Often, the control biological sample contains the same type of tissues, cells and/or biological fluids of interest as that of the test biological sample. In particular embodiments, the biological sample is a "clinical sample," which is a sample derived from a human patient.

As used herein, the terms "comprising", "containing", "having" and "including" are used in their open, non-limiting sense.

"Genotyping" refers to the process of determining the genotype of an individual by the use of biological assays. Current methods of doing this include PCR, DNA sequencing, antisense oligonucleotide probes, and hybridization to DNA microarrays or beads. The technology is employed in clinical research for the investigation of disease-associated and response-associated genes. Due to current technological limitations, almost all genotyping is partial. That is, only a small fraction of an individual's genotype is determined.

A "single nucleotide polymorphism" (SNP, pronounced snip) is a DNA sequence variation occurring when a single nucleotide—A, T, C, or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case it is said that there are two alleles: C and T. Almost all common SNPs have only two alleles.

Within a population, SNPs can be assigned a minor allele frequency—the lowest allele frequency at a locus that is observed in a particular population. This is simply the lesser of the two allele frequencies for single nucleotide polymorphisms. There are variations between human populations, so a SNP allele that is common in one geographical or ethnic group may be much rarer in another.

Biomarkers according to this invention which correlate with increased risk of adverse neurological events include rs4553808; rs1474642; rs12568757; rs11974610; and rs1261134.

This application concerns the field of mammalian therapeutics and the selection of therapeutic regimens utilizing host genetic information, including gene sequence variances within the human genome in human populations. The application further concerns methods for identification of DNA sequence variations likely to affect treatment response.

The present invention is concerned generally with the field of identifying an appropriate treatment regimen for a disease based upon genotype in mammals, particularly in humans. It is further concerned with the genetic basis of inter-patient variation in response to therapy, including drug therapy. Specifically, this invention describes the identification of gene sequence variances useful in the field of therapeutics for optimizing efficacy and safety of drug therapy. These variances may be useful in guiding the optimal use of already approved compounds such as bortezomib. DNA sequence variances in candidate genes (i.e., genes that may plausibly affect the action of a drug) are tested in clinical trials, leading to the establishment of diagnostic tests useful for improving the development of new pharmaceutical products and/or the more effective use of existing pharmaceutical products. The identification of genetic variances and the determination of their utility in the selection of optimal therapy for specific patients are also described. In general, the invention relates to the identification of patient population subsets that respond to drug therapy with either therapeutic benefit or side effects (i.e., symptomatology prompting concern about safety or other unwanted signs or symptoms) such as peripheral neuropathy.

The identification of gene sequence variances in genes that may be involved in drug action are useful for determining whether genetic variances account for variable drug efficacy and safety and for determining whether a given drug or other therapy may be safe and effective in an individual patient. Provided in this invention are identifications of genes and sequence variances which can be useful in connection with predicting differences in response to treatment. A target gene and variances are useful, for example, in pharmacogenetic association studies and diagnostic tests to improve the use of certain drugs or other therapies.

In embodiments of this invention, the variance or variant form or forms of a gene is/are associated with a specific response to a drug. The frequency of a specific variance or variant form of the gene may correspond to the frequency of an efficacious response to administration of a drug. Alternatively, the frequency of a specific variance or variant form of the gene may correspond to the frequency of an adverse event resulting from administration of a drug. Alternatively the frequency of a specific variance or variant form of a gene may not correspond closely with the frequency of a beneficial or adverse response, yet the variance may still be useful for identifying a patient subset with high response or toxicity incidence because the variance may account for only a fraction of the patients with high response or toxicity. In such a case the preferred course of action is identification of a second or third or additional variances that permit identification of the patient groups not usefully identified by the first variance.

Also in other embodiments, the method of selecting a treatment includes excluding or eliminating a treatment, where the presence or absence of the at least one variance is indicative that the treatment will be ineffective or contraindicated. In other preferred embodiments, in cases in which undesirable side-effects may occur or are expected to occur from a particular therapeutic treatment, the selection of a method of treatment can include identifying both a first and second treatment, where the first treatment is effective to treat the disease or condition, and the second treatment reduces a deleterious effect of the first treatment.

The phrase "eliminating a treatment" or "excluding a treatment" refers to removing a possible treatment from consideration, e.g., for use with a particular patient based on the presence or absence of a particular variance(s) in one or more genes in cells of that patient, or to stopping the administration of a treatment.

Usually, the treatment will involve the administration of a compound preferentially active or safe in patients with a form or forms of a gene, where the gene is one identified herein. The administration may involve a combination of compounds. Thus, in preferred embodiments, the method involves identifying such an active compound or combination of compounds, where the compound or combination is less active or is less safe or both when administered to a patient having a different form of the gene.

Also in preferred embodiments, the method of selecting a treatment involves selecting a method of administration of a compound, combination of compounds, or pharmaceutical composition, for example, selecting a suitable dosage level and/or frequency of administration, and/or mode of administration. The method of administration can be selected to provide better, preferably maximum therapeutic benefit. In this context, "maximum" refers to an approximate local maximum based on the parameters being considered, not an absolute maximum.

Also in this context, a "suitable dosage level" refers to a dosage level that provides a therapeutically reasonable balance between pharmacological effectiveness and deleterious effects. Often this dosage level is related to the peak or average serum levels resulting from administration of a drug at the particular dosage level.

Similarly, a "frequency of administration" refers to how often in a specified time period a treatment is administered, e.g., once, twice, or three times per day, every other day, once per week, etc. For a drug or drugs, the frequency of administration is generally selected to achieve a pharmacologically effective average or peak serum level without excessive deleterious effects (and preferably while still being able to have reasonable patient compliance for self-administered drugs). Thus, it is desirable to maintain the serum level of the drug within a therapeutic window of concentrations for the greatest percentage of time possible without such deleterious effects as would cause a prudent physician to reduce the frequency of administration for a particular dosage level.

The term "genotype" refers to the alleles present in DNA from a subject or patient, where an allele can be defined by the particular nucleotide(s) present in a nucleic acid sequence at a particular site(s). Often a genotype is the nucleotide(s) present at a single polymorphic site known to vary in the human population.

The detection of the presence or absence of at least one variance involves contacting a nucleic acid sequence corresponding to one of the genes identified herein or a product of such a gene with a probe. The probe is able to distinguish a particular form of the gene or gene product or the presence or a particular variance or variances, e.g., by differential binding or hybridization.

The terms "variant form of a gene", "form of a gene", or "allele" refer to one specific form of a gene in a population, the specific form differing from other forms of the same gene in the sequence of at least one, and frequently more than one, variant sites within the sequence of the gene. The sequences at these variant sites that differ between different alleles of the gene are termed "gene sequence variances" or "variances" or "variants". The term "alternative form" refers to an allele that can be distinguished from other alleles by having distinct variances at least one, and frequently more than one, variant sites within the gene sequence.

Variances occur in the human genome at approximately one in every 500-1,000 bases within the human genome when two alleles are compared. When multiple alleles from unrelated individuals are compared the density of variant sites increases as different individuals, when compared to a reference sequence, will often have sequence variances at different sites. At most variant sites there are only two alternative nucleotides involving the substitution of one base for another or the insertion/deletion of one or more nucleotides. Within a gene there may be several variant sites. Variant forms of the gene or alternative alleles can be distinguished by the presence of alternative variances at a single variant site, or a combination of several different variances at different sites (haplotypes).

The "identification" of genetic variances or variant forms of a gene involves the discovery of variances that are present in a population. The identification of variances is required for development of a diagnostic test to determine whether a patient has a variant form of a gene that is known to be associated with a disease, condition, or predisposition or with the efficacy or safety of the drug. Identification of previously undiscovered genetic variances is distinct from the process of "determining" the status of known variances by a diagnostic test (often referred to as genotyping). The present invention provides exemplary variances in genes listed in the gene tables included and described herein.

In the context of this invention, the term "haplotype" refers to a cis arrangement of two or more polymorphic nucleotides, i.e., variances, on a particular chromosome, e.g., in a particular gene. The haplotype preserves information about the phase of the polymorphic nucleotides—that is, which set of variances were inherited from one parent, and which from the other. A genotyping test does not provide information about phase. For example, an individual heterozygous at nucleotide 25 of a gene (both A and C are present) and also at nucleotide 100 (both G and T are present) could have haplotypes 25A-100G and 25C-100T, or alternatively 25A-100T and 25C-100G. Only a haplotyping test can discriminate these two cases definitively.

The terms "variances", "variants" and "polymorphisms", as used herein, may also refer to a set of variances, haplotypes or a mixture of the two, unless otherwise indicated. Further, the term variance, variant or polymorphism (singular), as used herein, also encompasses a haplotype unless otherwise indicated. This usage is intended to minimize the need for cumbersome phrases such as: " . . . measure correlation between drug response and a variance, variances, haplotype, haplotypes or a combination of variances and haplotypes . . . ", throughout the application. Similarly, the term "genotype", as used herein, means a procedure for determining the status of one or more variances in a gene, including a set of variances comprising a haplotype. Thus phrases such as " . . . genotype a patient . . . " refer to determining the status of one or more variances, including a set of variances for which phase is known (i.e. a haplotype).

In preferred embodiments of this invention, the frequency of the variance or variant form of the gene in a population is known. Measures of frequency known in the art include "allele frequency", namely the fraction of genes in a population that have one specific variance or set of variances. The allele frequencies for any gene should sum to 1. Another measure of frequency known in the art is the "heterozygote frequency" namely, the fraction of individuals in a population who carry two alleles, or two forms of a particular variance or variant form of a gene, one inherited from each parent. Alternatively, the number of individuals who are homozygous for a particular form of a gene may be a useful measure. The relationship between allele frequency, heterozygote frequency, and homozygote frequency is described for many genes by the Hardy-Weinberg equation, which provides the relationship between allele frequency, heterozygote frequency and homozygote frequency in a freely breeding population at equilibrium. Most human variances are substantially in Hardy-Weinberg equilibrium.

"Population" refers to a defined group of individuals or a group of individuals with a particular disease or condition or individuals that may be treated with a specific drug identified by, but not limited to geographic, ethnic, race, gender, and/or cultural indices. In most cases a population will preferably encompass at least ten thousand, one hundred thousand, one million, ten million, or more individuals, with the larger numbers being more preferable. In embodiments of this invention, the allele frequency, heterozygote frequency, or homozygote frequency of a specific variance or variant form of a gene is known. In preferred embodiments of this invention, the frequency of one or more variances that may predict response to a treatment is determined in one or more populations using a diagnostic test.

It should be emphasized that it is currently not generally practical to study an entire population to establish the association between a specific disease or condition or response to a treatment and a specific variance or variant form of a gene. Such studies are preferably performed in controlled clinical trials using a limited number of patients that are considered to be representative of the population with the disease. Since drug development programs are generally targeted at the largest possible population, the study population will generally consist of men and women, as well as members of various racial and ethnic groups, depending on where the clinical trial is being performed. This is important to establish the efficacy of the treatment in all segments of the population.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the presence of one or more sequence variances or alleles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as an improvement of symptoms, a cure, a reduction in disease load, reduction in tumor mass or cell numbers, extension of life, improvement in quality of life, or other effect generally recognized as positive by medical doctors familiar with treating the particular type of disease or condition.

Effectiveness is measured in a particular population. In conventional drug development the population is generally every subject who meets the enrollment criteria (i.e. has the particular form of the disease or condition being treated). It is an aspect of the present invention that segmentation of a study population by genetic criteria can provide the basis for identifying a subpopulation in which administration of a drug such as VELCADE™ may likely induce peripheral neuropathy.

The term "deleterious effects" refers to physical effects in a patient caused by administration of a treatment which are regarded as medically undesirable. Thus, for example, deleterious effects can include a wide spectrum of toxic effects injurious to health such as death of normally functioning cells when only death of diseased cells is desired, nausea, fever, inability to retain food, dehydration, damage to critical organs such as arrythmias, renal tubular necrosis, fatty liver, or pulmonary fibrosis leading to coronary, renal, hepatic, or pulmonary insufficiency among many others. In this regard, the term "contra-indicated" means that a treatment results in deleterious effects such that a prudent medical doctor treating such a patient would regard the treatment as unsuitable for administration. Major factors in such a determination can include, for example, availability and relative advantages of alternative treatments, consequences of non-treatment, and permanency of deleterious effects of the treatment.

It is recognized that many treatment methods, e.g., administration of certain compounds or combinations of compounds, may produce side-effects or other deleterious effects in patients. Such effects can limit or even preclude use of the treatment method in particular patients, or may even result in irreversible injury, dysfunction, or death of the patient. Thus, in certain embodiments, the variance information is used to select both a first method of treatment and a second method of treatment. Usually the first treatment is a primary treatment that provides a physiological effect directed against the disease or condition or its symptoms. The second method is directed to reducing or eliminating one or more deleterious effects of the first treatment, e.g., to reduce a general toxicity or to reduce a side effect of the primary treatment. Thus, for example, the second method can be used to allow use of a greater dose or duration of the first treatment, or to allow use of the first treatment in patients for whom the first treatment would not be tolerated or would be contra-indicated in the absence of a second method to reduce deleterious effects or to potentiate the effectiveness of the first treatment.

Similar to the above aspect, in an embodiment at least one method of treatment involves the administration of a compound effective in at least some patients with a disease or condition; the presence or absence of the at least one variance is indicative that the treatment will be effective in the patient; and/or the presence or absence of the at least one variance is indicative that the treatment will be ineffective or contra-indicated in the patient; and/or the treatment is a first treatment and the presence or absence of the at least one variance is indicative that a second treatment will be beneficial to reduce a deleterious effect of or potentiate the effectiveness of the first treatment; and/or the at least one treatment is a plurality of methods of treatment. For a plurality of treatments, preferably the selecting involves determining whether any of the methods of treatment will be more effective than at least one other of the plurality of methods of treatment.

In another aspect, the invention provides a method for selecting a patient for administration of a method of treatment for a disease or condition, or of selecting a patient for a method of administration of a treatment, by comparing the presence or absence of at least one variance in a gene as identified above in cells of a patient, with a list of variances in the gene, where the presence or absence of the at least one variance is indicative that the treatment or method of administration will be effective in the patient. If the at least one variance is present in the patient's cells, then the patient is selected for consideration of alternative treatment.

In another aspect, the invention provides a method for identifying a subset of patients with enhanced or diminished response or tolerance to a treatment method where the treatment is for a disease or condition in the patient. The method involves correlating one or more variances in one or more genes as identified in aspects above in a plurality of patients with response to a treatment method. The correlation may be performed by determining one or more variances in one or more genes in the plurality of patients and correlating the presence or absence of each of the variances (alone or in various combinations) with the patient's response to treatment and in particular to the development of peripheral neuropathy. The response should be statistically significant. A positive correlation between the presence of one or more variances and a response to treatment as demonstrated by evidence of peripheral neuropathy is indicative that the treatment is particularly ineffective in the group of patients having those variances. Such information is useful, for example, for selecting or de-selecting patients for a particular treatment or method of administration of a treatment, or for demonstrating that a group of patients exists for which the treatment or method of treatment would be particularly beneficial or contra-indicated.

In preferred embodiments, the correlation of patient responses to therapy according to patient genotype is carried out employing clinical trial data, e.g., as described herein according to any of the variations described.

A major goal of research is to identify markers that accurately predict a given patient's response to drugs in the clinic; such individualized assessment may greatly facilitate personalized treatment. An approach of this nature is particularly needed in cancer treatment and therapy, where commonly used drugs are ineffective in many patients, and side effects are frequent. The ability to predict drug sensitivity in patients is particularly challenging because drug responses reflect both the properties intrinsic to the target cells and also a host's metabolic properties.

All publications cited herein are hereby incorporated by reference. Unless defined otherwise, all technical and scientific terms used herein have the same meaning as commonly understood to one of ordinary skill in the art to which this invention pertains.

Example 1

A randomized, open-label, multicenter study was conducted, consisting of 3 Phases: a Pre-randomization (Screening) Phase, an Open-label Treatment Phase, and a Post-treatment Phase. Approximately 680 subjects with previously untreated multiple myeloma were randomly assigned to one of two treatment groups and were stratified according to baseline β2-microglobulin, baseline albumin levels and region (North America, Europe, other). Subjects received either VELCADE™/Melphalan/Prednisone (VMP) (Treatment Group A) or Melphalan/Prednisone (MP) (Treatment Group B). Subjects in Treatment Group A received VELCADE™ 1.3 mg/m² (twice weekly [Weeks 1, 2, 4, and 5] for four 6-week cycles [8 doses per cycle] followed by once weekly [Weeks 1, 2, 4, and 5] for five 6-week cycles [4 doses per cycle]) in combination with melphalan 9 mg/m² and prednisone 60 mg/m² (once daily on Days 1 to 4 of each 6-week cycle). Subjects in Treatment Group B received 9 cycles of melphalan 9 mg/m² and prednisone 60 mg/m² once daily on Days 1 to 4 of each 6-week cycle. For both groups, treatment continued for a maximum of 9 cycles (54 weeks) and subjects were discontinued if disease progression or an unacceptable treatment-related toxicity occurred, or if a subject withdrew consent.

DNA samples from study subjects were plated and normalized to a concentration of ≥50 ng/ul using a liquid handling robot. The DNA plates were then transferred to Illumina for genotyping analysis using the GoldenGate platform, which relies on primer extension. One blinded control was included on each plate. The controls consisted of duplicated samples and Coriell DNA (Coriell Institute for Medical Research, 408 Haddon Avenue, Camden, N.J.) samples that were used to generate HapMap data (to verify genotyping accuracy through comparisons with publicly available genotype data for these samples).

The candidate genes included with examples have previous associations linked to hereditary neuropathy, peripheral neuropathy, energy production and fast axonal transport, nociception and pain transmission, neurogenesis and neuroprotection. The candidates that were genotyped in the examples include: ACCN2, ACE, ACTB, ACTG1, ACTR1A, ACTR1B, ADORA2A, ADRA2B, AGT, AGTR1, AKR1B1, AKT1, AKT2, APC, ARP11, AXIN1, BMF, CACNA1A, CACNA1B, CAPZA1, CAPZA2, CAPZA3, CAPZB, CD86, COMT, CTLA4, CTNNB1, CTSS, CYP3A4, CYP3A5, DCTN1, DCTN2, DCTN3, DCTN4, DCTN6, DNCL1, DNCL2A, DNM2, DVL1, DVL2, DVL3, DYNC1H1, DYNC1I1, DYNC1I2, DYNC1LI1, DYNC1LI2, DYNC2H1, DYNC2LI1, DYNLL2, DYNLRB2, ECGF1, EGR2, FGD4, FIG4, GARS, GCH1, GDAP1, GJB1, GJB2, GJB3, GJE1, GLRA3, GLS2, GLUL, GSK3A, GSK3B, HAP1, HSN2, HSPB1, HSPB8, HTR1B, IKBKAP, IL6, KIF1A, KIF1B, KIF3A, KIF3B, KIFSA, KIFSB, KIFSC, LITAF, LMNA, MAPK1, MAPK10, MAPK11, MAPK12, MAPK13, MAPK14, MAPK3, MAPK4, MAPK6, MAPK7, MAPK8, MAPK9, MC1R, MFN2, Mitochondrial genome, MPZ, MTMR2, NDRG1, NEFL, NFE2L2, NGFB, NPY, NR112, NTRK1, OPRD1, OPRK1, OPRL1, OPRM1, PLP1, PMP22, PNOC, POLG, POLG2, PON1, PRPS1, PRX, PSMB1, PSMB10, PSMB2, PSMB3, PSMB4, PSMB5, PSMB6, PSMB7, PSMB8, PSMB9, PTGER1, PTGER2, PTGER3, PTGER4, PTGS1, PTGS2, SBF2, SCN3A, SCN9A, SH3TC2, SLC12A6, SPTBN1, SPTBN2, SPTBN4, SPTBN5, SPTLC1, SURF1, TCF1, TCF4, TH, TNF, TRAK2, TRPV1, TRPV4, TTR, VIP, WNT1, WNT10A, WNT10B, WNT11, WNT16, WNT2, WNT2B, WNT3, WNT3A, WNT4, WNTSA, WNTSB, WNT6, WNT7A, WNT8A, WNT8B, WNT9A, WNT9B and YARS.

Included in the analysis are the 368 subjects who met all of the following criteria: consented to DNA analysis; had usable genotype data for SNPs listed in Appendix 1; had Adverse Event related clinical data before treatment and after at least one cycle of VELCADE™ treatment (including those having neurological events and those completing treatment with no neurological event). These 368 subjects included: Treatment Group A (154 Caucasian, 2 black, 10 Asian); Treatment Group B (168 Caucasian, 4 black, 12 Asian), and 18 were not treated.

The primary adverse event endpoints are the treatment-emergent peripheral neuropathies caused by VELCADE™, including peripheral neuropathy NEC, peripheral sensory neuropathy, and neuralgia. For each specific peripheral neuropathy endpoint, the null hypothesis was that none of the successfully genotyped SNPs is associated with this specific treatment-emergent peripheral neuropathy. Each successfully genotyped SNP is tested to see whether there is a difference in the distribution of the genotypes of this SNP between patients with and without this specific VELCADE™ treatment-emergent peripheral neuropathy. The test result is subsequently adjusted by total number of successfully genotyped SNPs to correct multiplicity.

The secondary adverse event endpoints are the time to the first onset of treatment-emergent peripheral neuropathy caused by VELCADE™, including time to onset of any peripheral neuropathy, time to onset of grade≥2 peripheral neuropathy, and time to onset of grade≥3 peripheral neuropathy. For each specific time to onset endpoint, the null hypothesis is that none of the successfully genotyped SNPs is associated with the time to onset of this specific treatment-emergent peripheral neuropathy. For each successfully genotyped SNP, the patients are stratified according to the genotype of this SNP and tested to see whether there is a difference in the probability of onset of treatment-emergent peripheral neuropathy at any time point between patients of different genotypes. The test result is subsequently adjusted by total number of successfully genotyped SNPs to correct multiplicity. Some subjects have multiple incidences of peripheral neuropathy: i.e., a resolved AE followed by one or more re-occurred events. In the case of multiple events in the same patient, the time to first neuropathy for the analysis of 'neuropathy of any grade' and the time to neuropathy of a particular grade was considered the first day this particular grade is reported.

A series of quality control (QC) steps were conducted to assure the genotype data quality used in the analysis. The genotype data quality was assessed using internal control (duplicated) samples. Seven subjects from this study were genotyped twice. The concordance rate between duplicate samples was 100%. The duplicated sample data from this study were handled in the following way. Data was merged together by the following rules: 1) consistent genotype calls were kept. 2) If one sample had a genotype call while the other sample had a missing value (NA), the merged data was assigned the called genotype. 3) If both samples had a missing value, the merged data had a missing value. 4) If both samples had genotype calls and they are inconsistent with each other, the merged data were assigned missing values.

Genotype data of a Coriell DNA sample that was used to generate HapMap data, was compared against publicly available genotype data to verify genotyping accuracy. The Hapmap CEU subject NA12043 was genotyped as the quality control (ID: GS0034314-DNAH11_J369, CEPH1346-11). Of the 1927 non-mtSNPs successfully genotyped, 1921 of them were also genotyped in the Hapmap project. The concordance rate between these samples was 98.23%.

Samples with genotype call rates less than 0.9, i.e. more than 10% missing genotype data, were excluded from subsequent analysis. All genotyped samples had a call rate greater than 95%. Therefore, no samples were excluded due to more than 10% missing data. Three subject samples were not successfully genotyped after multiple attempts.

Sixty-four tagging SNPs of the human mitochondrial genome were also included in this analysis. The 64 tagging SNPs were selected based on the alignment of 928 publicly available European mitochondrial genome sequences to capture 144 common mitochondrial SNPs (mtSNPs) with MAF greater than 1% and 9 haplogroups (Saxena, R., etc. (2006) "Comprehensive association testing of common mitochondrial DNA variation in metabolic disease", *American Journal of Human Genetics* 79: 54-61).

Pair-wise correlation between genotypes of samples were calculated to identify questionable samples. If two subjects had identical genotype yet inconsistent phenotype data, both subjects were excluded from subsequent analysis. Heterozygosity of X-chromosome SNPs were calculated to identify gender discrepancies with the demographic data. Three subjects had discrepancies under gender control loci analysis and were excluded from the analysis. One additional subject was identified by PLINK to have heterozygous haploid genotypes on an X chromosome SNP (rs12116382), indicating a potential gender error. This subject was excluded from subsequent analysis.

After the quality control measures and filtering by race, one hundred thirty nine VELCADE™ treated samples were included in the analysis.

Example 2

A randomized, open-label, multicenter study was conducted that compared vincristine/adriamycin/dexamethasone (VAD) and VELCADE™/Dexamethasone as induction treatment prior to autologous hematopoietic stem cell transplantation (AHSCT) in patients up to (and including) the age of 65 with newly diagnosed multiple myeloma. Approximately 480 patients were included in this study. Subjects were randomized at diagnosis into one of 4 induction treatment arms:

A1 VAD (4 cycles)
A2 VAD (4 cycles) followed by Dexamethasone/cyclophosphomide/etoposide/cis-Platinum (DCEP) (2 cycles)
B1 VELCADE+dexamethasone (4 cycles)
B2 VELCADE+dexamethasone (4 cycles) followed by DCEP (2 cycles)

Randomization was stratified based on the initial β2 microglobulin level (> or ≤3 mg/l) and the presence of chromosome 13 abnormalities identified by fluorescence in situ hybridization (FISH) analysis. After induction treatment (Arms A1 and B1) or after consolidation treatment (Arms A2 and B2) all of the patients underwent AHSCT.

470 samples were sent to Illumina for genotyping on 2016 SNPs in 172 non-mitochondria genes. Out of the 470 samples, 29 samples are Hapmap control subjects, 3 samples are controls subjects from a Belgium family, and another 4 are samples from Example 1 for quality control. Therefore, there were totally 434 unique subjects from this study (103 in A1, 105 in A2, 111 in B1, 111 in B2 and 4 not treated).

The genotyping dataset contained 29 samples from Hapmap project as control for genotyping quality. Of the 1939 SNPs genotyped, 1934 had corresponding Hapmap data. Comparing the genotype calls, the 29 samples had an average concordance rate of 99.63%. However, a couple of SNPs (rs5699 and rs926103) had near 0% concordance between the Hapmap data and the dataset, indicating potential genotyping errors in these SNPs. To control data quality, 8 SNPs with <90% concordance between the Hapmap data and treatment dataset were excluded from association analysis.

After the quality control and filtering, 212 VELCADE treated subjects were included in the association analysis on non-mtSNPs.

Example 3

SNPs with minor allele frequency (MAF) less than 0.01 were excluded from subsequent analysis, since the accuracy of the clustering algorithm used by to generate genotyping calls is relatively low for SNPs with very low minor allele frequencies. There were 11 SNPs in the entire analysis of Example 1 with less than a 90% call rate and these were excluded. Of the remaining SNPs, 26 SNPs had MAF less than 0.01 and these were excluded. Hardy-Weinberg equilibrium (HWE) test was performed. Significant deviation from Hardy-Weinberg equilibrium may indicate potential genotyping errors in a homogenous population. However, moderate deviation from HWE may indicate positive associations with the study endpoints. For the Example 1 study, the HWE test was performed in the Caucasian subjects since they form the largest homogenous population of the study reported herein. SNPs that deviated from HWE with p-value less than 0.05/2000 were excluded from subsequent analysis. There were 5 SNPs from the Example 1 study that failed the HWE test and these were excluded. Appendix 1 lists the total set of SNPs tested, genotype status, call rate, MAF, P-value for HWE test, and the final statistical analysis status. After SNP level QC, 1885 non-mtSNPs were retained for the association analysis.

Out of the 2016 non-mtSNPs genotyped from subjects of Example 2 study, 1939 SNPs were successfully genotyped. There were 6 SNPs with less than 90% call rate and were excluded. Of the remaining SNPs, 11 SNPs had minor allele frequency (MAF) less than 0.01 and were excluded. There were 6 SNPs from the Example 2 study that failed the HWE test (P_HWE<0.05/2000) conducted on the 212 VELCADE treated white subjects and these were excluded. The annotation of the 2016 SNPs are listed in Appendix 1 together with the genotype status, call rate, MAF, P-value for HWE test, and the final statistical analysis status. After QC, 1908 non-mtSNPs were included in the association analysis.

For each non-mtSNP, three genomic models were tested during the association analysis: Additive, Dominant and Recessive. All the non-mtSNPs under study are bi-allelic SNPs with a major allele (A) and a minor allele (B). The Dominant model compares subjects with AA genotype with those with AB or BB genotype. The Recessive model compares subjects with AA or AB genotype with those with BB genotype. The Additive model compares subjects having 0 copy of B (AA) with those have 1 copy of B (AB), and those with 2 copy of B (BB). MAF greater than 1% was used as threshold to filter SNPs during the quality control process. Included in this analysis is the following: 1) for the Dominant model, only SNPs with at least 4 AB/BB subjects will be analyzed; 2) for the Recessive model, only SNPs with at least 4 BB subjects will be analyzed; 3) for the Additive model, only SNPs with at least 4 BB subjects, or those with at least 4 AB and 0 BB subjects, will be analyzed. After this filtration, a total of 1445 SNPs for analysis were included in the Additive model, 1885 SNPs were included in the Dominant model, and 1136 SNPs were included in the Recessive model. For Example 2 SNPs, three genomic models were tested during the association analysis and minor allele frequency greater than 1% was used as a threshold to filter SNPs during the quality control process. Under this condition, the minimum number of B alleles each SNP has is 5, since 212×2×1%=4.24, which can be of either one of the three possible genotype distributions: 1) 207 AA, 5 AB, 0 BB; 2) 208 AA, 3AB, 1BB; 3) 209 AA, 1 AB, 2 BB. Included in this analysis is the following: 1) for the Dominant model, only SNPs with at least 5 AB/BB subjects will be analyzed; 2) for the Recessive model, only SNPs with at least 5 BB subjects will be analyzed; 3) for the Additive model, only SNPs with at least 5 BB subjects, or those with at least 5 AB and 0 BB subjects, will be analyzed. After this filtration, there were 1441 SNPs for analysis in additive model, 1908 SNPs for dominant model, and 1259 SNPs for recessive model.

All 64 tagging mtSNPs analyzed in Example 1 study had a >90% call rate. This genotype mtSNP genotype information was used to impute the genotype of other 80 common mtSNPs and 9 haplogroups following the method described by Saxena and colleagues (Saxena et al. (2006), *American Journal of Human Genetics*, vol. 79, pages 54-61). After SNP level quality control and this filtering process, 62 mtSNPs were retained for association analysis. Note that a slightly higher MAF threshold was used for mtSNPs: 0.025 instead of 0.01 because the mtSNPs do not form heterozygous genotypes, and subjects with AA genotype against those with BB genotype were analyzed. The list of mtSNPs genotyped and imputed are listed in Appendix 1. Because there were no significant associations between the mitochondrial SNPs and peripheral neuropathy categories, they were not genotyped in the Example 2 dataset.

A quantile-quantile plot (Q-Q plot) is a graphical data analysis method for comparing ordered values of a statistic with quantiles of a specific theoretical distribution. In large-scale candidate gene association studies, Q-Q plots of p-values for association are often used for visualizing the result. In such plots, the −log 10 transformed p-values are ordered and then plotted against the −log 10 transformed quantiles of uniform distribution. Under the null hypothesis that there is no SNP associated with the endpoints of interest, the p-values should follow a uniform distribution and the Q-Q plot should fall right on the expected line. While deviation of the Q-Q plot from the expected line at the extreme right hand tail may indicate significant associations, deviation of a large portion of the Q-Q plot may indicate potential data errors, such as genotyping errors or population stratification. For each of the endpoints, an initial analysis was performed using $\chi^2$ tests on the dominant model and the Q-Q plot was used to identify potential problems in the data.

For the 139 VELCADE™ treated Caucasian subjects in Example 1, Q-Q plots of the $\chi^2$ tests on each of the three adverse events of interest (peripheral sensory neuropathy, peripheral neuropathy NEC, and neuralgia) using the dominant model on the 1885 non-mtSNPs showed no obvious genotyping problems in the data. The observed P-values are generally bigger (smaller in −log 10 scale) than the expected P-values but fall within the 95% confidence intervals of the expected P-values. But some observed P-values fall out of the lower boundary of 95% confidence interval on the −log 10 scale. This is consistent with small sample sizes using this analysis, which has relatively lower power.

Demographic and baseline characteristics of the 139 VELCADE treated Caucasian subjects in Example 1 are summarized in Tables 1 and 2. There were no significant differences in these baseline characteristics between the subset of 139 subjects included in the pharmacogenomics study and the 340 subjects in the VMP arm of the Example 1 study, except for "region" since non-Caucasian subjects were excluded in the Pharmacogenomic (PGx) cohort.

TABLE 1

Comparison of the Baseline Continuous Characteristic for VELCADE Treated Caucasian Subjects with the Clinical Study Cohort Treated with VELCADE.

| Baseline Continuous Characteristic | Example 1 Study (N = 340) Median (range) | Example 1 PGx Subset (N = 139) Median (range) |
| --- | --- | --- |
| Age (years) | 71 (57-90) | 72 (58-90) |
| Body Surface Area (m$^2$) | 1.8 (1.3-2.4) | 1.8 (1.4-2.4) |
| Height (cm) | 165 (139-187) | 167 (145-187) |
| Weight (kg) | 71 (40.3-127.9) | 73.5 (47-125) |
| BMI | 25.9 (15.6-49.2) | 26 (17.1-39.6) |

TABLE 2

Comparison of the Baseline Categorical Characteristic for VELCADE Treated Caucasian Subjects with the Clinical Study Cohort Treated with VELCADE.

| Baseline Categorical Characteristic | | Example 1 Study (N = 340) No. of Patients (%) | Example 1 PGx Subset (N = 139) No. of Patients (%) |
|---|---|---|---|
| Sex | Female | 168 (49.4) | 61 (43.9) |
| | Male | 172 (50.6) | 78 (56.1) |
| Baseline b2-microglobin | <2.5 mg/L | 42 (12.4) | 13 (9.4) |
| | 2.5 to 5.5 mg/L | 187 (55.0) | 88 (63.3) |
| | >5.5 mg/L | 111 (32.6) | 38 (27.3) |
| Baseline Albumin | <3.5 g/dL | 198 (58.2) | 75 (54.0) |
| | >=3.5 g/dL | 142 (41.8) | 64 (46.0) |
| Region | Europe | 266 (78.2) | 117 (84.2) |
| | North America | 32 (9.4) | 22 (15.8) |
| | Other | 42 (12.4) | 0 (0.0) |
| Sensory or Motor Neuropathy at Entry | | 37 (10.9) | 17 (12.2) |
| Baseline Diabetes | | 39 (11.5) | 19 (13.7) |
| Baseline Creatinine Clearance Group | <30 mL/min | 19 (5.6) | 8 (5.8) |
| | 30-50 mL/min | 92 (27.1) | 33 (23.7) |
| | 51-80 mL/min | 167 (49.1) | 70 (50.4) |
| | >80 mL/min | 62 (18.2) | 28 (20.1) |

The demographics information and baseline characteristics of the 212 VELCADE™ treated subjects in Example 2 were compared with the 139 VELCADE™ treated white subjects in Example 1 as shown in Tables 3 and 4. Significant differences in subjects' age, height, BMI, baseline β-microglobin, baseline albumin, baseline creatinine clearance, neuropathy and diabetes history were observed between the 139 subjects from Example 1 and the 212 subjects from Example 2.

TABLE 3

Comparison of the Baseline Continuous Characteristic.

| Baseline Continuous Characteristic | Example 1 PGx Subset (Vc-mp) (N = 139) Median (range) | Example 2 Study PGx Subset (B1 and B2 arms) (N = 212) Median (range) | P* |
|---|---|---|---|
| Age (years) | 72 (58-90) | 56 (31-65) | <0.0001 |
| Body Surface Area (m$^2$) | 1.8 (1.4-2.4) | 1.8 (1.3-2.5) | 0.15 |
| Height (cm) | 167 (145-187) | 170 (146-196) | 0.02 |
| Weight (kg) | 73.5 (47-125) | 72 (42-126) | 0.78 |
| BMI | 26 (17.1-39.6) | 24.9 (17.9-38.7) | 0.03 |

*P-values from two-sided t-tests.

TABLE 4

Comparison of the Baseline Categorical Characteristic

| Baseline Categorical Characteristic | | Example 1 PGx Subset (Vc-mp) (N = 139) No. of Patients (%) | Example 2 PGx Subset (B1 and B2 arms) (N = 212) No. of Patients (%) | P* |
|---|---|---|---|---|
| Sex | Female | 61 (43.9) | 92 (43.4) | 0.93 |
| | Male | 78 (56.1) | 120 (56.6) | |
| Baseline b2-microglobin | <2.5 mg/L | 13 (9.4) | 60 (28.3) | <0.0001 |
| | 2.5 to 5.5 mg/L | 88 (63.3) | 103 (48.6) | |
| | >5.5 mg/L | 38 (27.3) | 49 (23.1) | |
| Baseline Albumin | <3.5 g/dL | 75 (54.0) | 50 (23.6) | <0.0001 |
| | >=3.5 g/dL | 64 (46.0) | 162 (76.4) | |
| Region | Europe | 117 (84.2) | NA | NA |
| | North America | 22 (15.8) | NA | |
| | Other | 0 (0.0) | NA | |
| Sensory or Motor Neuropathy at Entry | | 17 (12.2) | 1 (0.5) | <0.0001 |
| Baseline Diabetes | | 19 (13.7) | 12 (5.7) | 0.01 |
| Baseline Creatinine Clearance Group | <30 mL/min | 8 (5.8) | 17 (8.0) | <0.0001 |
| | 30-50 mL/min | 33 (23.7) | 19 (9.0) | |
| | 51-80 mL/min | 70 (50.4) | 62 (29.3) | |
| | >80 mL/min | 28 (20.1) | 114 (53.8) | |

*P-values from Chi-square tests.

All statistical tests were interpreted at the 5% significance level (2-tailed) unless otherwise specified. Multiple testing corrections were conducted using Bonferroni adjustment for single locus (SNP) association tests and random permutation (1000 times) for multi-loci (Haplotype) association tests.

Association of individual SNPs with VELCADE™ treatment-emergent peripheral neuropathy events was performed based on genotypic, dominant and recessive models using logistic regression in SAS (PROC LOGISTIC, SAS, v. 9.1). Samples within each peripheral neuropathy subgroup can be further stratified according to the number of AE incidences, the maximum NCI toxicity grade of the adverse event, the reversibility, and the duration of the adverse event. Baseline demographic data such as age, gender, race, country, baseline toxicity grade of neurological disease, and risk-factors for peripheral neuropathy determined in clinical study of adverse event of VELCADE™ were used as covariates. Multiple testing corrections were conducted using Bonferroni adjustment.

Haplotype association analysis was performed based on Haplotype Trend Regression using the Logistic Regression module in HelixTree (HelixTree, v. 6.2). Association of the haplotypes formed by 2 to 4 neighboring SNPs on the same chromosome with peripheral neuropathy was tested, with age, gender, race, country, and risk-factors for peripheral neuropathy determined in the ongoing VELCADE™ adverse event clinical study as covariates. Haplotype frequencies were estimated using the expectation maximization (EM) algorithm in HelixTree. Multiple testing corrections were performed by all-marker permutation (1000 times). During each permutation, the group label (e.g. with neuralgia, without neuralgia) for each sample was randomly permutated. The haplotype association test was performed based on the permutated group label. The frequency that a haplotype marker had a more significant P-value in the permutated dataset than the original dataset was used as the permutation adjusted P-value.

The primary endpoints included onset of each of the three adverse events of interest: peripheral sensory neuropathy (68 cases/71 controls), peripheral neuropathy NEC (72 cases/67 controls), Neuralgia (59 cases/80 controls), and any occurrence of any one of the three adverse events (AE3: 84 cases/55 controls). Patients were grouped into cases (those with any onset of the adverse events of interest) and controls (those without the adverse event of interest). As shown in Table 5, the frequencies of the onset of adverse events of interest in the 139 selected subjects for the pharmacogenomics subset were similar to those in the VELCADE™ treated arm of Example 1.

TABLE 5

Comparison of the Frequency of Adverse Event of Interest for VELCADE Treated Caucasian Subjects Genotyped with the VELCADE Treated Clinical Trial Subjects.

| AE Cases of Interest | Study (VMP) No. of Patients (%) (N = 340) | PGx Subset (VMP) No. of Patients (%) (N = 139) |
|---|---|---|
| Peripheral Neuropathy NEC | 159 (46.8) | 72 (51.8) |
| Peripheral Sensory Neuropathy | 151 (44.4) | 68 (48.9) |
| Neuralgia | 121 (35.6) | 59 (42.4) |
| Any of the three AE | 187 (55.0) | 84 (60.4) |

For consistency between Example 1 and Example 2, the regression model included all the predetermined covariates including: age, gender, baseline b2-microglobin, baseline albumin, body surface area (BSA), body mass index (BMI), neuropathy status at entry (either sensory neuropathy or motor neuropathy), diabetes status at baseline, and creatinine clearance at baseline (categorized into 4 groups: <30 mL/min, ≥30 and ≤50 mL/min, >50 and ≤80 mL/min, >80 mL/min).

After Bonferroni correction for multiple testing using $P=0.05/(1885+62)=2.57E-5$ as threshold, none of the 1885 non-mtSNPs and 62 mtSNPs showed any significant association with the onset of any of the adverse event endpoints tested in Example 1 Correction by False Discovery Rate (FDR)<0.05 was used as threshold for multiple testing and no SNPs showed significant association with the onset of any of the adverse events tested.

Haplotype association analysis was performed based on Haplotype Trend Regression using the Logistic Regression module in HelixTree (HelixTree v. 6.2). Association of the haplotypes formed by 2 to 4 neighboring non-mtSNPs on the same chromosome with peripheral neuropathy was tested. Haplotype frequencies were estimated using the expectation maximization (EM) algorithm in HelixTree. After multiple testing corrections using all-marker permutation (1000 times), none of the haplotypes tested showed any significant association (P-permutation<0.05) with any of the adverse event endpoints under study.

Association of individual SNPs with time of onset of VELCADE treatment-emergent peripheral neuropathy events was performed based on genotypic, dominant and recessive models using log rank test and Cox regression in SAS (PROC LIFETEST and PROC PHREG, SAS v. 9.1). Baseline demographic data such as age, gender, race, country, baseline toxicity grade of neurological disease, and risk-factors for peripheral neuropathy determined in the ongoing VELCADE™ adverse event clinical study were tested as covariates for the Cox proportional hazards model. Multiple testing corrections were conducted using Bonferroni adjustment.

The secondary end points tested included time to onset of any peripheral neuropathy (72 events/67 censored), time to onset of grade≥2 peripheral neuropathy (50 events/89 censored), and time to onset of grade≥3 peripheral neuropathy (21 events/118 censored). The same set of covariates used in the logistic regression were used as covariates for the Cox proportional hazards model for each of the end points.

After Bonferroni correction for multiple testing using $P=0.05/(1885+62)=2.57E-5$ as threshold, one SNP (rs4553808 from gene CTLA4) showed significant association (Wald Type 3 test P=1.68E-6, FDR=0.0019) with time to onset of Peripheral Neuropathy in recessive model. The proportionality test showed that the proportional assumption of Cox regression was not violated by this model. Patients with the homozygous genotype of the minor allele of rs4553808 (GG) tend to have earlier onset of Peripheral Neuropathy than those that contain only 1 or 0 copy of the minor allele (AA/AG); median time to onset for these subjects was 36 days compared to 89.5 days. There were only 6 patients who had the GG genotype in the dataset. All of them had some level of Peripheral Neuropathy during the Example 1 study: 2 subjects had maximum grade 1 peripheral neuropathy, 2 had maximum grade 2 peripheral neuropathy, and 2 subjects had maximum grade 3 peripheral neuropathy. None of the 5 subjects with the GG genotype of rs4553808 from the non-VELCADE treated arm had any onset of peripheral neuropathy during the trial.

The association of single markers with the cumulative dosage of VELCADE at the onset of peripheral neuropathy was tested. For this endpoint, rs4553808 showed a marginally significant association. Patients with homozygous genotype of the minor allele of rs4553808 (GG) tended to have onset of peripheral peuropathy at a lower cumulative dosage of VELCADE™ than those that contained only 1 or 0 copy of the minor allele (AA/AG): the median time to onset for these subjects was 8.45 mg/m$^2$ vs. 18.8 mg/m$^2$.

One SNP, rs1474642 of gene PSMB1, showed significant associations with time to onset of level≥2 Peripheral neuropathy in recessive model after Bonferroni correction. If using FDR≤0.05 as threshold, another SNP, rs12568757 of CTSS, also showed a significant association. The proportionality test showed that the proportional assumption of Cox regression was not violated by this model.

Using the cumulative dosage of VELCADE to the onset of level≥2 Peripheral neuropathy as endpoint, rs1474642 and rs12568757 showed a marginally significant association. However, another SNP, rs916758 of DYNC1I1, showed a significant association with the cumulative dosage of VELCADE to onset of level≥2 peripheral neuropathy in the dominant model: Wald Type 3 test P=6.14E-6, FDR=0.012.

Patients with the homozygous genotype of the minor allele of rs1474642 (GG) tended to have earlier onset of level≥2 peripheral neuropathy than those that contained only 1 or 0 copies of the minor allele (AA/AG): the median time to onset for these subjects was 26 days vs. 109 days; whereas median cumulative dosage of VELCADE™ to time to onset was 6.9 mg/m$^2$ vs. 22.1 mg/m$^2$. There were 4 patients with the homozygous GG genotype. Two of these subjects had maximum grade 3 peripheral neuropathy, one had grade 2 peripheral neuropathy, and one had no peripheral neuropathy during the study. In the MP-treated arm of Example 1 study, 6 of the 142 successfully genotyped MP-treated Caucasian subjects had GG genotype of rs1474642. None of these subjects had any onset of peripheral neuropathy during the trial.

Similarly, patients with the homozygous genotype of the minor allele of rs12568757 (GG) tended to have earlier onset of level≥Grade 2 peripheral neuropathy than those that contained only 1 or 0 copy of the minor allele (AA/AG); the median time to onset was 88 days vs. 113 days; whereas the median cumulative dosage of VELCADE™ to onset was 18.4 mg/m$^2$ vs. 23.2 mg/m$^2$. There were 39 patients with the GG genotype: 10 with grade 3 peripheral neuropathy, 11 with grade 2, 6 with grade 1 and 12 with no peripheral neuropathy during the study. In the MP-treated arm of Example 1 study, 39 of the 142 successfully genotyped MP-treated Caucasian subjects had GG genotype of rs12568757. But only two of them had peripheral neuropathy during the trial: one had grade 1, the other had grade 2.

Patients carrying 1 or 2 copies of the minor allele of rs916758 (AG/GG) tended to have earlier onset of level≥2 peripheral neuropathy than those that contain 0 copies of the minor allele (AA): median time to onset was 75 days vs. 109 days; whereas median cumulative dosage of VELCADE to onset was 16.6 mg/m$^2$ vs. 23.2 mg/m$^2$. There were 32 patients with AG/GG genotypes: 8 with grade 3 peripheral neuropathy, 9 with grade 2, 2 with grade 1 and 13 with no peripheral neuropathy during the study. In the MP-treated arm of Example 1 study, 33 of the 142 successfully genotyped MP-treated caucasian subjects had AG/GG genotypes of rs916758. But only two of them had grade 1 peripheral neuropathy during the trial.

No SNP showed a significant association with time to onset of level≥Grade 3 peripheral neuropathy after Bonferroni correction. But using FDR<0.05 as threshold, one SNP (rs11974610 of gene GJE1) showed a significant association. Using cumulative dosage of VELCADE™ to the onset of level≥Grade 3 peripheral neuropathy as the endpoint, rs11974610 showed a marginally significant association. Patients with the homozygous genotype of the minor allele of rs11974610 (AA) tended to have an earlier onset of level≥Grade 3 peripheral neuropathy than those that contain only 1 or 0 copies of the minor allele (GG/GA): median time to onset was 97 days vs. 113 days; whereas median cumulative dosage of VELCADE™ to onset was 17.6 mg/m$^2$ vs. 24.7 mg/m$^2$. There were 6 patients with the AA genotypes. Four of them had maximum grade 3 peripheral neuropathy, and 2 had no peripheral neuropathy during the study. In the MP-treated arm of the Example 1 study, 5 of the 142 successfully genotyped MP-treated Caucasian subjects had AA genotype of rs11974610. Only one of them had grade 2 peripheral neuropathy during the trial.

The subjects who had the homozygous genotypes for the minor allele of rs4553808, rs1474642, and rs11974610, had no overlap. But among the 39 subjects who had GG genotype of rs12568757, 2 of them also had GG of rs4553808, 1 had GG of rs1474642, and 3 had AA of rs11974610. All 6 subjects who had two copies of the markers identified had onset of peripheral neuropathy during the Example 1 study. Among the 32 patients with AG/GG genotypes of rs916758, 16 of them also had GG of rs12568757 (11 of them had onset of peripheral neuropathy), 2 had both GG of rs4553808 and GG of rs12568757, 1 had GG of rs1474642 and GG of rs12568757, 1 had AA of rs11974610 and GG of rs12568757, and 1 had GG of rs1474642.

The 5 SNPs which either showed significant associations with time of onset of different levels of peripheral neuropathy or with cumulative dosage of VELCADE™ to the onset of peripheral neuropathy in Example 1 were validated with the Example 2 study. The onset rate of peripheral neuropathy event (including peripheral neuropathies, dysesthesia, and paraesthesia) is 44.8% in Example 2, comparable with the 51.8% in the Example 1 (P=0.24). The analysis results are summarized in Table 6. Based on the raw p-values for the association tests, none of the significant associations identified in Example 1 were replicated in Example 2. However, rs4553808 showed the same trend in association with time to onset of peripheral neuropathy in the recessive model (Wald Type 3 P-value=0.138). Patients with homogenous genotype of the minor allele of rs4553808 (GG) tend to have earlier onset of peripheral neuropathy than those that contain only 1 or 0 copy of the minor allele (AA/AG): median time to onset was 68 days vs. 70 days. Even though rs916758 also had a relatively low P-value of association (Wald Type 3 P-value=0.113), the trend is opposite to what was observed in Example 1.

TABLE 6

Verification of Example 1 significant associations in Example 2.

| SNP ID | Endpoint | Genetic Model | P-value |
|---|---|---|---|
| rs4553808 | time to onset of PN | Recessive | 0.138 |
| rs1474642 | time to onset of level >=2 PN | Recessive | 0.933 |
| rs12568757 | time to onset of level >=2 PN | Recessive | 0.444 |
| rs11974610 | time to onset of level >=3 PN | Recessive | 0.996 |
| rs916758 | cumulative dosage of VELCADE to level >=2 PN | Dominant | 0.113 |

The association with time and cumulative dosage of VELCADE™ to the onset of different levels of peripheral neuropathy in all 1908 SNPs in Example 2 was tested. No significant associations was identified after multiple testing correction using Bonfferoni (0.05/1908=2.62E-05). The primary endpoints in Example 2 were tested in all 1908 genotyped SNPs: peripheral sensory neuropathy (8 cases/204 controls), peripheral neuropathy NEC (44 cases/168 controls), Neuralgia (9 cases/203 controls), and any occurrence of any one of the three adverse events (AE3: 51 cases/161 controls). One SNP (rs1261134 of gene TCF4) showed significant association with the onset of any one of the adverse events of interest in the additive model after multiple testing correction by FDR adjustments.

The inventors have identified 4 SNPs (rs4553808 of CTLA4, rs1474642 of PSMB1, rs12568757 of CTSS, and rs11974610 of GJE1) which showed significant associations with time to onset of different levels of peripheral neuropathy in the recessive model. These SNPs also showed marginally significant associations with cumulative dosage of VELCADE™ to the onset of peripheral neuropathy in the recessive model. Another SNP, rs916758 of DYNC1I1, showed significant association with the cumulative dosage of VELCADE™ to onset of level≥Grade 2 peripheral neuropathy in the dominant model in Example 1. However, it did not have significant association with time to onset of peripheral neuropathy. These associations are related to VELCADE™ treatment because subjects with the identified markers in the MP treated arm had zero or very low frequency of onset of peripheral neuropathy during the trial. None of these associations were replicated in Example 2. One SNP, rs4553808, showed the same trend of association with time to onset of peripheral neuropathy in Example 2 (P=0.138).

APPENDIX 1

| | SNPs genotyped | | | | | |
|---|---|---|---|---|---|---|
| SNP ID | Genome Build Version | Chr | Position | dbSNP Version | Gene Symbol | Gene ID |
| rs307370 | 36 | 1 | 1263141 | 127 | DVL1 | 1855 |
| rs307359 | 36 | 1 | 1269877 | 127 | DVL1 | 1855 |
| rs6695456 | 36 | 1 | 10193113 | 127 | KIF1B | 23095 |

APPENDIX 1-continued

SNPs genotyped

| SNP ID | Genome Build Version | Chr | Position | dbSNP Version | Gene Symbol | Gene ID |
|---|---|---|---|---|---|---|
| rs11586485 | 36 | 1 | 10231613 | 127 | KIF1B | 23095 |
| rs3748575 | 36 | 1 | 10264939 | 127 | KIF1B | 23095 |
| rs3748576 | 36 | 1 | 10265216 | 127 | KIF1B | 23095 |
| rs17397129 | 36 | 1 | 10268049 | 127 | KIF1B | 23095 |
| rs8019 | 36 | 1 | 10289074 | 127 | KIF1B | 23095 |
| rs17402390 | 36 | 1 | 10321547 | 127 | KIF1B | 23095 |
| rs17034775 | 36 | 1 | 10321595 | 127 | KIF1B | 23095 |
| rs12125492 | 36 | 1 | 10344465 | 127 | KIF1B | 23095 |
| rs12403443 | 36 | 1 | 10346575 | 127 | KIF1B | 23095 |
| rs1002076 | 36 | 1 | 10361479 | 127 | KIF1B | 23095 |
| rs11121556 | 36 | 1 | 10365454 | 127 | KIF1B | 23095 |
| rs1474868 | 36 | 1 | 11966751 | 127 | MFN2 | 9927 |
| rs6675934 | 36 | 1 | 11974992 | 127 | MFN2 | 9927 |
| rs1810563 | 36 | 1 | 11976617 | 127 | MFN2 | 9927 |
| rs2236057 | 36 | 1 | 11984792 | 127 | MFN2 | 9927 |
| rs183339 | 36 | 1 | 19536998 | 127 | CAPZB | 832 |
| rs2268813 | 36 | 1 | 19539395 | 127 | CAPZB | 832 |
| rs16862684 | 36 | 1 | 19546907 | 127 | CAPZB | 832 |
| rs1535036 | 36 | 1 | 19549511 | 127 | CAPZB | 644075 |
| rs214336 | 36 | 1 | 19551060 | 127 | CAPZB | 644075 |
| rs214338 | 36 | 1 | 19552460 | 127 | CAPZB | 644075 |
| rs761308 | 36 | 1 | 19552706 | 127 | CAPZB | 644075 |
| rs127037 | 36 | 1 | 19552732 | 127 | CAPZB | 644075 |
| rs17477654 | 36 | 1 | 19553131 | 127 | CAPZB | 644075 |
| rs7533994 | 36 | 1 | 19553860 | 127 | CAPZB | 644075 |
| rs214344 | 36 | 1 | 19554234 | 127 | CAPZB | 644075 |
| rs10917432 | 36 | 1 | 19571448 | 127 | CAPZB | 832 |
| rs17394154 | 36 | 1 | 19578972 | 127 | CAPZB | 832 |
| rs4911987 | 36 | 1 | 19594090 | 127 | CAPZB | 644083 |
| rs12030205 | 36 | 1 | 19612761 | 127 | CAPZB | 832 |
| rs3829833 | 36 | 1 | 19620083 | 127 | CAPZB | 832 |
| rs11586303 | 36 | 1 | 19637868 | 127 | CAPZB | 832 |
| rs4911997 | 36 | 1 | 19638256 | 127 | CAPZB | 832 |
| rs1472568 | 36 | 1 | 19639019 | 127 | CAPZB | 832 |
| rs9651016 | 36 | 1 | 19641828 | 127 | CAPZB | 832 |
| rs10458381 | 36 | 1 | 19641830 | 127 | CAPZB | 832 |
| rs10917451 | 36 | 1 | 19641910 | 127 | CAPZB | 832 |
| rs2088824 | 36 | 1 | 19657921 | 127 | CAPZB | 832 |
| rs12401874 | 36 | 1 | 19662284 | 127 | CAPZB | 832 |
| rs9887859 | 36 | 1 | 19664676 | 127 | CAPZB | 832 |
| rs10799815 | 36 | 1 | 19668262 | 127 | CAPZB | 832 |
| rs16862800 | 36 | 1 | 19668729 | 127 | CAPZB | 832 |
| rs4912104 | 36 | 1 | 19672216 | 127 | CAPZB | 832 |
| rs10799817 | 36 | 1 | 19678584 | 127 | CAPZB | 832 |
| rs6664461 | 36 | 1 | 19681758 | 127 | CAPZB | 832 |
| rs10917461 | 36 | 1 | 19682345 | 127 | CAPZB | 832 |
| rs1995309 | 36 | 1 | 19691836 | 127 | CAPZB | 832 |
| rs16822407 | 36 | 1 | 19693956 | 127 | CAPZB | 832 |
| rs1474646 | 36 | 1 | 22314612 | 127 | WNT4 | 54361 |
| rs2235530 | 36 | 1 | 22316347 | 127 | WNT4 | 54361 |
| rs12756110 | 36 | 1 | 22319735 | 127 | WNT4 | 54361 |
| rs3765350 | 36 | 1 | 22319903 | 127 | WNT4 | 54361 |
| rs12131703 | 36 | 1 | 22320804 | 127 | WNT4 | 54361 |
| rs6678992 | 36 | 1 | 22326429 | 127 | WNT4 | 54361 |
| rs10917158 | 36 | 1 | 22326960 | 127 | WNT4 | 54361 |
| rs7544210 | 36 | 1 | 22327729 | 127 | WNT4 | 54361 |
| rs12042083 | 36 | 1 | 22345319 | 127 | WNT4 | 54361 |
| rs7542242 | 36 | 1 | 22350080 | 127 | WNT4 | 54361 |
| rs1042114 | 36 | 1 | 29011562 | 127 | OPRD1 | 4985 |
| rs2236861 | 36 | 1 | 29012343 | 127 | OPRD1 | 4985 |
| rs678849 | 36 | 1 | 29017775 | 127 | OPRD1 | 4985 |
| rs4654322 | 36 | 1 | 29023832 | 127 | OPRD1 | 4985 |
| rs2236855 | 36 | 1 | 29034586 | 127 | OPRD1 | 4985 |
| rs6697423 | 36 | 1 | 29043082 | 127 | OPRD1 | 4985 |
| rs529520 | 36 | 1 | 29047533 | 127 | OPRD1 | 4985 |
| rs581111 | 36 | 1 | 29047960 | 127 | OPRD1 | 4985 |
| rs508448 | 36 | 1 | 29054112 | 127 | OPRD1 | 4985 |
| rs204069 | 36 | 1 | 29067405 | 127 | OPRD1 | 4985 |
| rs16866009 | 36 | 1 | 33013876 | 127 | YARS | 8565 |
| rs699005 | 36 | 1 | 33018389 | 127 | YARS | 8565 |
| rs2282294 | 36 | 1 | 33018764 | 127 | YARS | 8565 |
| rs881393 | 36 | 1 | 33029232 | 127 | YARS | 8565 |
| rs10753265 | 36 | 1 | 33036599 | 127 | YARS | 8565 |
| rs10798918 | 36 | 1 | 33048568 | 127 | YARS | 8565 |

APPENDIX 1-continued

SNPs genotyped

| SNP ID | Genome Build Version | Chr | Position | dbSNP Version | Gene Symbol | Gene ID |
|---|---|---|---|---|---|---|
| rs6677618 | 36 | 1 | 33053704 | 127 | YARS | 8565 |
| rs1741969 | 36 | 1 | 35028712 | 127 | GJB3 | 2701 |
| rs6668196 | 36 | 1 | 35841791 | 127 | PSMB2 | 5690 |
| rs676614 | 36 | 1 | 35880097 | 127 | PSMB2 | 5690 |
| rs959 | 36 | 1 | 71090849 | 127 | PTGER3 | 5733 |
| rs6656853 | 36 | 1 | 71097887 | 127 | PTGER3 | 5733 |
| rs6672081 | 36 | 1 | 71097928 | 127 | PTGER3 | 5733 |
| rs7533733 | 36 | 1 | 71100822 | 127 | PTGER3 | 5733 |
| rs17131465 | 36 | 1 | 71102044 | 127 | PTGER3 | 5733 |
| rs5702 | 36 | 1 | 71104018 | 127 | PTGER3 | 5733 |
| rs1409986 | 36 | 1 | 71104086 | 127 | PTGER3 | 5733 |
| rs11209706 | 36 | 1 | 71105576 | 127 | PTGER3 | 5733 |
| rs1327449 | 36 | 1 | 71110513 | 127 | PTGER3 | 5733 |
| rs11804767 | 36 | 1 | 71124792 | 127 | PTGER3 | 5733 |
| rs4147114 | 36 | 1 | 71129253 | 127 | PTGER3 | 5733 |
| rs1409165 | 36 | 1 | 71136693 | 127 | PTGER3 | 5733 |
| rs11209710 | 36 | 1 | 71137606 | 127 | PTGER3 | 5733 |
| rs1359835 | 36 | 1 | 71138082 | 127 | PTGER3 | 5733 |
| rs4650094 | 36 | 1 | 71138571 | 127 | PTGER3 | 5733 |
| rs6659643 | 36 | 1 | 71139087 | 127 | PTGER3 | 5733 |
| rs942976 | 36 | 1 | 71140159 | 127 | PTGER3 | 5733 |
| rs17541722 | 36 | 1 | 71146509 | 127 | PTGER3 | 5733 |
| rs1327466 | 36 | 1 | 71146695 | 127 | PTGER3 | 5733 |
| rs17542063 | 36 | 1 | 71156823 | 127 | PTGER3 | 5733 |
| rs6424410 | 36 | 1 | 71157268 | 127 | PTGER3 | 5733 |
| rs602383 | 36 | 1 | 71164234 | 127 | PTGER3 | 5733 |
| rs499641 | 36 | 1 | 71185970 | 127 | PTGER3 | 5733 |
| rs650194 | 36 | 1 | 71187451 | 127 | PTGER3 | 5733 |
| rs7541936 | 36 | 1 | 71188185 | 127 | PTGER3 | 5733 |
| rs5699 | 36 | 1 | 71191040 | 127 | PTGER3 | 5733 |
| rs977214 | 36 | 1 | 71198848 | 127 | PTGER3 | 5733 |
| rs626398 | 36 | 1 | 71205572 | 127 | PTGER3 | 5733 |
| rs3819790 | 36 | 1 | 71215723 | 127 | PTGER3 | 5733 |
| rs2050066 | 36 | 1 | 71227723 | 127 | PTGER3 | 5733 |
| rs6424414 | 36 | 1 | 71228058 | 127 | PTGER3 | 5733 |
| rs2300167 | 36 | 1 | 71230750 | 127 | PTGER3 | 5733 |
| rs10789314 | 36 | 1 | 71237136 | 127 | PTGER3 | 5733 |
| rs5693 | 36 | 1 | 71247370 | 127 | PTGER3 | 5733 |
| rs5675 | 36 | 1 | 71250127 | 127 | PTGER3 | 5733 |
| rs5673 | 36 | 1 | 71250429 | 127 | PTGER3 | 5733 |
| rs8179390 | 36 | 1 | 71266953 | 127 | PTGER3 | 5733 |
| rs2817864 | 36 | 1 | 71275693 | 127 | PTGER3 | 5733 |
| rs2744902 | 36 | 1 | 71280129 | 127 | PTGER3 | 5733 |
| rs2817869 | 36 | 1 | 71294992 | 127 | PTGER3 | 9406 |
| rs2488787 | 36 | 1 | 112807331 | 127 | WNT2B | 55917 |
| rs11102479 | 36 | 1 | 112808327 | 127 | WNT2B | 7482 |
| rs1175649 | 36 | 1 | 112820800 | 127 | WNT2B | 7482 |
| rs1175650 | 36 | 1 | 112821097 | 127 | WNT2B | 7482 |
| rs10776751 | 36 | 1 | 112821821 | 127 | WNT2B | 7482 |
| rs1759693 | 36 | 1 | 112824815 | 127 | WNT2B | 7482 |
| rs974442 | 36 | 1 | 112829794 | 127 | WNT2B | 7482 |
| rs351359 | 36 | 1 | 112841800 | 127 | WNT2B | 7482 |
| rs11807828 | 36 | 1 | 112844072 | 127 | WNT2B | 7482 |
| rs351364 | 36 | 1 | 112846584 | 127 | WNT2B | 7482 |
| rs3790606 | 36 | 1 | 112853709 | 127 | WNT2B | 7482 |
| rs351370 | 36 | 1 | 112856182 | 127 | WNT2B | 7482 |
| rs12138754 | 36 | 1 | 112857176 | 127 | WNT2B | 7482 |
| rs910697 | 36 | 1 | 112864648 | 127 | WNT2B | 7482 |
| rs2273368 | 36 | 1 | 112865294 | 127 | WNT2B | 7482 |
| rs11102489 | 36 | 1 | 112865873 | 127 | WNT2B | 7482 |
| rs11102516 | 36 | 1 | 112962873 | 127 | CAPZA1 | 54879 |
| rs7550315 | 36 | 1 | 112993391 | 127 | CAPZA1 | 829 |
| rs1238 | 36 | 1 | 113015620 | 127 | CAPZA1 | 829 |
| rs6537748 | 36 | 1 | 113015904 | 127 | CAPZA1 | 829 |
| rs6330 | 36 | 1 | 115630836 | 127 | NGFB | 4803 |
| rs6328 | 36 | 1 | 115631466 | 127 | NGFB | 4803 |
| rs2268793 | 36 | 1 | 115633306 | 127 | NGFB | 4803 |
| rs2268792 | 36 | 1 | 115634405 | 127 | NGFB | 4803 |
| rs17033622 | 36 | 1 | 115635714 | 127 | NGFB | 4803 |
| rs2239622 | 36 | 1 | 115639232 | 127 | NGFB | 4803 |
| rs2856811 | 36 | 1 | 115639805 | 127 | NGFB | 4803 |
| rs6678788 | 36 | 1 | 115641194 | 127 | NGFB | 4803 |
| rs11102920 | 36 | 1 | 115642633 | 127 | NGFB | 4803 |
| rs6686615 | 36 | 1 | 115646569 | 127 | NGFB | 4803 |

APPENDIX 1-continued

SNPs genotyped

| SNP ID | Genome Build Version | Chr | Position | dbSNP Version | Gene Symbol | Gene ID |
|---|---|---|---|---|---|---|
| rs12058927 | 36 | 1 | 115647744 | 127 | NGFB | 4803 |
| rs12402406 | 36 | 1 | 115649911 | 127 | NGFB | 4803 |
| rs4644491 | 36 | 1 | 115654507 | 127 | NGFB | 4803 |
| rs7555016 | 36 | 1 | 115656670 | 127 | NGFB | 4803 |
| rs10858073 | 36 | 1 | 115657510 | 127 | NGFB | 4803 |
| rs10776798 | 36 | 1 | 115663777 | 127 | NGFB | 4803 |
| rs7530686 | 36 | 1 | 115665423 | 127 | NGFB | 4803 |
| rs4839436 | 36 | 1 | 115670612 | 127 | NGFB | 4803 |
| rs10858074 | 36 | 1 | 115671833 | 127 | NGFB | 4803 |
| rs11102925 | 36 | 1 | 115672877 | 127 | NGFB | 4803 |
| rs4839028 | 36 | 1 | 115673789 | 127 | NGFB | 4803 |
| rs4320778 | 36 | 1 | 115676454 | 127 | NGFB | 4803 |
| rs10745349 | 36 | 1 | 115676717 | 127 | NGFB | 4803 |
| rs11102929 | 36 | 1 | 115678026 | 127 | NGFB | 4803 |
| rs17033706 | 36 | 1 | 115679147 | 127 | NGFB | 4803 |
| rs4634908 | 36 | 1 | 115681344 | 127 | NGFB | 4803 |
| rs17540656 | 36 | 1 | 115681655 | 127 | NGFB | 4803 |
| rs10776801 | 36 | 1 | 115684064 | 127 | NGFB | 4803 |
| rs11583020 | 36 | 1 | 115685317 | 127 | NGFB | 4803 |
| rs11102932 | 36 | 1 | 115687606 | 127 | NGFB | 4803 |
| rs4310443 | 36 | 1 | 115688564 | 127 | NGFB | 4803 |
| rs4073110 | 36 | 1 | 115688850 | 127 | NGFB | 4803 |
| rs10776802 | 36 | 1 | 115690449 | 127 | NGFB | 4803 |
| rs10858078 | 36 | 1 | 115690525 | 127 | NGFB | 4803 |
| rs11576175 | 36 | 1 | 148994018 | 127 | CTSS | 1520 |
| rs10888390 | 36 | 1 | 148994163 | 127 | CTSS | 1520 |
| rs12568757 | 36 | 1 | 148996417 | 127 | CTSS | 1520 |
| rs7172 | 36 | 1 | 149638762 | 127 | PSMB4 | 5692 |
| rs4603 | 36 | 1 | 149640649 | 127 | PSMB4 | 5692 |
| rs2485662 | 36 | 1 | 154350092 | 127 | LMNA | 4000 |
| rs6686943 | 36 | 1 | 154359615 | 127 | LMNA | 4000 |
| rs9427236 | 36 | 1 | 154360030 | 127 | LMNA | 4000 |
| rs505058 | 36 | 1 | 154372809 | 127 | LMNA | 4000 |
| rs4641 | 36 | 1 | 154374158 | 127 | LMNA | 4000 |
| rs6669212 | 36 | 1 | 154376937 | 127 | LMNA | 4000 |
| rs7544967 | 36 | 1 | 155048992 | 127 | NTRK1 | 9047 |
| rs926103 | 36 | 1 | 155051606 | 127 | NTRK1 | 9047 |
| rs2150906 | 36 | 1 | 155051980 | 127 | NTRK1 | 4914 |
| rs1800601 | 36 | 1 | 155052241 | 127 | NTRK1 | 4914 |
| rs4661222 | 36 | 1 | 155061630 | 127 | NTRK1 | 9047 |
| rs2768747 | 36 | 1 | 155067388 | 127 | NTRK1 | 3645 |
| rs1998977 | 36 | 1 | 155070745 | 127 | NTRK1 | 3645 |
| rs6674412 | 36 | 1 | 155071605 | 127 | NTRK1 | 3645 |
| rs11812062 | 36 | 1 | 155072321 | 127 | NTRK1 | 3645 |
| rs4661229 | 36 | 1 | 155075830 | 127 | NTRK1 | 3645 |
| rs12145540 | 36 | 1 | 155084568 | 127 | NTRK1 | 3645 |
| rs4661063 | 36 | 1 | 155091425 | 127 | NTRK1 | 3645 |
| rs11264577 | 36 | 1 | 155103591 | 127 | NTRK1 | 4914 |
| rs1800879 | 36 | 1 | 155104765 | 127 | NTRK1 | 4914 |
| rs12132885 | 36 | 1 | 155108960 | 127 | NTRK1 | 4914 |
| rs6334 | 36 | 1 | 155112857 | 127 | NTRK1 | 4914 |
| rs2644604 | 36 | 1 | 155114730 | 127 | NTRK1 | 4914 |
| rs2768755 | 36 | 1 | 155114744 | 127 | NTRK1 | 4914 |
| rs6336 | 36 | 1 | 155115542 | 127 | NTRK1 | 4914 |
| rs2644596 | 36 | 1 | 155118938 | 127 | NTRK1 | 4914 |
| rs943551 | 36 | 1 | 155122121 | 127 | NTRK1 | 4914 |
| rs4657015 | 36 | 1 | 159539065 | 127 | MPZ | 4359 |
| rs4657016 | 36 | 1 | 159539150 | 127 | MPZ | 4359 |
| rs7532602 | 36 | 1 | 159540935 | 127 | MPZ | 4359 |
| rs16832786 | 36 | 1 | 159541529 | 127 | MPZ | 4359 |
| rs7531561 | 36 | 1 | 159545854 | 127 | MPZ | 4359 |
| rs11579939 | 36 | 1 | 159546142 | 127 | MPZ | 4359 |
| rs3813630 | 36 | 1 | 159546873 | 127 | MPZ | 4359 |
| rs4131826 | 36 | 1 | 159549008 | 127 | MPZ | 6391 |
| rs11265589 | 36 | 1 | 159550921 | 127 | MPZ | 6391 |
| rs16832809 | 36 | 1 | 159551916 | 127 | MPZ | 6391 |
| rs7734 | 36 | 1 | 180619244 | 127 | GLUL | 2752 |
| rs9347 | 36 | 1 | 180619821 | 127 | GLUL | 2752 |
| rs17462824 | 36 | 1 | 180622870 | 127 | GLUL | 2752 |
| rs1058111 | 36 | 1 | 180623022 | 127 | GLUL | 2752 |
| rs12136955 | 36 | 1 | 180625567 | 127 | GLUL | 2752 |
| rs12403634 | 36 | 1 | 180626938 | 127 | GLUL | 2752 |
| rs12756106 | 36 | 1 | 180631766 | 127 | GLUL | 127670 |
| rs1925829 | 36 | 1 | 180637397 | 127 | GLUL | 127670 |

APPENDIX 1-continued

SNPs genotyped

| SNP ID | Genome Build Version | Chr | Position | dbSNP Version | Gene Symbol | Gene ID |
|---|---|---|---|---|---|---|
| rs689470 | 36 | 1 | 184907681 | 127 | PTGS2 | 5743 |
| rs2206593 | 36 | 1 | 184909052 | 127 | PTGS2 | 5743 |
| rs5275 | 36 | 1 | 184909681 | 127 | PTGS2 | 5743 |
| rs5277 | 36 | 1 | 184914820 | 127 | PTGS2 | 5743 |
| rs4648261 | 36 | 1 | 184915627 | 127 | PTGS2 | 5743 |
| rs2745557 | 36 | 1 | 184915844 | 127 | PTGS2 | 5743 |
| rs689466 | 36 | 1 | 184917374 | 127 | PTGS2 | 5743 |
| rs12042763 | 36 | 1 | 184918499 | 127 | PTGS2 | 5743 |
| rs10911907 | 36 | 1 | 184923125 | 127 | PTGS2 | 5743 |
| rs1009658 | 36 | 1 | 226170404 | 127 | WNT9A | 7483 |
| rs12748472 | 36 | 1 | 226170998 | 127 | WNT9A | 7483 |
| rs3820623 | 36 | 1 | 226173885 | 127 | WNT9A | 7483 |
| rs8192633 | 36 | 1 | 226176094 | 127 | WNT9A | 7483 |
| rs10127943 | 36 | 1 | 226176687 | 127 | WNT9A | 7483 |
| rs12046421 | 36 | 1 | 226177357 | 127 | WNT9A | 7483 |
| rs2527614 | 36 | 1 | 226193093 | 127 | WNT9A | 7483 |
| rs680997 | 36 | 1 | 226193850 | 127 | WNT9A | 7483 |
| rs697763 | 36 | 1 | 226259245 | 127 | WNT3A | 89780 |
| rs708122 | 36 | 1 | 226283620 | 127 | WNT3A | 89780 |
| rs10916258 | 36 | 1 | 226286505 | 127 | WNT3A | 89780 |
| rs752107 | 36 | 1 | 226313974 | 127 | WNT3A | 89780 |
| rs7536290 | 36 | 1 | 228903325 | 127 | AGT | 183 |
| rs11122574 | 36 | 1 | 228904431 | 127 | AGT | 183 |
| rs7079 | 36 | 1 | 228904954 | 127 | AGT | 183 |
| rs2478523 | 36 | 1 | 228908132 | 127 | AGT | 183 |
| rs3789664 | 36 | 1 | 228910047 | 127 | AGT | 183 |
| rs2493131 | 36 | 1 | 228910128 | 127 | AGT | 183 |
| rs6687360 | 36 | 1 | 228911615 | 127 | AGT | 183 |
| rs11568054 | 36 | 1 | 228912178 | 127 | AGT | 183 |
| rs699 | 36 | 1 | 228912417 | 127 | AGT | 183 |
| rs4762 | 36 | 1 | 228912600 | 127 | AGT | 183 |
| rs2004776 | 36 | 1 | 228915325 | 127 | AGT | 183 |
| rs3789678 | 36 | 1 | 228916105 | 127 | AGT | 183 |
| rs5050 | 36 | 1 | 228916509 | 127 | AGT | 183 |
| rs2071406 | 36 | 1 | 228917264 | 127 | AGT | 183 |
| rs2493137 | 36 | 1 | 228918739 | 127 | AGT | 183 |
| rs1326886 | 36 | 1 | 228926383 | 127 | AGT | 183 |
| rs6746378 | 36 | 2 | 43851116 | 127 | DYNC2LI1 | 130271 |
| rs7606529 | 36 | 2 | 43854289 | 127 | DYNC2LI1 | 51626 |
| rs2288709 | 36 | 2 | 43857514 | 127 | DYNC2LI1 | 51626 |
| rs17031514 | 36 | 2 | 43860159 | 127 | DYNC2LI1 | 51626 |
| rs3815995 | 36 | 2 | 43864124 | 127 | DYNC2LI1 | 51626 |
| rs11695056 | 36 | 2 | 43868913 | 127 | DYNC2LI1 | 51626 |
| rs9309107 | 36 | 2 | 43875330 | 127 | DYNC2LI1 | 51626 |
| rs10208317 | 36 | 2 | 43880895 | 127 | DYNC2LI1 | 51626 |
| rs11556157 | 36 | 2 | 43881517 | 127 | DYNC2LI1 | 51626 |
| rs17343939 | 36 | 2 | 54614833 | 127 | SPTBN1 | 56969 |
| rs9309255 | 36 | 2 | 54627345 | 127 | SPTBN1 | 6711 |
| rs11892788 | 36 | 2 | 54637612 | 127 | SPTBN1 | 6711 |
| rs4671961 | 36 | 2 | 54652100 | 127 | SPTBN1 | 6711 |
| rs10204932 | 36 | 2 | 54652631 | 127 | SPTBN1 | 6711 |
| rs2229506 | 36 | 2 | 54698294 | 127 | SPTBN1 | 6711 |
| rs6715538 | 36 | 2 | 54701438 | 127 | SPTBN1 | 6711 |
| rs2971886 | 36 | 2 | 54704804 | 127 | SPTBN1 | 6711 |
| rs12624153 | 36 | 2 | 54711305 | 127 | SPTBN1 | 6711 |
| rs1052788 | 36 | 2 | 54712015 | 127 | SPTBN1 | 6711 |
| rs2229503 | 36 | 2 | 54712168 | 127 | SPTBN1 | 6711 |
| rs2941579 | 36 | 2 | 54715329 | 127 | SPTBN1 | 6711 |
| rs6760298 | 36 | 2 | 54719324 | 127 | SPTBN1 | 6711 |
| rs6748715 | 36 | 2 | 54719998 | 127 | SPTBN1 | 6711 |
| rs2941584 | 36 | 2 | 54735125 | 127 | SPTBN1 | 6711 |
| rs17344343 | 36 | 2 | 54735795 | 127 | SPTBN1 | 6711 |
| rs17416242 | 36 | 2 | 54737289 | 127 | SPTBN1 | 6711 |
| rs17416291 | 36 | 2 | 54740732 | 127 | SPTBN1 | 6711 |
| rs17046097 | 36 | 2 | 54741579 | 127 | SPTBN1 | 6711 |
| rs2941587 | 36 | 2 | 54742001 | 127 | SPTBN1 | 6711 |
| rs2971879 | 36 | 2 | 54742037 | 127 | SPTBN1 | 6711 |
| rs2971878 | 36 | 2 | 54742282 | 127 | SPTBN1 | 6711 |
| rs1047465 | 36 | 2 | 54742519 | 127 | SPTBN1 | 6711 |
| rs2971877 | 36 | 2 | 54742640 | 127 | SPTBN1 | 6711 |
| rs10528 | 36 | 2 | 54742653 | 127 | SPTBN1 | 6711 |
| rs1047499 | 36 | 2 | 54742894 | 127 | SPTBN1 | 6711 |
| rs3771748 | 36 | 2 | 74460295 | 127 | DCTN1 | 1639 |
| rs2229169 | 36 | 2 | 96144443 | 127 | ADRA2B | 151 |

APPENDIX 1-continued

SNPs genotyped

| SNP ID | Genome Build Version | Chr | Position | dbSNP Version | Gene Symbol | Gene ID |
|---|---|---|---|---|---|---|
| rs4426564 | 36 | 2 | 96144713 | 127 | ADRA2B | 151 |
| rs1042705 | 36 | 2 | 97640959 | 127 | ACTR1B | 10120 |
| rs11692435 | 36 | 2 | 97641786 | 127 | ACTR1B | 10120 |
| rs10496323 | 36 | 2 | 97656271 | 127 | ACTR1B | 728537 |
| rs6745653 | 36 | 2 | 97656429 | 127 | ACTR1B | 728537 |
| rs9711882 | 36 | 2 | 149508149 | 127 | KIF5C | 727742 |
| rs9711441 | 36 | 2 | 149508356 | 127 | KIF5C | 727742 |
| rs9288721 | 36 | 2 | 149508624 | 127 | KIF5C | 727742 |
| rs9711454 | 36 | 2 | 149508669 | 127 | KIF5C | 727742 |
| rs9711815 | 36 | 2 | 149512294 | 127 | KIF5C | 727742 |
| rs11893617 | 36 | 2 | 149513319 | 127 | KIF5C | 727742 |
| rs9287841 | 36 | 2 | 149513821 | 127 | KIF5C | 727742 |
| rs9679707 | 36 | 2 | 149513954 | 127 | KIF5C | 727742 |
| rs9679278 | 36 | 2 | 149514117 | 127 | KIF5C | 727742 |
| rs4459700 | 36 | 2 | 149517344 | 127 | KIF5C | 727742 |
| rs6751242 | 36 | 2 | 149517518 | 127 | KIF5C | 727742 |
| rs7569536 | 36 | 2 | 149519120 | 127 | KIF5C | 727742 |
| rs6722730 | 36 | 2 | 149520062 | 127 | KIF5C | 727742 |
| rs4130557 | 36 | 2 | 149520882 | 127 | KIF5C | 727742 |
| rs6710001 | 36 | 2 | 149525164 | 127 | KIF5C | 727742 |
| rs11885746 | 36 | 2 | 149525475 | 127 | KIF5C | 727742 |
| rs11885858 | 36 | 2 | 149525687 | 127 | KIF5C | 727742 |
| rs6730426 | 36 | 2 | 149530152 | 127 | KIF5C | 727742 |
| rs7564570 | 36 | 2 | 149535222 | 127 | KIF5C | 727742 |
| rs6717088 | 36 | 2 | 149535880 | 127 | KIF5C | 727742 |
| rs6738453 | 36 | 2 | 149539156 | 127 | KIF5C | 727742 |
| rs6755213 | 36 | 2 | 149539190 | 127 | KIF5C | 727742 |
| rs11901442 | 36 | 2 | 149546378 | 127 | KIF5C | 727742 |
| rs7573156 | 36 | 2 | 149558655 | 127 | KIF5C | 727742 |
| rs6738277 | 36 | 2 | 149562206 | 127 | KIF5C | 727742 |
| rs6736802 | 36 | 2 | 149566980 | 127 | KIF5C | 727742 |
| rs6721330 | 36 | 2 | 149567152 | 127 | KIF5C | 727742 |
| rs6435220 | 36 | 2 | 149569925 | 127 | KIF5C | 727742 |
| rs4667372 | 36 | 2 | 149570507 | 127 | KIF5C | 727742 |
| rs4452104 | 36 | 2 | 149571652 | 127 | KIF5C | 727742 |
| rs6435387 | 36 | 2 | 149573496 | 127 | KIF5C | 727742 |
| rs7577450 | 36 | 2 | 149584207 | 127 | KIF5C | 727742 |
| rs1568853 | 36 | 2 | 149594837 | 127 | KIF5C | 130576 |
| rs10933498 | 36 | 2 | 149595915 | 127 | KIF5C | 130576 |
| rs17347194 | 36 | 2 | 149596430 | 127 | KIF5C | 130576 |
| rs7574918 | 36 | 2 | 165647425 | 127 | SCN3A | 6328 |
| rs2165208 | 36 | 2 | 165658095 | 127 | SCN3A | 6328 |
| rs1347992 | 36 | 2 | 165670111 | 127 | SCN3A | 6328 |
| rs1158135 | 36 | 2 | 165688559 | 127 | SCN3A | 6328 |
| rs17829560 | 36 | 2 | 165689591 | 127 | SCN3A | 6328 |
| rs1439806 | 36 | 2 | 165700012 | 127 | SCN3A | 6328 |
| rs1946892 | 36 | 2 | 165704353 | 127 | SCN3A | 6328 |
| rs16850131 | 36 | 2 | 165711725 | 127 | SCN3A | 6328 |
| rs4667792 | 36 | 2 | 165726600 | 127 | SCN3A | 6328 |
| rs4145346 | 36 | 2 | 165739570 | 127 | SCN3A | 6328 |
| rs11894144 | 36 | 2 | 165742551 | 127 | SCN3A | 6328 |
| rs2390165 | 36 | 2 | 165768165 | 127 | SCN3A | 6328 |
| rs6719780 | 36 | 2 | 165774518 | 127 | SCN3A | 6328 |
| rs6727857 | 36 | 2 | 165776529 | 127 | SCN3A | 6328 |
| rs17804037 | 36 | 2 | 166761274 | 127 | SCN9A | 6335 |
| rs16851751 | 36 | 2 | 166761632 | 127 | SCN9A | 6335 |
| rs7582791 | 36 | 2 | 166777500 | 127 | SCN9A | 6335 |
| rs7600169 | 36 | 2 | 166789225 | 127 | SCN9A | 6335 |
| rs16851799 | 36 | 2 | 166794660 | 127 | SCN9A | 6335 |
| rs10170041 | 36 | 2 | 166795107 | 127 | SCN9A | 6335 |
| rs6746030 | 36 | 2 | 166807404 | 127 | SCN9A | 6335 |
| rs2155879 | 36 | 2 | 166808492 | 127 | SCN9A | 6335 |
| rs4426541 | 36 | 2 | 166829202 | 127 | SCN9A | 6335 |
| rs4453709 | 36 | 2 | 166834700 | 127 | SCN9A | 6335 |
| rs12477229 | 36 | 2 | 166843902 | 127 | SCN9A | 6335 |
| rs6706811 | 36 | 2 | 166849948 | 127 | SCN9A | 6335 |
| rs9917250 | 36 | 2 | 166851501 | 127 | SCN9A | 6335 |
| rs6747673 | 36 | 2 | 166853220 | 127 | SCN9A | 6335 |
| rs13402180 | 36 | 2 | 166853241 | 127 | SCN9A | 6335 |
| rs12620053 | 36 | 2 | 166866532 | 127 | SCN9A | 6335 |
| rs13017637 | 36 | 2 | 166868192 | 127 | SCN9A | 6335 |
| rs12994338 | 36 | 2 | 166868275 | 127 | SCN9A | 6335 |
| rs4605385 | 36 | 2 | 166869844 | 127 | SCN9A | 6335 |
| rs10171225 | 36 | 2 | 166870895 | 127 | SCN9A | 6335 |

APPENDIX 1-continued

SNPs genotyped

| SNP ID | Genome Build Version | Chr | Position | dbSNP Version | Gene Symbol | Gene ID |
|---|---|---|---|---|---|---|
| rs9646771 | 36 | 2 | 166871289 | 127 | SCN9A | 6335 |
| rs4455169 | 36 | 2 | 166886401 | 127 | SCN9A | 6335 |
| rs2138349 | 36 | 2 | 172251643 | 127 | DYNC1I2 | 1781 |
| rs312924 | 36 | 2 | 172272267 | 127 | DYNC1I2 | 1781 |
| rs10185633 | 36 | 2 | 172286107 | 127 | DYNC1I2 | 1781 |
| rs13000153 | 36 | 2 | 172294313 | 127 | DYNC1I2 | 1781 |
| rs2292816 | 36 | 2 | 172294960 | 127 | DYNC1I2 | 1781 |
| rs2001350 | 36 | 2 | 177808671 | 127 | NFE2L2 | 4780 |
| rs1806649 | 36 | 2 | 177826398 | 127 | NFE2L2 | 4780 |
| rs13005431 | 36 | 2 | 177829358 | 127 | NFE2L2 | 4780 |
| rs2364722 | 36 | 2 | 177833033 | 127 | NFE2L2 | 4780 |
| rs2364725 | 36 | 2 | 177841234 | 127 | NFE2L2 | 4780 |
| rs16865105 | 36 | 2 | 177844875 | 127 | NFE2L2 | 4780 |
| rs10202963 | 36 | 2 | 201950152 | 127 | TRAK2 | 66008 |
| rs10931943 | 36 | 2 | 201951206 | 127 | TRAK2 | 66008 |
| rs3795966 | 36 | 2 | 201953489 | 127 | TRAK2 | 66008 |
| rs2244438 | 36 | 2 | 201960784 | 127 | TRAK2 | 66008 |
| rs13022344 | 36 | 2 | 201972401 | 127 | TRAK2 | 66008 |
| rs2540334 | 36 | 2 | 201979592 | 127 | TRAK2 | 66008 |
| rs12473209 | 36 | 2 | 201988178 | 127 | TRAK2 | 729191 |
| rs1009276 | 36 | 2 | 202031201 | 127 | TRAK2 | 55437 |
| rs733618 | 36 | 2 | 204439189 | 127 | CTLA4 | 1493 |
| rs4553808 | 36 | 2 | 204439250 | 127 | CTLA4 | 1493 |
| rs11571316 | 36 | 2 | 204439334 | 127 | CTLA4 | 1493 |
| rs11571317 | 36 | 2 | 204440253 | 127 | CTLA4 | 1493 |
| rs5742909 | 36 | 2 | 204440592 | 127 | CTLA4 | 1493 |
| rs231775 | 36 | 2 | 204440959 | 127 | CTLA4 | 1493 |
| rs7596898 | 36 | 2 | 219427976 | 127 | WNT6 | 7475 |
| rs11695967 | 36 | 2 | 219429434 | 127 | WNT6 | 7475 |
| rs6747776 | 36 | 2 | 219433562 | 127 | WNT6 | 7475 |
| rs6754599 | 36 | 2 | 219440386 | 127 | WNT6 | 7475 |
| rs3806557 | 36 | 2 | 219452118 | 127 | WNT10A; WNT6 | 80326 |
| rs7349332 | 36 | 2 | 219464627 | 127 | WNT10A | 80326 |
| rs4574113 | 36 | 2 | 219470906 | 127 | WNT10A | 80326 |
| rs755302 | 36 | 2 | 241301068 | 127 | KIF1A | 547 |
| rs4613 | 36 | 2 | 241301960 | 127 | KIF1A | 547 |
| rs3732341 | 36 | 2 | 241304217 | 127 | KIF1A | 547 |
| rs3772050 | 36 | 2 | 241321413 | 127 | KIF1A | 547 |
| rs10174559 | 36 | 2 | 241325449 | 127 | KIF1A | 547 |
| rs7578279 | 36 | 2 | 241325937 | 127 | KIF1A | 547 |
| rs3772054 | 36 | 2 | 241327201 | 127 | KIF1A | 547 |
| rs10196604 | 36 | 2 | 241334748 | 127 | KIF1A | 547 |
| rs7598218 | 36 | 2 | 241346971 | 127 | KIF1A | 547 |
| rs3821345 | 36 | 2 | 241352633 | 127 | KIF1A | 547 |
| rs11681427 | 36 | 2 | 241354900 | 127 | KIF1A | 547 |
| rs2288750 | 36 | 2 | 241371118 | 127 | KIF1A | 547 |
| rs4676366 | 36 | 2 | 241382335 | 127 | KIF1A | 547 |
| rs734586 | 36 | 2 | 241383427 | 127 | KIF1A | 547 |
| rs3755539 | 36 | 2 | 241387890 | 127 | KIF1A | 547 |
| rs4455151 | 36 | 2 | 241393045 | 127 | KIF1A | 547 |
| rs13416949 | 36 | 2 | 241399871 | 127 | KIF1A | 547 |
| rs4499423 | 36 | 2 | 241411841 | 127 | KIF1A | 547 |
| rs12329123 | 36 | 2 | 241414545 | 127 | KIF1A | 547 |
| rs11720627 | 36 | 3 | 13830351 | 127 | WNT7A | 7476 |
| rs3762725 | 36 | 3 | 13832578 | 127 | WNT7A | 7476 |
| rs1124479 | 36 | 3 | 13832859 | 127 | WNT7A | 7476 |
| rs1124480 | 36 | 3 | 13832970 | 127 | WNT7A | 7476 |
| rs1946620 | 36 | 3 | 13833800 | 127 | WNT7A | 7476 |
| rs3796314 | 36 | 3 | 13834333 | 127 | WNT7A | 7476 |
| rs9840696 | 36 | 3 | 13840076 | 127 | WNT7A | 7476 |
| rs867606 | 36 | 3 | 13844302 | 127 | WNT7A | 7476 |
| rs934453 | 36 | 3 | 13845053 | 127 | WNT7A | 7476 |
| rs11711182 | 36 | 3 | 13851910 | 127 | WNT7A | 7476 |
| rs12634112 | 36 | 3 | 13853890 | 127 | WNT7A | 7476 |
| rs17038695 | 36 | 3 | 13854204 | 127 | WNT7A | 7476 |
| rs934450 | 36 | 3 | 13862730 | 127 | WNT7A | 7476 |
| rs1433355 | 36 | 3 | 13865845 | 127 | WNT7A | 7476 |
| rs4257529 | 36 | 3 | 13869117 | 127 | WNT7A | 7476 |
| rs1433354 | 36 | 3 | 13872246 | 127 | WNT7A | 7476 |
| rs9849631 | 36 | 3 | 13877001 | 127 | WNT7A | 7476 |
| rs7641735 | 36 | 3 | 13878475 | 127 | WNT7A | 7476 |
| rs9864031 | 36 | 3 | 13883072 | 127 | WNT7A | 7476 |
| rs12635960 | 36 | 3 | 13887489 | 127 | WNT7A | 7476 |
| rs4685042 | 36 | 3 | 13888278 | 127 | WNT7A | 7476 |

APPENDIX 1-continued

SNPs genotyped

| SNP ID | Genome Build Version | Chr | Position | dbSNP Version | Gene Symbol | Gene ID |
|---|---|---|---|---|---|---|
| rs10865716 | 36 | 3 | 13889685 | 127 | WNT7A | 7476 |
| rs1991850 | 36 | 3 | 13897995 | 127 | WNT7A | 7476 |
| rs1077524 | 36 | 3 | 13905134 | 127 | WNT7A | 7476 |
| rs6768050 | 36 | 3 | 13905491 | 127 | WNT7A | 7476 |
| rs6782149 | 36 | 3 | 32544100 | 127 | DYNC1LI1 | 51143 |
| rs2303857 | 36 | 3 | 32553509 | 127 | DYNC1LI1 | 51143 |
| rs7621564 | 36 | 3 | 32572011 | 127 | DYNC1LI1 | 51143 |
| rs342729 | 36 | 3 | 32572136 | 127 | DYNC1LI1 | 51143 |
| rs9867284 | 36 | 3 | 32574240 | 127 | DYNC1LI1 | 51143 |
| rs3853720 | 36 | 3 | 32590673 | 127 | DYNC1LI1 | 51143 |
| rs11564445 | 36 | 3 | 41242756 | 127 | CTNNB1 | 1499 |
| rs11564447 | 36 | 3 | 41243358 | 127 | CTNNB1 | 1499 |
| rs4135385 | 36 | 3 | 41254444 | 127 | CTNNB1 | 1499 |
| rs2953 | 36 | 3 | 41256392 | 127 | CTNNB1 | 1499 |
| rs11706227 | 36 | 3 | 55471300 | 127 | WNT5A | 7474 |
| rs597437 | 36 | 3 | 55471449 | 127 | WNT5A | 7474 |
| rs11710229 | 36 | 3 | 55472993 | 127 | WNT5A | 7474 |
| rs590386 | 36 | 3 | 55474447 | 127 | WNT5A | 7474 |
| rs1829556 | 36 | 3 | 55476215 | 127 | WNT5A | 7474 |
| rs7622120 | 36 | 3 | 55479770 | 127 | WNT5A | 7474 |
| rs11918967 | 36 | 3 | 55480430 | 127 | WNT5A | 7474 |
| rs648872 | 36 | 3 | 55494897 | 127 | WNT5A | 7474 |
| rs566926 | 36 | 3 | 55495818 | 127 | WNT5A | 7474 |
| rs506611 | 36 | 3 | 55497809 | 127 | WNT5A | 7474 |
| rs557077 | 36 | 3 | 55506307 | 127 | WNT5A | 7474 |
| rs2472671 | 36 | 3 | 120985735 | 127 | NR1I2 | 8856 |
| rs10934498 | 36 | 3 | 120987071 | 127 | NR1I2 | 8856 |
| rs1357459 | 36 | 3 | 120997246 | 127 | NR1I2 | 8856 |
| rs2461822 | 36 | 3 | 121002855 | 127 | NR1I2 | 8856 |
| rs7643645 | 36 | 3 | 121008187 | 127 | NR1I2 | 8856 |
| rs2472681 | 36 | 3 | 121012379 | 127 | NR1I2 | 8856 |
| rs3732359 | 36 | 3 | 121019119 | 127 | NR1I2 | 8856 |
| rs10511395 | 36 | 3 | 121019249 | 127 | NR1I2 | 8856 |
| rs3732360 | 36 | 3 | 121019271 | 127 | NR1I2 | 8856 |
| rs1054190 | 36 | 3 | 121019408 | 127 | NR1I2 | 8856 |
| rs1054191 | 36 | 3 | 121019587 | 127 | NR1I2 | 8856 |
| rs3814057 | 36 | 3 | 121019944 | 127 | NR1I2 | 8856 |
| rs3814058 | 36 | 3 | 121019981 | 127 | NR1I2 | 8856 |
| rs3108749 | 36 | 3 | 121077178 | 127 | GSK3B | 2932 |
| rs6438553 | 36 | 3 | 121122719 | 127 | GSK3B | 2932 |
| rs2199503 | 36 | 3 | 121261179 | 127 | GSK3B | 2932 |
| rs334555 | 36 | 3 | 121286826 | 127 | GSK3B | 2932 |
| rs3755557 | 36 | 3 | 121297647 | 127 | GSK3B | 2932 |
| rs17811013 | 36 | 3 | 121299676 | 127 | GSK3B | 2932 |
| rs17471 | 36 | 3 | 121300363 | 127 | GSK3B | 2932 |
| rs13082681 | 36 | 3 | 123257824 | 127 | CD86 | 942 |
| rs2715277 | 36 | 3 | 123263840 | 127 | CD86 | 942 |
| rs6786977 | 36 | 3 | 123265496 | 127 | CD86 | 942 |
| rs4308217 | 36 | 3 | 123275877 | 127 | CD86 | 942 |
| rs17203439 | 36 | 3 | 123278196 | 127 | CD86 | 942 |
| rs9282641 | 36 | 3 | 123279458 | 127 | CD86 | 942 |
| rs2681422 | 36 | 3 | 123282244 | 127 | CD86 | 942 |
| rs9831894 | 36 | 3 | 123283177 | 127 | CD86 | 942 |
| rs11717893 | 36 | 3 | 123289515 | 127 | CD86 | 942 |
| rs9836399 | 36 | 3 | 123294501 | 127 | CD86 | 942 |
| rs13064913 | 36 | 3 | 123297201 | 127 | CD86 | 942 |
| rs1915092 | 36 | 3 | 123306065 | 127 | CD86 | 942 |
| rs3804588 | 36 | 3 | 123306847 | 127 | CD86 | 942 |
| rs2681417 | 36 | 3 | 123307887 | 127 | CD86 | 942 |
| rs2254911 | 36 | 3 | 123311527 | 127 | CD86 | 942 |
| rs9848900 | 36 | 3 | 123314187 | 127 | CD86 | 942 |
| rs1129055 | 36 | 3 | 123321009 | 127 | CD86 | 942 |
| rs1915087 | 36 | 3 | 123321481 | 127 | CD86 | 942 |
| rs17281995 | 36 | 3 | 123322331 | 127 | CD86 | 942 |
| rs2715272 | 36 | 3 | 123325931 | 127 | CD86 | 942 |
| rs2638363 | 36 | 3 | 149901883 | 127 | AGTR1 | 185 |
| rs2131127 | 36 | 3 | 149906833 | 127 | AGTR1 | 185 |
| rs4681443 | 36 | 3 | 149915159 | 127 | AGTR1 | 185 |
| rs12721241 | 36 | 3 | 149924310 | 127 | AGTR1 | 185 |
| rs379600 | 36 | 3 | 149927175 | 127 | AGTR1 | 185 |
| rs12721331 | 36 | 3 | 149927683 | 127 | AGTR1 | 185 |
| rs388915 | 36 | 3 | 149930446 | 127 | AGTR1 | 185 |
| rs12695902 | 36 | 3 | 149931108 | 127 | AGTR1 | 185 |
| rs385338 | 36 | 3 | 149931846 | 127 | AGTR1 | 185 |

APPENDIX 1-continued

SNPs genotyped

| SNP ID | Genome Build Version | Chr | Position | dbSNP Version | Gene Symbol | Gene ID |
|---|---|---|---|---|---|---|
| rs3772613 | 36 | 3 | 149935399 | 127 | AGTR1 | 185 |
| rs6801836 | 36 | 3 | 149938227 | 127 | AGTR1 | 185 |
| rs5182 | 36 | 3 | 149942085 | 127 | AGTR1 | 185 |
| rs5183 | 36 | 3 | 149942574 | 127 | AGTR1 | 185 |
| rs275645 | 36 | 3 | 149947144 | 127 | AGTR1 | 185 |
| rs12639531 | 36 | 3 | 149948041 | 127 | AGTR1 | 185 |
| rs275643 | 36 | 3 | 149948294 | 127 | AGTR1 | 185 |
| rs4912527 | 36 | 3 | 185352567 | 127 | DVL3 | 440991 |
| rs2175525 | 36 | 3 | 185369639 | 127 | DVL3 | 1857 |
| rs11919795 | 36 | 3 | 185373562 | 127 | DVL3 | 1857 |
| rs1976700 | 36 | 3 | 185375965 | 127 | DVL3 | 1173 |
| rs843346 | 36 | 3 | 185376213 | 127 | DVL3 | 1173 |
| rs17011297 | 36 | 4 | 87152084 | 127 | MAPK10 | 5602 |
| rs2589523 | 36 | 4 | 87152226 | 127 | MAPK10 | 5602 |
| rs7677101 | 36 | 4 | 87154441 | 127 | MAPK10 | 5602 |
| rs2575675 | 36 | 4 | 87154914 | 127 | MAPK10 | 5602 |
| rs7699978 | 36 | 4 | 87155080 | 127 | MAPK10 | 5602 |
| rs1201 | 36 | 4 | 87155492 | 127 | MAPK10 | 5602 |
| rs2589515 | 36 | 4 | 87156612 | 127 | MAPK10 | 5602 |
| rs958 | 36 | 4 | 87156898 | 127 | MAPK10 | 5602 |
| rs3775173 | 36 | 4 | 87173891 | 127 | MAPK10 | 5602 |
| rs1469870 | 36 | 4 | 87178920 | 127 | MAPK10 | 5602 |
| rs1436522 | 36 | 4 | 87183196 | 127 | MAPK10 | 5602 |
| rs6815306 | 36 | 4 | 87185351 | 127 | MAPK10 | 5602 |
| rs9307015 | 36 | 4 | 87188538 | 127 | MAPK10 | 5602 |
| rs1436529 | 36 | 4 | 87198106 | 127 | MAPK10 | 5602 |
| rs3775182 | 36 | 4 | 87198607 | 127 | MAPK10 | 5602 |
| rs4235078 | 36 | 4 | 87248342 | 127 | MAPK10 | 5602 |
| rs6821745 | 36 | 4 | 87257235 | 127 | MAPK10 | 5602 |
| rs4560400 | 36 | 4 | 87290185 | 127 | MAPK10 | 5602 |
| rs6822478 | 36 | 4 | 87295384 | 127 | MAPK10 | 5602 |
| rs17011419 | 36 | 4 | 87321398 | 127 | MAPK10 | 5602 |
| rs1460767 | 36 | 4 | 87326932 | 127 | MAPK10 | 5602 |
| rs12513237 | 36 | 4 | 87334679 | 127 | MAPK10 | 5602 |
| rs12650052 | 36 | 4 | 87357762 | 127 | MAPK10 | 5602 |
| rs1460769 | 36 | 4 | 87361272 | 127 | MAPK10 | 5602 |
| rs17011590 | 36 | 4 | 87388494 | 127 | MAPK10 | 5602 |
| rs6817452 | 36 | 4 | 87390273 | 127 | MAPK10 | 5602 |
| rs10516771 | 36 | 4 | 87390302 | 127 | MAPK10 | 5602 |
| rs1460757 | 36 | 4 | 87401134 | 127 | MAPK10 | 5602 |
| rs6531914 | 36 | 4 | 87403238 | 127 | MAPK10 | 5602 |
| rs6855169 | 36 | 4 | 87409854 | 127 | MAPK10 | 5602 |
| rs12640392 | 36 | 4 | 87417227 | 127 | MAPK10 | 5602 |
| rs17011659 | 36 | 4 | 87427125 | 127 | MAPK10 | 5602 |
| rs4693761 | 36 | 4 | 87430495 | 127 | MAPK10 | 5602 |
| rs17449015 | 36 | 4 | 87440851 | 127 | MAPK10 | 5602 |
| rs7654796 | 36 | 4 | 87450588 | 127 | MAPK10 | 5602 |
| rs11726269 | 36 | 4 | 87452008 | 127 | MAPK10 | 5602 |
| rs769378 | 36 | 4 | 87458788 | 127 | MAPK10 | 5602 |
| rs6531915 | 36 | 4 | 87459044 | 127 | MAPK10 | 5602 |
| rs17409687 | 36 | 4 | 87469460 | 127 | MAPK10 | 5602 |
| rs7677400 | 36 | 4 | 87471821 | 127 | MAPK10 | 5602 |
| rs4611890 | 36 | 4 | 87478030 | 127 | MAPK10 | 5602 |
| rs2904100 | 36 | 4 | 87486850 | 127 | MAPK10 | 5602 |
| rs2869433 | 36 | 4 | 87498120 | 127 | MAPK10 | 5602 |
| rs17011843 | 36 | 4 | 87516818 | 127 | MAPK10 | 5602 |
| rs17418221 | 36 | 4 | 87570385 | 127 | MAPK10 | 5602 |
| rs12507758 | 36 | 4 | 87570764 | 127 | MAPK10 | 5602 |
| rs4488910 | 36 | 4 | 87581858 | 127 | MAPK10 | 5602 |
| rs17452273 | 36 | 4 | 87591032 | 127 | MAPK10 | 5602 |
| rs7675845 | 36 | 4 | 87602300 | 127 | MAPK10 | 5602 |
| rs10015565 | 36 | 4 | 175800806 | 127 | GLRA3 | 8001 |
| rs4695940 | 36 | 4 | 175804386 | 127 | GLRA3 | 8001 |
| rs4334734 | 36 | 4 | 175804733 | 127 | GLRA3 | 8001 |
| rs12511536 | 36 | 4 | 175816017 | 127 | GLRA3 | 8001 |
| rs7686453 | 36 | 4 | 175822378 | 127 | GLRA3 | 8001 |
| rs7697737 | 36 | 4 | 175827908 | 127 | GLRA3 | 8001 |
| rs7700002 | 36 | 4 | 175831882 | 127 | GLRA3 | 8001 |
| rs12648678 | 36 | 4 | 175834855 | 127 | GLRA3 | 8001 |
| rs11939284 | 36 | 4 | 175840333 | 127 | GLRA3 | 8001 |
| rs1352058 | 36 | 4 | 175842980 | 127 | GLRA3 | 8001 |
| rs1471817 | 36 | 4 | 175847125 | 127 | GLRA3 | 8001 |
| rs17363787 | 36 | 4 | 175868255 | 127 | GLRA3 | 8001 |
| rs4695954 | 36 | 4 | 175868561 | 127 | GLRA3 | 8001 |

APPENDIX 1-continued

SNPs genotyped

| SNP ID | Genome Build Version | Chr | Position | dbSNP Version | Gene Symbol | Gene ID |
|---|---|---|---|---|---|---|
| rs9993143 | 36 | 4 | 175873951 | 127 | GLRA3 | 8001 |
| rs4594702 | 36 | 4 | 175878481 | 127 | GLRA3 | 8001 |
| rs17060810 | 36 | 4 | 175885544 | 127 | GLRA3 | 8001 |
| rs9312559 | 36 | 4 | 175886691 | 127 | GLRA3 | 8001 |
| rs12509729 | 36 | 4 | 175891718 | 127 | GLRA3 | 8001 |
| rs6553812 | 36 | 4 | 175894999 | 127 | GLRA3 | 8001 |
| rs13146324 | 36 | 4 | 175895830 | 127 | GLRA3 | 8001 |
| rs6850542 | 36 | 4 | 175898418 | 127 | GLRA3 | 8001 |
| rs1485935 | 36 | 4 | 175907193 | 127 | GLRA3 | 8001 |
| rs17060835 | 36 | 4 | 175907746 | 127 | GLRA3 | 8001 |
| rs17060847 | 36 | 4 | 175910652 | 127 | GLRA3 | 8001 |
| rs7689368 | 36 | 4 | 175916231 | 127 | GLRA3 | 8001 |
| rs2332940 | 36 | 4 | 175929528 | 127 | GLRA3 | 8001 |
| rs6855717 | 36 | 4 | 175931605 | 127 | GLRA3 | 8001 |
| rs10021711 | 36 | 4 | 175948375 | 127 | GLRA3 | 8001 |
| rs4695963 | 36 | 4 | 175949853 | 127 | GLRA3 | 8001 |
| rs1994313 | 36 | 4 | 175953201 | 127 | GLRA3 | 8001 |
| rs4695791 | 36 | 4 | 175960272 | 127 | GLRA3 | 8001 |
| rs6820174 | 36 | 4 | 175963278 | 127 | GLRA3 | 8001 |
| rs6851555 | 36 | 4 | 175966282 | 127 | GLRA3 | 8001 |
| rs7437645 | 36 | 4 | 175990446 | 127 | GLRA3 | 8001 |
| rs6834798 | 36 | 4 | 175996510 | 127 | GLRA3 | 8001 |
| rs4695965 | 36 | 4 | 175996696 | 127 | GLRA3 | 8001 |
| rs4133101 | 36 | 5 | 40715324 | 127 | PTGER4 | 5734 |
| rs2228058 | 36 | 5 | 40717011 | 127 | PTGER4 | 5734 |
| rs11957406 | 36 | 5 | 40719324 | 127 | PTGER4 | 5734 |
| rs4957343 | 36 | 5 | 40730827 | 127 | PTGER4 | 5734 |
| rs1882619 | 36 | 5 | 112106681 | 127 | APC | 324 |
| rs396321 | 36 | 5 | 112141634 | 127 | APC | 728217 |
| rs2439595 | 36 | 5 | 112146237 | 127 | APC | 324 |
| rs1734242 | 36 | 5 | 112153318 | 127 | APC | 324 |
| rs11953943 | 36 | 5 | 112183659 | 127 | APC | 324 |
| rs2229992 | 36 | 5 | 112190753 | 127 | APC | 324 |
| rs351771 | 36 | 5 | 112192460 | 127 | APC | 324 |
| rs13167522 | 36 | 5 | 112195207 | 127 | APC | 324 |
| rs41115 | 36 | 5 | 112203669 | 127 | APC | 324 |
| rs42427 | 36 | 5 | 112204224 | 127 | APC | 324 |
| rs866006 | 36 | 5 | 112204458 | 127 | APC | 324 |
| rs459552 | 36 | 5 | 112204655 | 127 | APC | 324 |
| rs465899 | 36 | 5 | 112205070 | 127 | APC | 324 |
| rs2229995 | 36 | 5 | 112206694 | 127 | APC | 324 |
| rs11242126 | 36 | 5 | 132058313 | 127 | KIF3A | 11127 |
| rs17690965 | 36 | 5 | 132058566 | 127 | KIF3A | 11127 |
| rs1468216 | 36 | 5 | 132064151 | 127 | KIF3A | 11127 |
| rs3798130 | 36 | 5 | 132070045 | 127 | KIF3A | 11127 |
| rs17691077 | 36 | 5 | 132071250 | 127 | KIF3A | 11127 |
| rs3756752 | 36 | 5 | 132101772 | 127 | KIF3A | 11127 |
| rs10041787 | 36 | 5 | 137447393 | 127 | WNT8A | 7478 |
| rs10036244 | 36 | 5 | 137447624 | 127 | WNT8A | 7478 |
| rs6596422 | 36 | 5 | 137454346 | 127 | WNT8A | 7478 |
| rs17109205 | 36 | 5 | 148356356 | 127 | SH3TC2 | 79628 |
| rs11168078 | 36 | 5 | 148357775 | 127 | SH3TC2 | 79628 |
| rs11168079 | 36 | 5 | 148358031 | 127 | SH3TC2 | 79628 |
| rs17109208 | 36 | 5 | 148358668 | 127 | SH3TC2 | 79628 |
| rs1432795 | 36 | 5 | 148358977 | 127 | SH3TC2 | 79628 |
| rs6885467 | 36 | 5 | 148359748 | 127 | SH3TC2 | 79628 |
| rs3763022 | 36 | 5 | 148361271 | 127 | SH3TC2 | 79628 |
| rs1045942 | 36 | 5 | 148361390 | 127 | SH3TC2 | 79628 |
| rs3763020 | 36 | 5 | 148361511 | 127 | SH3TC2 | 79628 |
| rs998304 | 36 | 5 | 148362558 | 127 | SH3TC2 | 79628 |
| rs11740300 | 36 | 5 | 148384113 | 127 | SH3TC2 | 79628 |
| rs17708342 | 36 | 5 | 148385575 | 127 | SH3TC2 | 79628 |
| rs6875902 | 36 | 5 | 148388086 | 127 | SH3TC2 | 79628 |
| rs1432793 | 36 | 5 | 148388294 | 127 | SH3TC2 | 79628 |
| rs10074456 | 36 | 5 | 148390699 | 127 | SH3TC2 | 79628 |
| rs2304034 | 36 | 5 | 148391113 | 127 | SH3TC2 | 79628 |
| rs17109268 | 36 | 5 | 148396298 | 127 | SH3TC2 | 79628 |
| rs17795259 | 36 | 5 | 148397145 | 127 | SH3TC2 | 79628 |
| rs17722293 | 36 | 5 | 148402467 | 127 | SH3TC2 | 79628 |
| rs28173 | 36 | 5 | 148403766 | 127 | SH3TC2 | 79628 |
| rs36076 | 36 | 5 | 148412254 | 127 | SH3TC2 | 79628 |
| rs36044 | 36 | 5 | 148421321 | 127 | SH3TC2 | 79628 |
| rs2915806 | 36 | 5 | 148431108 | 127 | SH3TC2 | 255187 |
| rs252160 | 36 | 5 | 150067438 | 127 | DCTN4 | 51164 |

APPENDIX 1-continued

SNPs genotyped

| SNP ID | Genome Build Version | Chr | Position | dbSNP Version | Gene Symbol | Gene ID |
|---|---|---|---|---|---|---|
| rs3733925 | 36 | 5 | 150070537 | 127 | DCTN4 | 51164 |
| rs11954652 | 36 | 5 | 150078076 | 127 | DCTN4 | 51164 |
| rs9605 | 36 | 5 | 179595857 | 127 | MAPK9 | 5601 |
| rs6895740 | 36 | 5 | 179600539 | 127 | MAPK9 | 5601 |
| rs4601008 | 36 | 5 | 179603122 | 127 | MAPK9 | 5601 |
| rs4362908 | 36 | 5 | 179605431 | 127 | MAPK9 | 5601 |
| rs4147385 | 36 | 5 | 179610123 | 127 | MAPK9 | 5601 |
| rs6863088 | 36 | 5 | 179612366 | 127 | MAPK9 | 5601 |
| rs6868333 | 36 | 5 | 179620378 | 127 | MAPK9 | 5601 |
| rs13185784 | 36 | 5 | 179626674 | 127 | MAPK9 | 5601 |
| rs3111515 | 36 | 5 | 179627958 | 127 | MAPK9 | 5601 |
| rs9968653 | 36 | 5 | 179632110 | 127 | MAPK9 | 5601 |
| rs2112593 | 36 | 5 | 179633209 | 127 | MAPK9 | 5601 |
| rs3812066 | 36 | 5 | 179641502 | 127 | MAPK9 | 5601 |
| rs6867398 | 36 | 5 | 179644666 | 127 | MAPK9 | 5601 |
| rs915654 | 36 | 6 | 31646476 | 127 | TNF | 4049 |
| rs2071590 | 36 | 6 | 31647747 | 127 | TNF | 4049 |
| rs909253 | 36 | 6 | 31648292 | 127 | TNF | 4049 |
| rs1799964 | 36 | 6 | 31650287 | 127 | TNF | 4049 |
| rs1800630 | 36 | 6 | 31650455 | 127 | TNF | 4049 |
| rs1800629 | 36 | 6 | 31651010 | 127 | TNF | 7124 |
| rs3093661 | 36 | 6 | 31651737 | 127 | TNF | 7124 |
| rs3093662 | 36 | 6 | 31652168 | 127 | TNF | 7124 |
| rs4645843 | 36 | 6 | 31652541 | 127 | TNF | 7124 |
| rs769178 | 36 | 6 | 31655493 | 127 | TNF | 4050 |
| rs241429 | 36 | 6 | 32911818 | 127 | PSMB8 | 6891 |
| rs3819715 | 36 | 6 | 32912197 | 127 | PSMB8 | 6891 |
| rs241426 | 36 | 6 | 32912531 | 127 | PSMB8 | 6891 |
| rs3819720 | 36 | 6 | 32912548 | 127 | PSMB8 | 6891 |
| rs17583244 | 36 | 6 | 32912665 | 127 | PSMB8 | 6891 |
| rs3819721 | 36 | 6 | 32912776 | 127 | PSMB8 | 6891 |
| rs1871665 | 36 | 6 | 32912857 | 127 | PSMB8 | 6891 |
| rs241424 | 36 | 6 | 32912912 | 127 | PSMB8 | 6891 |
| rs2239701 | 36 | 6 | 32913027 | 127 | PSMB8 | 6891 |
| rs4713598 | 36 | 6 | 32914764 | 127 | PSMB8 | 6891 |
| rs3763366 | 36 | 6 | 32915424 | 127 | PSMB8 | 6891 |
| rs2071543 | 36 | 6 | 32919607 | 127 | PSMB8 | 5696 |
| rs2071542 | 36 | 6 | 32919623 | 127 | PSMB8 | 5696 |
| rs2071463 | 36 | 6 | 32920506 | 127 | PSMB8; PSMB9 | 5696 |
| rs2071541 | 36 | 6 | 32920836 | 127 | PSMB8; PSMB9 | 6890 |
| rs9469283 | 36 | 6 | 32921734 | 127 | PSMB8; PSMB9 | 6890 |
| rs2071482 | 36 | 6 | 32924678 | 127 | PSMB8; PSMB9 | 6890 |
| rs241423 | 36 | 6 | 32925988 | 127 | PSMB8; PSMB9 | 6890 |
| rs2071538 | 36 | 6 | 32926656 | 127 | PSMB8; PSMB9 | 6890 |
| rs4148879 | 36 | 6 | 32927456 | 127 | PSMB8; PSMB9 | 6890 |
| rs991760 | 36 | 6 | 32931545 | 127 | PSMB9 | 5698 |
| rs17587 | 36 | 6 | 32933068 | 127 | PSMB9 | 5698 |
| rs9276831 | 36 | 6 | 32940011 | 127 | PSMB9 | 5698 |
| rs851027 | 36 | 6 | 36098853 | 127 | MAPK14 | 116369 |
| rs13196204 | 36 | 6 | 36106754 | 127 | MAPK14 | 1432 |
| rs3804454 | 36 | 6 | 36114976 | 127 | MAPK14 | 1432 |
| rs2237094 | 36 | 6 | 36116122 | 127 | MAPK14 | 1432 |
| rs12211012 | 36 | 6 | 36146186 | 127 | MAPK14 | 1432 |
| rs9357207 | 36 | 6 | 36147131 | 127 | MAPK14 | 1432 |
| rs851006 | 36 | 6 | 36173163 | 127 | MAPK14 | 1432 |
| rs6457878 | 36 | 6 | 36184258 | 127 | MAPK14 | 1432 |
| rs3804452 | 36 | 6 | 36184912 | 127 | MAPK14 | 1432 |
| rs3804451 | 36 | 6 | 36185939 | 127 | MAPK14 | 1432 |
| rs6922865 | 36 | 6 | 36202166 | 127 | MAPK13 | 5603 |
| rs3761977 | 36 | 6 | 36204425 | 127 | MAPK13 | 5603 |
| rs1059227 | 36 | 6 | 36206388 | 127 | MAPK13 | 5603 |
| rs2071864 | 36 | 6 | 36208710 | 127 | MAPK13 | 5603 |
| rs2252430 | 36 | 6 | 36211899 | 127 | MAPK13 | 5603 |
| rs2071863 | 36 | 6 | 36215150 | 127 | MAPK13 | 5603 |
| rs13212041 | 36 | 6 | 78227843 | 127 | HTR1B | 3351 |
| rs6297 | 36 | 6 | 78228660 | 127 | HTR1B | 3351 |
| rs6296 | 36 | 6 | 78228979 | 127 | HTR1B | 3351 |
| rs6298 | 36 | 6 | 78229711 | 127 | HTR1B | 3351 |
| rs130058 | 36 | 6 | 78230000 | 127 | HTR1B | 3351 |
| rs4140535 | 36 | 6 | 78231771 | 127 | HTR1B | 3351 |
| rs2226183 | 36 | 6 | 78233257 | 127 | HTR1B | 3351 |
| rs1213369 | 36 | 6 | 78234976 | 127 | HTR1B | 3351 |
| rs1213370 | 36 | 6 | 78235516 | 127 | HTR1B | 3351 |
| rs9400317 | 36 | 6 | 110114340 | 127 | FIG4 | 221264 |

APPENDIX 1-continued

SNPs genotyped

| SNP ID | Genome Build Version | Chr | Position | dbSNP Version | Gene Symbol | Gene ID |
|---|---|---|---|---|---|---|
| rs4947012 | 36 | 6 | 110118967 | 127 | FIG4 | 221264 |
| rs3823234 | 36 | 6 | 110130366 | 127 | FIG4 | 9896 |
| rs9398215 | 36 | 6 | 110146535 | 127 | FIG4 | 9896 |
| rs4947015 | 36 | 6 | 110159208 | 127 | FIG4 | 9896 |
| rs6568602 | 36 | 6 | 110159969 | 127 | FIG4 | 9896 |
| rs11964533 | 36 | 6 | 110165693 | 127 | FIG4 | 9896 |
| rs2295837 | 36 | 6 | 110171621 | 127 | FIG4 | 9896 |
| rs17612758 | 36 | 6 | 110172123 | 127 | FIG4 | 9896 |
| rs13191444 | 36 | 6 | 110190757 | 127 | FIG4 | 9896 |
| rs17613127 | 36 | 6 | 110205619 | 127 | FIG4 | 9896 |
| rs11153219 | 36 | 6 | 110209321 | 127 | FIG4 | 9896 |
| rs10499054 | 36 | 6 | 110212927 | 127 | FIG4 | 9896 |
| rs9885672 | 36 | 6 | 110214210 | 127 | FIG4 | 9896 |
| rs4499962 | 36 | 6 | 110225279 | 127 | FIG4 | 9896 |
| rs4473902 | 36 | 6 | 110226960 | 127 | FIG4 | 9896 |
| rs4495300 | 36 | 6 | 110231221 | 127 | FIG4 | 9896 |
| rs13220781 | 36 | 6 | 110233086 | 127 | FIG4 | 9896 |
| rs17070984 | 36 | 6 | 110233524 | 127 | FIG4 | 9896 |
| rs9398218 | 36 | 6 | 110252996 | 127 | FIG4 | 9896 |
| rs3757070 | 36 | 6 | 153111414 | 127 | VIP | 7432 |
| rs12212849 | 36 | 6 | 153111896 | 127 | VIP | 7432 |
| rs1407267 | 36 | 6 | 153112144 | 127 | VIP | 7432 |
| rs3823082 | 36 | 6 | 153116015 | 127 | VIP | 7432 |
| rs12201030 | 36 | 6 | 153118482 | 127 | VIP | 7432 |
| rs688136 | 36 | 6 | 153121754 | 127 | VIP | 7432 |
| rs664368 | 36 | 6 | 153125119 | 127 | VIP | 7432 |
| rs671330 | 36 | 6 | 153126927 | 127 | VIP | 7432 |
| rs6912029 | 36 | 6 | 154402201 | 127 | OPRM1 | 4988 |
| rs1799971 | 36 | 6 | 154402490 | 127 | OPRM1 | 4988 |
| rs557748 | 36 | 6 | 154405995 | 127 | OPRM1 | 4988 |
| rs4870266 | 36 | 6 | 154410691 | 127 | OPRM1 | 4988 |
| rs610231 | 36 | 6 | 154420170 | 127 | OPRM1 | 4988 |
| rs3823010 | 36 | 6 | 154420845 | 127 | OPRM1 | 4988 |
| rs589046 | 36 | 6 | 154434831 | 127 | OPRM1 | 4988 |
| rs483021 | 36 | 6 | 154439021 | 127 | OPRM1 | 4988 |
| rs563649 | 36 | 6 | 154449660 | 127 | OPRM1 | 4988 |
| rs2075572 | 36 | 6 | 154453697 | 127 | OPRM1 | 4988 |
| rs510587 | 36 | 6 | 154455121 | 127 | OPRM1 | 4988 |
| rs540825 | 36 | 6 | 154456139 | 127 | OPRM1 | 4988 |
| rs675026 | 36 | 6 | 154456256 | 127 | OPRM1 | 4988 |
| rs562859 | 36 | 6 | 154456266 | 127 | OPRM1 | 4988 |
| rs3798683 | 36 | 6 | 154460107 | 127 | OPRM1 | 4988 |
| rs599548 | 36 | 6 | 154460254 | 127 | OPRM1 | 4988 |
| rs511420 | 36 | 6 | 154465725 | 127 | OPRM1 | 4988 |
| rs512053 | 36 | 6 | 154481209 | 127 | OPRM1 | 4988 |
| rs10485058 | 36 | 6 | 154486907 | 127 | OPRM1 | 4988 |
| rs538174 | 36 | 6 | 154494229 | 127 | OPRM1 | 4988 |
| rs13193545 | 36 | 6 | 154503514 | 127 | OPRM1 | 26034 |
| rs9397687 | 36 | 6 | 154503778 | 127 | OPRM1 | 26034 |
| rs518596 | 36 | 6 | 154504070 | 127 | OPRM1 | 26034 |
| rs10223804 | 36 | 6 | 154504084 | 127 | OPRM1 | 26034 |
| rs483481 | 36 | 6 | 154505660 | 127 | OPRM1 | 26034 |
| rs569284 | 36 | 6 | 154506022 | 127 | OPRM1 | 26034 |
| rs6904856 | 36 | 6 | 154508824 | 127 | OPRM1 | 26034 |
| rs9371778 | 36 | 6 | 154515517 | 127 | OPRM1 | 26034 |
| rs9383693 | 36 | 6 | 154516563 | 127 | OPRM1 | 26034 |
| rs17277929 | 36 | 6 | 154519605 | 127 | OPRM1 | 26034 |
| rs2236257 | 36 | 6 | 154520259 | 127 | OPRM1 | 26034 |
| rs12199124 | 36 | 6 | 154527332 | 127 | OPRM1 | 26034 |
| rs7755635 | 36 | 6 | 154528053 | 127 | OPRM1 | 26034 |
| rs9397692 | 36 | 6 | 154529007 | 127 | OPRM1 | 26034 |
| rs2281617 | 36 | 6 | 154529113 | 127 | OPRM1 | 26034 |
| rs6939625 | 36 | 6 | 154529487 | 127 | OPRM1 | 26034 |
| rs12207621 | 36 | 6 | 154543952 | 127 | OPRM1 | 26034 |
| rs9479779 | 36 | 6 | 154544380 | 127 | OPRM1 | 26034 |
| rs1040822 | 36 | 6 | 154560330 | 127 | OPRM1 | 26034 |
| rs17085185 | 36 | 6 | 154561292 | 127 | OPRM1 | 26034 |
| rs9322451 | 36 | 6 | 154564353 | 127 | OPRM1 | 26034 |
| rs950808 | 36 | 6 | 154564963 | 127 | OPRM1 | 26034 |
| rs9397182 | 36 | 6 | 154568777 | 127 | OPRM1 | 26034 |
| rs9479791 | 36 | 6 | 154571206 | 127 | OPRM1 | 26034 |
| rs6913456 | 36 | 6 | 154572672 | 127 | OPRM1 | 26034 |
| rs6921548 | 36 | 6 | 154582015 | 127 | OPRM1 | 26034 |
| rs12212773 | 36 | 6 | 154592810 | 127 | OPRM1 | 26034 |

APPENDIX 1-continued

SNPs genotyped

| SNP ID | Genome Build Version | Chr | Position | dbSNP Version | Gene Symbol | Gene ID |
|---|---|---|---|---|---|---|
| rs9371781 | 36 | 6 | 154593899 | 127 | OPRM1 | 26034 |
| rs17292684 | 36 | 6 | 154596299 | 127 | OPRM1 | 26034 |
| rs6935927 | 36 | 6 | 154602029 | 127 | OPRM1 | 26034 |
| rs11155954 | 36 | 6 | 154608434 | 127 | OPRM1 | 26034 |
| rs9397698 | 36 | 6 | 154609054 | 127 | OPRM1 | 26034 |
| rs17214592 | 36 | 6 | 154612099 | 127 | OPRM1 | 26034 |
| rs7738233 | 36 | 6 | 154612240 | 127 | OPRM1 | 26034 |
| rs1474644 | 36 | 6 | 170690820 | 127 | PSMB1 | 5689 |
| rs2056970 | 36 | 6 | 170691401 | 127 | PSMB1 | 5689 |
| rs1474642 | 36 | 6 | 170694486 | 127 | PSMB1 | 5689 |
| rs9356664 | 36 | 6 | 170702320 | 127 | PSMB1 | 5689 |
| rs2206286 | 36 | 6 | 170703760 | 127 | PSMB1 | 5689 |
| rs12210583 | 36 | 6 | 170703954 | 127 | PSMB1 | 5689 |
| rs12717 | 36 | 6 | 170704225 | 127 | PSMB1 | 5689 |
| rs12210836 | 36 | 6 | 170704381 | 127 | PSMB1 | 5689 |
| rs2179373 | 36 | 6 | 170705298 | 127 | PSMB1 | 6908 |
| rs6456230 | 36 | 6 | 170709501 | 127 | PSMB1 | 6908 |
| rs852432 | 36 | 7 | 5529266 | 127 | ACTB | 60 |
| rs13447427 | 36 | 7 | 5531960 | 127 | ACTB | 60 |
| rs852392 | 36 | 7 | 5538658 | 127 | ACTB | 60 |
| rs6463491 | 36 | 7 | 5545045 | 127 | ACTB | 60 |
| rs12700386 | 36 | 7 | 22729534 | 127 | IL6 | 3569 |
| rs2069824 | 36 | 7 | 22731757 | 127 | IL6 | 3569 |
| rs1474348 | 36 | 7 | 22734433 | 127 | IL6 | 3569 |
| rs1524107 | 36 | 7 | 22734744 | 127 | IL6 | 3569 |
| rs2069840 | 36 | 7 | 22735097 | 127 | IL6 | 3569 |
| rs2069860 | 36 | 7 | 22737563 | 127 | IL6 | 3569 |
| rs2069849 | 36 | 7 | 22737681 | 127 | IL6 | 3569 |
| rs2069861 | 36 | 7 | 22738179 | 127 | IL6 | 3569 |
| rs10242595 | 36 | 7 | 22740756 | 127 | IL6 | 3569 |
| rs11766273 | 36 | 7 | 22742188 | 127 | IL6 | 3569 |
| rs7800861 | 36 | 7 | 24287185 | 127 | NPY | 4852 |
| rs12700524 | 36 | 7 | 24287939 | 127 | NPY | 4852 |
| rs3857723 | 36 | 7 | 24288352 | 127 | NPY | 4852 |
| rs16139 | 36 | 7 | 24291404 | 127 | NPY | 4852 |
| rs9785023 | 36 | 7 | 24291534 | 127 | NPY | 4852 |
| rs16135 | 36 | 7 | 24294445 | 127 | NPY | 4852 |
| rs5574 | 36 | 7 | 24295658 | 127 | NPY | 4852 |
| rs16475 | 36 | 7 | 24298011 | 127 | NPY | 4852 |
| rs16473 | 36 | 7 | 24300176 | 127 | NPY | 4852 |
| rs16472 | 36 | 7 | 24300594 | 127 | NPY | 4852 |
| rs2529439 | 36 | 7 | 30610273 | 127 | GARS | 2617 |
| rs3807632 | 36 | 7 | 30611474 | 127 | GARS | 2617 |
| rs728539 | 36 | 7 | 30614576 | 127 | GARS | 2617 |
| rs1986756 | 36 | 7 | 30618463 | 127 | GARS | 2617 |
| rs10951271 | 36 | 7 | 30627463 | 127 | GARS | 2617 |
| rs2709778 | 36 | 7 | 30633958 | 127 | GARS | 2617 |
| rs1859644 | 36 | 7 | 30641184 | 127 | GARS | 2617 |
| rs2908200 | 36 | 7 | 75766731 | 127 | HSPB1 | 3315 |
| rs2868370 | 36 | 7 | 75768736 | 127 | HSPB1 | 3315 |
| rs7459185 | 36 | 7 | 75772576 | 127 | HSPB1 | 3315 |
| rs17773605 | 36 | 7 | 94762474 | 127 | PON1 | 55607 |
| rs8491 | 36 | 7 | 94763550 | 127 | PON1 | 55607 |
| rs3735590 | 36 | 7 | 94765431 | 127 | PON1 | 5444 |
| rs854551 | 36 | 7 | 94765613 | 127 | PON1 | 5444 |
| rs854552 | 36 | 7 | 94765860 | 127 | PON1 | 5444 |
| rs854555 | 36 | 7 | 94768327 | 127 | PON1 | 5444 |
| rs3917550 | 36 | 7 | 94772509 | 127 | PON1 | 5444 |
| rs3917594 | 36 | 7 | 94775375 | 127 | PON1 | 5444 |
| rs662 | 36 | 7 | 94775382 | 127 | PON1 | 5444 |
| rs3917541 | 36 | 7 | 94775560 | 127 | PON1 | 5444 |
| rs2299257 | 36 | 7 | 94780701 | 127 | PON1 | 5444 |
| rs854561 | 36 | 7 | 94784953 | 127 | PON1 | 5444 |
| rs2074351 | 36 | 7 | 94785735 | 127 | PON1 | 5444 |
| rs2272365 | 36 | 7 | 94786562 | 127 | PON1 | 5444 |
| rs3917490 | 36 | 7 | 94786777 | 127 | PON1 | 5444 |
| rs2049649 | 36 | 7 | 94787265 | 127 | PON1 | 5444 |
| rs2299260 | 36 | 7 | 94787473 | 127 | PON1 | 5444 |
| rs2299261 | 36 | 7 | 94787599 | 127 | PON1 | 5444 |
| rs854568 | 36 | 7 | 94787737 | 127 | PON1 | 5444 |
| rs2299262 | 36 | 7 | 94787864 | 127 | PON1 | 5444 |
| rs854569 | 36 | 7 | 94787991 | 127 | PON1 | 5444 |
| rs2237583 | 36 | 7 | 94788113 | 127 | PON1 | 5444 |
| rs2237584 | 36 | 7 | 94788773 | 127 | PON1 | 5444 |

APPENDIX 1-continued

SNPs genotyped

| SNP ID | Genome Build Version | Chr | Position | dbSNP Version | Gene Symbol | Gene ID |
|---|---|---|---|---|---|---|
| rs854572 | 36 | 7 | 94792632 | 127 | PON1 | 5444 |
| rs854573 | 36 | 7 | 94792799 | 127 | PON1 | 5444 |
| rs17166818 | 36 | 7 | 94796564 | 127 | PON1 | 5444 |
| rs13228784 | 36 | 7 | 94798761 | 127 | PON1 | 5444 |
| rs4729205 | 36 | 7 | 95237165 | 127 | DYNC1I1 | 1780 |
| rs983350 | 36 | 7 | 95242854 | 127 | DYNC1I1 | 1780 |
| rs7798435 | 36 | 7 | 95250879 | 127 | DYNC1I1 | 1780 |
| rs1478983 | 36 | 7 | 95250893 | 127 | DYNC1I1 | 1780 |
| rs4729206 | 36 | 7 | 95258613 | 127 | DYNC1I1 | 1780 |
| rs6962547 | 36 | 7 | 95258858 | 127 | DYNC1I1 | 1780 |
| rs2706888 | 36 | 7 | 95262393 | 127 | DYNC1I1 | 1780 |
| rs11767450 | 36 | 7 | 95274371 | 127 | DYNC1I1 | 1780 |
| rs940424 | 36 | 7 | 95274841 | 127 | DYNC1I1 | 1780 |
| rs1922332 | 36 | 7 | 95279286 | 127 | DYNC1I1 | 1780 |
| rs2690294 | 36 | 7 | 95283196 | 127 | DYNC1I1 | 1780 |
| rs1227514 | 36 | 7 | 95298252 | 127 | DYNC1I1 | 1780 |
| rs11769486 | 36 | 7 | 95332678 | 127 | DYNC1I1 | 1780 |
| rs3757697 | 36 | 7 | 95337170 | 127 | DYNC1I1 | 1780 |
| rs6967902 | 36 | 7 | 95347742 | 127 | DYNC1I1 | 1780 |
| rs10249566 | 36 | 7 | 95350562 | 127 | DYNC1I1 | 1780 |
| rs4727329 | 36 | 7 | 95360863 | 127 | DYNC1I1 | 1780 |
| rs7809646 | 36 | 7 | 95364235 | 127 | DYNC1I1 | 1780 |
| rs984862 | 36 | 7 | 95367092 | 127 | DYNC1I1 | 1780 |
| rs4357216 | 36 | 7 | 95369751 | 127 | DYNC1I1 | 1780 |
| rs4729224 | 36 | 7 | 95384055 | 127 | DYNC1I1 | 1780 |
| rs10243540 | 36 | 7 | 95384186 | 127 | DYNC1I1 | 1780 |
| rs6952893 | 36 | 7 | 95384689 | 127 | DYNC1I1 | 1780 |
| rs319328 | 36 | 7 | 95387648 | 127 | DYNC1I1 | 1780 |
| rs319314 | 36 | 7 | 95394566 | 127 | DYNC1I1 | 1780 |
| rs6950190 | 36 | 7 | 95396294 | 127 | DYNC1I1 | 1780 |
| rs2860011 | 36 | 7 | 95397030 | 127 | DYNC1I1 | 1780 |
| rs319312 | 36 | 7 | 95397227 | 127 | DYNC1I1 | 1780 |
| rs17775819 | 36 | 7 | 95397951 | 127 | DYNC1I1 | 1780 |
| rs1488516 | 36 | 7 | 95401327 | 127 | DYNC1I1 | 1780 |
| rs2239954 | 36 | 7 | 95415377 | 127 | DYNC1I1 | 1780 |
| rs319345 | 36 | 7 | 95415761 | 127 | DYNC1I1 | 1780 |
| rs12155036 | 36 | 7 | 95416050 | 127 | DYNC1I1 | 1780 |
| rs4729228 | 36 | 7 | 95419185 | 127 | DYNC1I1 | 1780 |
| rs13237676 | 36 | 7 | 95430998 | 127 | DYNC1I1 | 1780 |
| rs1548399 | 36 | 7 | 95435367 | 127 | DYNC1I1 | 1780 |
| rs12537028 | 36 | 7 | 95437211 | 127 | DYNC1I1 | 1780 |
| rs13231718 | 36 | 7 | 95438304 | 127 | DYNC1I1 | 1780 |
| rs319301 | 36 | 7 | 95442487 | 127 | DYNC1I1 | 1780 |
| rs1488517 | 36 | 7 | 95446689 | 127 | DYNC1I1 | 1780 |
| rs17705297 | 36 | 7 | 95447233 | 127 | DYNC1I1 | 1780 |
| rs319322 | 36 | 7 | 95447893 | 127 | DYNC1I1 | 1780 |
| rs2073984 | 36 | 7 | 95452403 | 127 | DYNC1I1 | 1780 |
| rs17705339 | 36 | 7 | 95454245 | 127 | DYNC1I1 | 1780 |
| rs1685818 | 36 | 7 | 95454893 | 127 | DYNC1I1 | 1780 |
| rs2299269 | 36 | 7 | 95457313 | 127 | DYNC1I1 | 1780 |
| rs12704828 | 36 | 7 | 95461843 | 127 | DYNC1I1 | 1780 |
| rs1488514 | 36 | 7 | 95465707 | 127 | DYNC1I1 | 1780 |
| rs756860 | 36 | 7 | 95467014 | 127 | DYNC1I1 | 1780 |
| rs81018 | 36 | 7 | 95467762 | 127 | DYNC1I1 | 1780 |
| rs4727332 | 36 | 7 | 95468537 | 127 | DYNC1I1 | 1780 |
| rs1488515 | 36 | 7 | 95469132 | 127 | DYNC1I1 | 1780 |
| rs739513 | 36 | 7 | 95473084 | 127 | DYNC1I1 | 1780 |
| rs7780260 | 36 | 7 | 95478193 | 127 | DYNC1I1 | 1780 |
| rs13241648 | 36 | 7 | 95483235 | 127 | DYNC1I1 | 1780 |
| rs319319 | 36 | 7 | 95484060 | 127 | DYNC1I1 | 1780 |
| rs319318 | 36 | 7 | 95486023 | 127 | DYNC1I1 | 1780 |
| rs1994506 | 36 | 7 | 95486102 | 127 | DYNC1I1 | 1780 |
| rs319290 | 36 | 7 | 95491815 | 127 | DYNC1I1 | 1780 |
| rs7782220 | 36 | 7 | 95496227 | 127 | DYNC1I1 | 1780 |
| rs2214097 | 36 | 7 | 95497816 | 127 | DYNC1I1 | 1780 |
| rs2299278 | 36 | 7 | 95504398 | 127 | DYNC1I1 | 1780 |
| rs1048666 | 36 | 7 | 95506600 | 127 | DYNC1I1 | 1780 |
| rs13227274 | 36 | 7 | 95533741 | 127 | DYNC1I1 | 1780 |
| rs7796347 | 36 | 7 | 95539385 | 127 | DYNC1I1 | 1780 |
| rs42084 | 36 | 7 | 95547259 | 127 | DYNC1I1 | 1780 |
| rs2299287 | 36 | 7 | 95550618 | 127 | DYNC1I1 | 1780 |
| rs42065 | 36 | 7 | 95556515 | 127 | DYNC1I1 | 1780 |
| rs452 | 36 | 7 | 95559946 | 127 | DYNC1I1 | 1780 |
| rs17776584 | 36 | 7 | 95563294 | 127 | DYNC1I1 | 1780 |

APPENDIX 1-continued

SNPs genotyped

| SNP ID | Genome Build Version | Chr | Position | dbSNP Version | Gene Symbol | Gene ID |
|---|---|---|---|---|---|---|
| rs916758 | 36 | 7 | 95563872 | 127 | DYNC1I1 | 1780 |
| rs7794344 | 36 | 7 | 95564950 | 127 | DYNC1I1 | 1780 |
| rs6966540 | 36 | 7 | 95565903 | 127 | DYNC1I1 | 1780 |
| rs12670075 | 36 | 7 | 95569095 | 127 | DYNC1I1 | 1780 |
| rs6956305 | 36 | 7 | 99079246 | 127 | CYP3A5 | 1577 |
| rs15524 | 36 | 7 | 99083850 | 127 | CYP3A5 | 1577 |
| rs4646450 | 36 | 7 | 99104254 | 127 | CYP3A5 | 1577 |
| rs776746 | 36 | 7 | 99108475 | 127 | CYP3A5 | 1577 |
| rs12333983 | 36 | 7 | 99192050 | 127 | CYP3A4 | 1576 |
| rs4986910 | 36 | 7 | 99196460 | 127 | CYP3A4 | 1576 |
| rs4646437 | 36 | 7 | 99203019 | 127 | CYP3A4 | 1576 |
| rs2740574 | 36 | 7 | 99220032 | 127 | CYP3A4 | 1576 |
| rs2571992 | 36 | 7 | 99357852 | 127 | GJE1 | 349149 |
| rs2527908 | 36 | 7 | 99358499 | 127 | GJE1 | 349149 |
| rs11977827 | 36 | 7 | 99364252 | 127 | GJE1 | 349149 |
| rs11974610 | 36 | 7 | 99365913 | 127 | GJE1 | 349149 |
| rs2525549 | 36 | 7 | 99371047 | 127 | GJE1 | 349149 |
| rs41796 | 36 | 7 | 116297475 | 127 | CAPZA2 | 830 |
| rs12537143 | 36 | 7 | 116304161 | 127 | CAPZA2 | 830 |
| rs4808 | 36 | 7 | 116315476 | 127 | CAPZA2 | 830 |
| rs3173936 | 36 | 7 | 116345175 | 127 | CAPZA2 | 830 |
| rs1049618 | 36 | 7 | 116345952 | 127 | CAPZA2 | 830 |
| rs1978105 | 36 | 7 | 116350167 | 127 | CAPZA2 | 830 |
| rs887574 | 36 | 7 | 116703248 | 127 | WNT2 | 7472 |
| rs887575 | 36 | 7 | 116703464 | 127 | WNT2 | 7472 |
| rs4730775 | 36 | 7 | 116704354 | 127 | WNT2 | 7472 |
| rs2024233 | 36 | 7 | 116704663 | 127 | WNT2 | 7472 |
| rs2228946 | 36 | 7 | 116705321 | 127 | WNT2 | 7472 |
| rs733153 | 36 | 7 | 116706028 | 127 | WNT2 | 7472 |
| rs2896218 | 36 | 7 | 116707214 | 127 | WNT2 | 7472 |
| rs3779547 | 36 | 7 | 116718198 | 127 | WNT2 | 7472 |
| rs10227271 | 36 | 7 | 116727284 | 127 | WNT2 | 7472 |
| rs39306 | 36 | 7 | 116728472 | 127 | WNT2 | 7472 |
| rs2285544 | 36 | 7 | 116731519 | 127 | WNT2 | 7472 |
| rs1989836 | 36 | 7 | 116734432 | 127 | WNT2 | 7472 |
| rs2285545 | 36 | 7 | 116735407 | 127 | WNT2 | 7472 |
| rs39312 | 36 | 7 | 116742021 | 127 | WNT2 | 7472 |
| rs739517 | 36 | 7 | 116742935 | 127 | WNT2 | 7472 |
| rs39321 | 36 | 7 | 116756145 | 127 | WNT2 | 7472 |
| rs6961545 | 36 | 7 | 116759067 | 127 | WNT2 | 7472 |
| rs3757552 | 36 | 7 | 120751201 | 127 | WNT16 | 51384 |
| rs2908004 | 36 | 7 | 120757005 | 127 | WNT16 | 51384 |
| rs3801387 | 36 | 7 | 120762001 | 127 | WNT16 | 51384 |
| rs2707471 | 36 | 7 | 120763913 | 127 | WNT16 | 51384 |
| rs3801385 | 36 | 7 | 120764779 | 127 | WNT16 | 51384 |
| rs13225343 | 36 | 7 | 133772980 | 127 | AKR1B1 | 231 |
| rs10252030 | 36 | 7 | 133774414 | 127 | AKR1B1 | 231 |
| rs17167841 | 36 | 7 | 133775472 | 127 | AKR1B1 | 231 |
| rs2734649 | 36 | 7 | 133786291 | 127 | AKR1B1 | 231 |
| rs1790998 | 36 | 7 | 133788920 | 127 | AKR1B1 | 231 |
| rs17188118 | 36 | 7 | 133792608 | 127 | AKR1B1 | 231 |
| rs5053 | 36 | 7 | 133794403 | 127 | AKR1B1 | 231 |
| rs1708403 | 36 | 7 | 133802904 | 127 | AKR1B1 | 231 |
| rs11489454 | 36 | 7 | 149570491 | 127 | ARP11 | 653857 |
| rs2530976 | 36 | 7 | 149586818 | 127 | ARP11 | 653857 |
| rs17134508 | 36 | 7 | 149601156 | 127 | ARP11 | 653857 |
| rs17835738 | 36 | 7 | 149623031 | 127 | ARP11 | 653857 |
| rs2976441 | 36 | 8 | 24863702 | 127 | NEFL | 4747 |
| rs2979704 | 36 | 8 | 24864984 | 127 | NEFL | 4747 |
| rs17052849 | 36 | 8 | 24865862 | 127 | NEFL | 4747 |
| rs1059111 | 36 | 8 | 24866005 | 127 | NEFL | 4747 |
| rs2979687 | 36 | 8 | 24870320 | 127 | NEFL | 4747 |
| rs3757985 | 36 | 8 | 24872354 | 127 | NEFL | 4747 |
| rs17830286 | 36 | 8 | 24873062 | 127 | NEFL | 4747 |
| rs17830392 | 36 | 8 | 24874818 | 127 | NEFL | 4747 |
| rs2976423 | 36 | 8 | 24877933 | 127 | NEFL | 4747 |
| rs2614082 | 36 | 8 | 28226449 | 127 | PNOC | 5368 |
| rs2722894 | 36 | 8 | 28227458 | 127 | PNOC | 5368 |
| rs12677384 | 36 | 8 | 28228417 | 127 | PNOC | 5368 |
| rs3808366 | 36 | 8 | 28229670 | 127 | PNOC | 5368 |
| rs17058952 | 36 | 8 | 28230273 | 127 | PNOC | 5368 |
| rs1563945 | 36 | 8 | 28230805 | 127 | PNOC | 5368 |
| rs11779594 | 36 | 8 | 28237674 | 127 | PNOC | 5368 |
| rs7840629 | 36 | 8 | 28238368 | 127 | PNOC | 5368 |

APPENDIX 1-continued

SNPs genotyped

| SNP ID | Genome Build Version | Chr | Position | dbSNP Version | Gene Symbol | Gene ID |
|---|---|---|---|---|---|---|
| rs6989655 | 36 | 8 | 28242891 | 127 | PNOC | 5368 |
| rs2614108 | 36 | 8 | 28244552 | 127 | PNOC | 5368 |
| rs189509 | 36 | 8 | 28247625 | 127 | PNOC | 5368 |
| rs3735736 | 36 | 8 | 28250016 | 127 | PNOC | 5368 |
| rs351784 | 36 | 8 | 28253666 | 127 | PNOC | 5368 |
| rs17058985 | 36 | 8 | 28254863 | 127 | PNOC | 5368 |
| rs904053 | 36 | 8 | 28258855 | 127 | PNOC | 55893 |
| rs351779 | 36 | 8 | 28260183 | 127 | PNOC | 55893 |
| rs4733400 | 36 | 8 | 30132056 | 127 | DCTN6 | 10671 |
| rs7829853 | 36 | 8 | 30143082 | 127 | DCTN6 | 10671 |
| rs16876610 | 36 | 8 | 30149412 | 127 | DCTN6 | 10671 |
| rs2242457 | 36 | 8 | 30162200 | 127 | DCTN6 | 10671 |
| rs7839445 | 36 | 8 | 54303000 | 127 | OPRK1 | 4986 |
| rs7843295 | 36 | 8 | 54303951 | 127 | OPRK1 | 4986 |
| rs963549 | 36 | 8 | 54304377 | 127 | OPRK1 | 4986 |
| rs16918875 | 36 | 8 | 54304707 | 127 | OPRK1 | 4986 |
| rs702764 | 36 | 8 | 54304710 | 127 | OPRK1 | 4986 |
| rs16918909 | 36 | 8 | 54312587 | 127 | OPRK1 | 4986 |
| rs1365098 | 36 | 8 | 54315236 | 127 | OPRK1 | 4986 |
| rs6473799 | 36 | 8 | 54315676 | 127 | OPRK1 | 4986 |
| rs17272364 | 36 | 8 | 54318360 | 127 | OPRK1 | 4986 |
| rs7836120 | 36 | 8 | 54320092 | 127 | OPRK1 | 4986 |
| rs6985606 | 36 | 8 | 54323669 | 127 | OPRK1 | 4986 |
| rs12677359 | 36 | 8 | 54333799 | 127 | OPRK1 | 4986 |
| rs4738450 | 36 | 8 | 75426887 | 127 | GDAP1 | 54332 |
| rs6472842 | 36 | 8 | 75441012 | 127 | GDAP1 | 54332 |
| rs10504580 | 36 | 8 | 75441371 | 127 | GDAP1 | 54332 |
| rs7844272 | 36 | 8 | 134314989 | 127 | NDRG1 | 10397 |
| rs2929975 | 36 | 8 | 134315900 | 127 | NDRG1 | 10397 |
| rs1049697 | 36 | 8 | 134319347 | 127 | NDRG1 | 10397 |
| rs3779945 | 36 | 8 | 134321914 | 127 | NDRG1 | 10397 |
| rs17641864 | 36 | 8 | 134322616 | 127 | NDRG1 | 10397 |
| rs2929978 | 36 | 8 | 134323979 | 127 | NDRG1 | 10397 |
| rs11784952 | 36 | 8 | 134324460 | 127 | NDRG1 | 10397 |
| rs2977557 | 36 | 8 | 134326285 | 127 | NDRG1 | 10397 |
| rs2233339 | 36 | 8 | 134327893 | 127 | NDRG1 | 10397 |
| rs2233336 | 36 | 8 | 134330130 | 127 | NDRG1 | 10397 |
| rs10956698 | 36 | 8 | 134332521 | 127 | NDRG1 | 10397 |
| rs3779939 | 36 | 8 | 134332635 | 127 | NDRG1 | 10397 |
| rs7018287 | 36 | 8 | 134333236 | 127 | NDRG1 | 10397 |
| rs3779936 | 36 | 8 | 134334930 | 127 | NDRG1 | 10397 |
| rs2272650 | 36 | 8 | 134336152 | 127 | NDRG1 | 10397 |
| rs1011460 | 36 | 8 | 134339120 | 127 | NDRG1 | 10397 |
| rs2929984 | 36 | 8 | 134340069 | 127 | NDRG1 | 10397 |
| rs2233329 | 36 | 8 | 134340511 | 127 | NDRG1 | 10397 |
| rs2233327 | 36 | 8 | 134340688 | 127 | NDRG1 | 10397 |
| rs7839335 | 36 | 8 | 134340830 | 127 | NDRG1 | 10397 |
| rs2929985 | 36 | 8 | 134341389 | 127 | NDRG1 | 10397 |
| rs7825728 | 36 | 8 | 134341479 | 127 | NDRG1 | 10397 |
| rs4736442 | 36 | 8 | 134343050 | 127 | NDRG1 | 10397 |
| rs2929989 | 36 | 8 | 134346995 | 127 | NDRG1 | 10397 |
| rs3779932 | 36 | 8 | 134348162 | 127 | NDRG1 | 10397 |
| rs2929994 | 36 | 8 | 134354866 | 127 | NDRG1 | 10397 |
| rs2929995 | 36 | 8 | 134354989 | 127 | NDRG1 | 10397 |
| rs10956699 | 36 | 8 | 134357765 | 127 | NDRG1 | 10397 |
| rs4504614 | 36 | 8 | 134367674 | 127 | NDRG1 | 10397 |
| rs2004066 | 36 | 8 | 134368101 | 127 | NDRG1 | 10397 |
| rs3802254 | 36 | 8 | 134369548 | 127 | NDRG1 | 10397 |
| rs3802253 | 36 | 8 | 134373063 | 127 | NDRG1 | 10397 |
| rs10108354 | 36 | 8 | 134378316 | 127 | NDRG1 | 10397 |
| rs4373502 | 36 | 8 | 134384423 | 127 | NDRG1 | 10397 |
| rs7007149 | 36 | 8 | 134386997 | 127 | NDRG1 | 10397 |
| rs3808870 | 36 | 9 | 34611238 | 127 | DCTN3 | 138715 |
| rs3808869 | 36 | 9 | 34612389 | 127 | DCTN3 | 138715 |
| rs10814129 | 36 | 9 | 34613718 | 127 | DCTN3 | 138715 |
| rs10972175 | 36 | 9 | 34615409 | 127 | DCTN3 | 138715 |
| rs17589865 | 36 | 9 | 93829611 | 127 | SPTLC1 | 10558 |
| rs6479399 | 36 | 9 | 93831953 | 127 | SPTLC1 | 10558 |
| rs7027257 | 36 | 9 | 93840128 | 127 | SPTLC1 | 10558 |
| rs10992216 | 36 | 9 | 93855978 | 127 | SPTLC1 | 10558 |
| rs10820936 | 36 | 9 | 93870795 | 127 | SPTLC1 | 10558 |
| rs17749165 | 36 | 9 | 93900718 | 127 | SPTLC1 | 10558 |
| rs2297568 | 36 | 9 | 93914472 | 127 | SPTLC1 | 10558 |
| rs7858974 | 36 | 9 | 93919931 | 127 | SPTLC1 | 10558 |

APPENDIX 1-continued

SNPs genotyped

| SNP ID | Genome Build Version | Chr | Position | dbSNP Version | Gene Symbol | Gene ID |
|---|---|---|---|---|---|---|
| rs7023075 | 36 | 9 | 93921900 | 127 | SPTLC1 | 10558 |
| rs7024547 | 36 | 9 | 93922309 | 127 | SPTLC1 | 10558 |
| rs7872727 | 36 | 9 | 110665911 | 127 | IKBKAP | 10881 |
| rs10979572 | 36 | 9 | 110668010 | 127 | IKBKAP | 8518 |
| rs3763646 | 36 | 9 | 110671791 | 127 | IKBKAP | 8518 |
| rs2027433 | 36 | 9 | 110677125 | 127 | IKBKAP | 8518 |
| rs4978753 | 36 | 9 | 110677292 | 127 | IKBKAP | 8518 |
| rs10435834 | 36 | 9 | 110680452 | 127 | IKBKAP | 8518 |
| rs10435835 | 36 | 9 | 110680488 | 127 | IKBKAP | 8518 |
| rs1538660 | 36 | 9 | 110681646 | 127 | IKBKAP | 8518 |
| rs7874280 | 36 | 9 | 110682356 | 127 | IKBKAP | 8518 |
| rs2185330 | 36 | 9 | 110683298 | 127 | IKBKAP | 8518 |
| rs3204145 | 36 | 9 | 110691441 | 127 | IKBKAP | 8518 |
| rs1063110 | 36 | 9 | 110693395 | 127 | IKBKAP | 8518 |
| rs947196 | 36 | 9 | 110695753 | 127 | IKBKAP | 8518 |
| rs10979597 | 36 | 9 | 110696853 | 127 | IKBKAP | 8518 |
| rs2275626 | 36 | 9 | 110698842 | 127 | IKBKAP | 8518 |
| rs10979599 | 36 | 9 | 110699098 | 127 | IKBKAP | 8518 |
| rs2230793 | 36 | 9 | 110699304 | 127 | IKBKAP | 8518 |
| rs10979601 | 36 | 9 | 110700672 | 127 | IKBKAP | 8518 |
| rs10979604 | 36 | 9 | 110703575 | 127 | IKBKAP | 8518 |
| rs10979605 | 36 | 9 | 110703614 | 127 | IKBKAP | 8518 |
| rs838827 | 36 | 9 | 110708473 | 127 | IKBKAP | −99 |
| rs1759852 | 36 | 9 | 110709877 | 127 | IKBKAP | 8518 |
| rs725036 | 36 | 9 | 110710078 | 127 | IKBKAP | 8518 |
| rs838824 | 36 | 9 | 110710528 | 127 | IKBKAP | 8518 |
| rs838821 | 36 | 9 | 110712549 | 127 | IKBKAP | 8518 |
| rs11791215 | 36 | 9 | 110713401 | 127 | IKBKAP | 8518 |
| rs2297579 | 36 | 9 | 110713665 | 127 | IKBKAP | 8518 |
| rs754333 | 36 | 9 | 110726717 | 127 | IKBKAP | 8518 |
| rs10979614 | 36 | 9 | 110727627 | 127 | IKBKAP | 8518 |
| rs2275639 | 36 | 9 | 110735980 | 127 | IKBKAP | 8518 |
| rs2275641 | 36 | 9 | 110736210 | 127 | IKBKAP | 8518 |
| rs838819 | 36 | 9 | 110740986 | 127 | IKBKAP | 54942 |
| rs13299328 | 36 | 9 | 110743382 | 127 | IKBKAP | 54942 |
| rs16911652 | 36 | 9 | 124168568 | 127 | PTGS1 | 5742 |
| rs1236913 | 36 | 9 | 124173300 | 127 | PTGS1 | 5742 |
| rs3842787 | 36 | 9 | 124173328 | 127 | PTGS1 | 5742 |
| rs1213266 | 36 | 9 | 124176705 | 127 | PTGS1 | 5742 |
| rs10306135 | 36 | 9 | 124177516 | 127 | PTGS1 | 5742 |
| rs3842788 | 36 | 9 | 124180027 | 127 | PTGS1 | 5742 |
| rs2282169 | 36 | 9 | 124180517 | 127 | PTGS1 | 5742 |
| rs5788 | 36 | 9 | 124183613 | 127 | PTGS1 | 5742 |
| rs5789 | 36 | 9 | 124183794 | 127 | PTGS1 | 5742 |
| rs4273915 | 36 | 9 | 124185150 | 127 | PTGS1 | 5742 |
| rs12238505 | 36 | 9 | 124191705 | 127 | PTGS1 | 5742 |
| rs5794 | 36 | 9 | 124192442 | 127 | PTGS1 | 5742 |
| rs1330811 | 36 | 9 | 126157167 | 127 | PSMB7 | 5695 |
| rs16927388 | 36 | 9 | 126159263 | 127 | PSMB7 | 5695 |
| rs11789637 | 36 | 9 | 126163122 | 127 | PSMB7 | 5695 |
| rs3780199 | 36 | 9 | 126190892 | 127 | PSMB7 | 5695 |
| rs12344916 | 36 | 9 | 126203444 | 127 | PSMB7 | 5695 |
| rs4574 | 36 | 9 | 126216982 | 127 | PSMB7 | 5695 |
| rs12343206 | 36 | 9 | 126223888 | 127 | PSMB7 | 5695 |
| rs599924 | 36 | 9 | 135208412 | 127 | SURF1 | 6834 |
| rs2051680 | 36 | 9 | 135212610 | 127 | SURF1 | 6834 |
| rs2296809 | 36 | 9 | 135216838 | 127 | SURF1 | 6835 |
| rs1059773 | 36 | 9 | 135218686 | 127 | SURF1 | 6836 |
| rs7025557 | 36 | 9 | 139887566 | 127 | CACNA1B | 774 |
| rs11137292 | 36 | 9 | 139900026 | 127 | CACNA1B | 774 |
| rs11137293 | 36 | 9 | 139902442 | 127 | CACNA1B | 774 |
| rs4076712 | 36 | 9 | 139906739 | 127 | CACNA1B | 774 |
| rs11137300 | 36 | 9 | 139921333 | 127 | CACNA1B | 774 |
| rs12236550 | 36 | 9 | 139957854 | 127 | CACNA1B | 774 |
| rs4077399 | 36 | 9 | 139968839 | 127 | CACNA1B | 774 |
| rs12352971 | 36 | 9 | 139986647 | 127 | CACNA1B | 774 |
| rs7028989 | 36 | 9 | 140031491 | 127 | CACNA1B | 774 |
| rs7865887 | 36 | 9 | 140059617 | 127 | CACNA1B | 774 |
| rs11137351 | 36 | 9 | 140059949 | 127 | CACNA1B | 774 |
| rs1547503 | 36 | 9 | 140061934 | 127 | CACNA1B | 774 |
| rs11137363 | 36 | 9 | 140089212 | 127 | CACNA1B | 774 |
| rs936249 | 36 | 9 | 140091136 | 127 | CACNA1B | 774 |
| rs10867105 | 36 | 9 | 140094586 | 127 | CACNA1B | 774 |
| rs7357733 | 36 | 9 | 140123767 | 127 | CACNA1B | 774 |

APPENDIX 1-continued

SNPs genotyped

| SNP ID | Genome Build Version | Chr | Position | dbSNP Version | Gene Symbol | Gene ID |
|---|---|---|---|---|---|---|
| rs1378954 | 36 | 9 | 140125477 | 127 | CACNA1B | 774 |
| rs766374 | 36 | 9 | 140125835 | 127 | CACNA1B | 774 |
| rs2229948 | 36 | 9 | 140128697 | 127 | CACNA1B | 774 |
| rs4876928 | 36 | 9 | 140128836 | 127 | CACNA1B | 774 |
| rs2739257 | 36 | 9 | 140130278 | 127 | CACNA1B | 774 |
| rs2606356 | 36 | 9 | 140131345 | 127 | CACNA1B | 774 |
| rs2606357 | 36 | 9 | 140131402 | 127 | CACNA1B | 774 |
| rs2606358 | 36 | 9 | 140131592 | 127 | CACNA1B | 774 |
| rs2278971 | 36 | 9 | 140134840 | 127 | CACNA1B | 774 |
| rs211376 | 36 | 10 | 32346878 | 127 | KIF5B | 3799 |
| rs2286746 | 36 | 10 | 32348400 | 127 | KIF5B | 3799 |
| rs11594506 | 36 | 10 | 32379798 | 127 | KIF5B | 3799 |
| rs17409410 | 36 | 10 | 32383111 | 127 | KIF5B | 3799 |
| rs11101312 | 36 | 10 | 49277756 | 127 | MAPK8 | 5599 |
| rs10857561 | 36 | 10 | 49278644 | 127 | MAPK8 | 5599 |
| rs17698002 | 36 | 10 | 49279184 | 127 | MAPK8 | 5599 |
| rs7075976 | 36 | 10 | 49284283 | 127 | MAPK8 | 5599 |
| rs17010447 | 36 | 10 | 49294715 | 127 | MAPK8 | 5599 |
| rs11101318 | 36 | 10 | 49295589 | 127 | MAPK8 | 5599 |
| rs2289805 | 36 | 10 | 49297918 | 127 | MAPK8 | 5599 |
| rs17780725 | 36 | 10 | 49300893 | 127 | MAPK8 | 5599 |
| rs1509964 | 36 | 10 | 64237370 | 127 | EGR2 | 84890 |
| rs1509963 | 36 | 10 | 64240417 | 127 | EGR2 | 1959 |
| rs224277 | 36 | 10 | 64250067 | 127 | EGR2 | 1959 |
| rs10995317 | 36 | 10 | 64252772 | 127 | EGR2 | 1959 |
| rs224285 | 36 | 10 | 64254816 | 127 | EGR2 | 1959 |
| rs3793772 | 36 | 10 | 102212815 | 127 | WNT8B | 7479 |
| rs3793771 | 36 | 10 | 102212947 | 127 | WNT8B | 7479 |
| rs2970 | 36 | 10 | 102236502 | 127 | WNT8B | 25956 |
| rs3740409 | 36 | 10 | 104226635 | 127 | ACTR1A | 79847 |
| rs5870 | 36 | 10 | 104229090 | 127 | ACTR1A | 10121 |
| rs13287 | 36 | 10 | 104230428 | 127 | ACTR1A | 10121 |
| rs17709610 | 36 | 10 | 104240268 | 127 | ACTR1A | 10121 |
| rs3842748 | 36 | 11 | 2137971 | 127 | TH | 3630 |
| rs2070762 | 36 | 11 | 2142911 | 127 | TH | 7054 |
| rs6356 | 36 | 11 | 2147527 | 127 | TH | 7054 |
| rs10840490 | 36 | 11 | 2150393 | 127 | TH | 7054 |
| rs10770141 | 36 | 11 | 2150416 | 127 | TH | 7054 |
| rs10743149 | 36 | 11 | 2150751 | 127 | TH | 7054 |
| rs10840491 | 36 | 11 | 2150966 | 127 | TH | 7054 |
| rs4929966 | 36 | 11 | 2154012 | 127 | TH | 7054 |
| rs11564710 | 36 | 11 | 2156905 | 127 | TH | 7054 |
| rs6578993 | 36 | 11 | 2157739 | 127 | TH | 7054 |
| rs11564709 | 36 | 11 | 2157914 | 127 | TH | 7054 |
| rs1045634 | 36 | 11 | 9757026 | 127 | SBF2 | 81846 |
| rs3829252 | 36 | 11 | 9758027 | 127 | SBF2 | 81846 |
| rs3751000 | 36 | 11 | 9758501 | 127 | SBF2 | 81846 |
| rs634680 | 36 | 11 | 9775465 | 127 | SBF2 | 81846 |
| rs438151 | 36 | 11 | 9781441 | 127 | SBF2 | 81846 |
| rs421752 | 36 | 11 | 9783597 | 127 | SBF2 | 81846 |
| rs11042500 | 36 | 11 | 9787171 | 127 | SBF2 | 81846 |
| rs4910066 | 36 | 11 | 9790979 | 127 | SBF2 | 81846 |
| rs10770067 | 36 | 11 | 9792690 | 127 | SBF2 | 81846 |
| rs4910508 | 36 | 11 | 9804266 | 127 | SBF2 | 81846 |
| rs2403222 | 36 | 11 | 9809066 | 127 | SBF2 | 81846 |
| rs12574508 | 36 | 11 | 9810353 | 127 | SBF2 | 81846 |
| rs7483882 | 36 | 11 | 9817585 | 127 | SBF2 | 81846 |
| rs9645624 | 36 | 11 | 9820503 | 127 | SBF2 | 81846 |
| rs11603291 | 36 | 11 | 9822432 | 127 | SBF2 | 81846 |
| rs11042510 | 36 | 11 | 9825416 | 127 | SBF2 | 81846 |
| rs11042511 | 36 | 11 | 9827198 | 127 | SBF2 | 81846 |
| rs2649049 | 36 | 11 | 9829859 | 127 | SBF2 | 81846 |
| rs360166 | 36 | 11 | 9834085 | 127 | SBF2 | 81846 |
| rs7102464 | 36 | 11 | 9836414 | 127 | SBF2 | 81846 |
| rs780382 | 36 | 11 | 9838051 | 127 | SBF2 | 81846 |
| rs4910067 | 36 | 11 | 9842425 | 127 | SBF2 | 81846 |
| rs1546542 | 36 | 11 | 9857034 | 127 | SBF2 | 81846 |
| rs10500711 | 36 | 11 | 9857911 | 127 | SBF2 | 81846 |
| rs11042524 | 36 | 11 | 9858687 | 127 | SBF2 | 81846 |
| rs17354870 | 36 | 11 | 9860504 | 127 | SBF2 | 81846 |
| rs10840318 | 36 | 11 | 9873179 | 127 | SBF2 | 81846 |
| rs7936793 | 36 | 11 | 9873798 | 127 | SBF2 | 81846 |
| rs17355751 | 36 | 11 | 9877034 | 127 | SBF2 | 81846 |
| rs7130923 | 36 | 11 | 9890931 | 127 | SBF2 | 81846 |

APPENDIX 1-continued

SNPs genotyped

| SNP ID | Genome Build Version | Chr | Position | dbSNP Version | Gene Symbol | Gene ID |
|---|---|---|---|---|---|---|
| rs11042543 | 36 | 11 | 9896394 | 127 | SBF2 | 81846 |
| rs7939451 | 36 | 11 | 9917655 | 127 | SBF2 | 81846 |
| rs10840331 | 36 | 11 | 9929055 | 127 | SBF2 | 81846 |
| rs11042572 | 36 | 11 | 9947929 | 127 | SBF2 | 81846 |
| rs17356792 | 36 | 11 | 9951097 | 127 | SBF2 | 81846 |
| rs7109648 | 36 | 11 | 9953641 | 127 | SBF2 | 81846 |
| rs4910090 | 36 | 11 | 9959866 | 127 | SBF2 | 81846 |
| rs7925889 | 36 | 11 | 10004895 | 127 | SBF2 | 81846 |
| rs17357710 | 36 | 11 | 10004943 | 127 | SBF2 | 81846 |
| rs12360569 | 36 | 11 | 10074011 | 127 | SBF2 | 81846 |
| rs12363292 | 36 | 11 | 10104544 | 127 | SBF2 | 81846 |
| rs11042643 | 36 | 11 | 10120941 | 127 | SBF2 | 81846 |
| rs11602057 | 36 | 11 | 10121032 | 127 | SBF2 | 81846 |
| rs16907561 | 36 | 11 | 10166479 | 127 | SBF2 | 81846 |
| rs11042655 | 36 | 11 | 10170202 | 127 | SBF2 | 81846 |
| rs17294511 | 36 | 11 | 10178648 | 127 | SBF2 | 81846 |
| rs7929332 | 36 | 11 | 10180933 | 127 | SBF2 | 81846 |
| rs7938543 | 36 | 11 | 10186427 | 127 | SBF2 | 81846 |
| rs2920151 | 36 | 11 | 10253243 | 127 | SBF2 | 81846 |
| rs4641466 | 36 | 11 | 10279602 | 127 | SBF2 | 133 |
| rs4930387 | 36 | 11 | 66206481 | 127 | SPTBN2 | 6712 |
| rs623022 | 36 | 11 | 66215556 | 127 | SPTBN2 | 6712 |
| rs639938 | 36 | 11 | 66217103 | 127 | SPTBN2 | 6712 |
| rs532439 | 36 | 11 | 66225608 | 127 | SPTBN2 | 6712 |
| rs615536 | 36 | 11 | 66237840 | 127 | SPTBN2 | 6712 |
| rs10791889 | 36 | 11 | 66250401 | 127 | SPTBN2 | 6712 |
| rs647159 | 36 | 11 | 75570389 | 127 | WNT11 | 7481 |
| rs11236644 | 36 | 11 | 75572655 | 127 | WNT11 | 7481 |
| rs581794 | 36 | 11 | 75572939 | 127 | WNT11 | 7481 |
| rs598143 | 36 | 11 | 75574220 | 127 | WNT11 | 7481 |
| rs12277860 | 36 | 11 | 75574295 | 127 | WNT11 | 7481 |
| rs17749202 | 36 | 11 | 75575022 | 127 | WNT11 | 7481 |
| rs7936750 | 36 | 11 | 75577055 | 127 | WNT11 | 7481 |
| rs10899175 | 36 | 11 | 75577129 | 127 | WNT11 | 7481 |
| rs882151 | 36 | 11 | 75581785 | 127 | WNT11 | 7481 |
| rs3781730 | 36 | 11 | 75585731 | 127 | WNT11 | 7481 |
| rs608747 | 36 | 11 | 75594125 | 127 | WNT11 | 7481 |
| rs1568507 | 36 | 11 | 75596967 | 127 | WNT11 | 7481 |
| rs663907 | 36 | 11 | 75600717 | 127 | WNT11 | 7481 |
| rs689419 | 36 | 11 | 75604615 | 127 | WNT11 | 7481 |
| rs12416814 | 36 | 11 | 75605089 | 127 | WNT11 | 7481 |
| rs525404 | 36 | 11 | 95206168 | 127 | MTMR2 | 8898 |
| rs16922615 | 36 | 11 | 95206706 | 127 | MTMR2 | 8898 |
| rs16922622 | 36 | 11 | 95207036 | 127 | MTMR2 | 8898 |
| rs611020 | 36 | 11 | 95207553 | 127 | MTMR2 | 8898 |
| rs17229128 | 36 | 11 | 95209963 | 127 | MTMR2 | 8898 |
| rs547219 | 36 | 11 | 95213139 | 127 | MTMR2 | 8898 |
| rs568878 | 36 | 11 | 95218342 | 127 | MTMR2 | 8898 |
| rs566204 | 36 | 11 | 95220574 | 127 | MTMR2 | 8898 |
| rs687116 | 36 | 11 | 95251413 | 127 | MTMR2 | 8898 |
| rs4753703 | 36 | 11 | 95270661 | 127 | MTMR2 | 8898 |
| rs7110786 | 36 | 11 | 95296296 | 127 | MTMR2 | 8898 |
| rs17301028 | 36 | 11 | 102485534 | 127 | DYNC2H1 | 79659 |
| rs11225553 | 36 | 11 | 102494416 | 127 | DYNC2H1 | 79659 |
| rs17301182 | 36 | 11 | 102496407 | 127 | DYNC2H1 | 79659 |
| rs11608130 | 36 | 11 | 102498194 | 127 | DYNC2H1 | 79659 |
| rs12577612 | 36 | 11 | 102502197 | 127 | DYNC2H1 | 79659 |
| rs17373533 | 36 | 11 | 102505175 | 127 | DYNC2H1 | 79659 |
| rs11225571 | 36 | 11 | 102526316 | 127 | DYNC2H1 | 79659 |
| rs17301750 | 36 | 11 | 102532444 | 127 | DYNC2H1 | 79659 |
| rs688906 | 36 | 11 | 102534726 | 127 | DYNC2H1 | 79659 |
| rs688244 | 36 | 11 | 102543737 | 127 | DYNC2H1 | 79659 |
| rs585692 | 36 | 11 | 102552217 | 127 | DYNC2H1 | 79659 |
| rs11225584 | 36 | 11 | 102557768 | 127 | DYNC2H1 | 79659 |
| rs17374436 | 36 | 11 | 102561890 | 127 | DYNC2H1 | 79659 |
| rs658804 | 36 | 11 | 102562258 | 127 | DYNC2H1 | 79659 |
| rs11225597 | 36 | 11 | 102571895 | 127 | DYNC2H1 | 79659 |
| rs685395 | 36 | 11 | 102572670 | 127 | DYNC2H1 | 79659 |
| rs17394217 | 36 | 11 | 102587768 | 127 | DYNC2H1 | 79659 |
| rs589623 | 36 | 11 | 102587800 | 127 | DYNC2H1 | 79659 |
| rs683608 | 36 | 11 | 102596197 | 127 | DYNC2H1 | 79659 |
| rs3912622 | 36 | 11 | 102626683 | 127 | DYNC2H1 | 79659 |
| rs11225634 | 36 | 11 | 102629345 | 127 | DYNC2H1 | 79659 |
| rs12574626 | 36 | 11 | 102658129 | 127 | DYNC2H1 | 79659 |

APPENDIX 1-continued

SNPs genotyped

| SNP ID | Genome Build Version | Chr | Position | dbSNP Version | Gene Symbol | Gene ID |
|---|---|---|---|---|---|---|
| rs10895391 | 36 | 11 | 102663488 | 127 | DYNC2H1 | −99 |
| rs7944311 | 36 | 11 | 102672402 | 127 | DYNC2H1 | 79659 |
| rs7945431 | 36 | 11 | 102672619 | 127 | DYNC2H1 | 79659 |
| rs11225665 | 36 | 11 | 102674923 | 127 | DYNC2H1 | 79659 |
| rs1430870 | 36 | 11 | 102678248 | 127 | DYNC2H1 | 79659 |
| rs17396421 | 36 | 11 | 102685655 | 127 | DYNC2H1 | 79659 |
| rs11225710 | 36 | 11 | 102694144 | 127 | DYNC2H1 | 79659 |
| rs313408 | 36 | 11 | 102696540 | 127 | DYNC2H1 | 79659 |
| rs313403 | 36 | 11 | 102697742 | 127 | DYNC2H1 | 79659 |
| rs313425 | 36 | 11 | 102715394 | 127 | DYNC2H1 | 79659 |
| rs11225731 | 36 | 11 | 102716667 | 127 | DYNC2H1 | 79659 |
| rs2566913 | 36 | 11 | 102734237 | 127 | DYNC2H1 | 79659 |
| rs1913462 | 36 | 11 | 102739939 | 127 | DYNC2H1 | 79659 |
| rs17308149 | 36 | 11 | 102803176 | 127 | DYNC2H1 | 79659 |
| rs603517 | 36 | 11 | 102808757 | 127 | DYNC2H1 | 79659 |
| rs590320 | 36 | 11 | 102815994 | 127 | DYNC2H1 | 79659 |
| rs589943 | 36 | 11 | 102816061 | 127 | DYNC2H1 | 79659 |
| rs642495 | 36 | 11 | 102819224 | 127 | DYNC2H1 | 79659 |
| rs7118365 | 36 | 11 | 102823025 | 127 | DYNC2H1 | 79659 |
| rs313874 | 36 | 11 | 102831660 | 127 | DYNC2H1 | 79659 |
| rs11611231 | 36 | 12 | 844587 | 127 | HSN2 | 378465 |
| rs7305099 | 36 | 12 | 845537 | 127 | HSN2 | 378465 |
| rs4980973 | 36 | 12 | 853307 | 127 | HSN2 | 65125 |
| rs1029628 | 36 | 12 | 1598849 | 127 | WNT5B | 81029 |
| rs4765834 | 36 | 12 | 1599896 | 127 | WNT5B | 81029 |
| rs4766399 | 36 | 12 | 1604821 | 127 | WNT5B | 81029 |
| rs10848539 | 36 | 12 | 1613817 | 127 | WNT5B | 81029 |
| rs2240509 | 36 | 12 | 1620858 | 127 | WNT5B | 81029 |
| rs2240511 | 36 | 12 | 1623551 | 127 | WNT5B | 81029 |
| rs7132752 | 36 | 12 | 1623995 | 127 | WNT5B | 81029 |
| rs3803164 | 36 | 12 | 1625915 | 127 | WNT5B | 81029 |
| rs3803163 | 36 | 12 | 1626221 | 127 | WNT5B | 81029 |
| rs12819505 | 36 | 12 | 1626926 | 127 | WNT5B | 81029 |
| rs1003939 | 36 | 12 | 1626939 | 127 | WNT5B | 81029 |
| rs4766402 | 36 | 12 | 1627176 | 127 | WNT5B | 81029 |
| rs2887603 | 36 | 12 | 1628004 | 127 | WNT5B | 81029 |
| rs7133682 | 36 | 12 | 18782054 | 127 | CAPZA3 | 89869 |
| rs11831038 | 36 | 12 | 18786722 | 127 | CAPZA3 | 93661 |
| rs11052030 | 36 | 12 | 32542199 | 127 | FGD4 | 121512 |
| rs17536631 | 36 | 12 | 32543516 | 127 | FGD4 | 121512 |
| rs7133863 | 36 | 12 | 32547517 | 127 | FGD4 | 121512 |
| rs1500876 | 36 | 12 | 32550544 | 127 | FGD4 | 121512 |
| rs11052034 | 36 | 12 | 32551017 | 127 | FGD4 | 121512 |
| rs17536908 | 36 | 12 | 32552485 | 127 | FGD4 | 121512 |
| rs7305247 | 36 | 12 | 32556716 | 127 | FGD4 | 121512 |
| rs17609576 | 36 | 12 | 32565912 | 127 | FGD4 | 121512 |
| rs7295095 | 36 | 12 | 32566794 | 127 | FGD4 | 121512 |
| rs16920000 | 36 | 12 | 32575058 | 127 | FGD4 | 121512 |
| rs7315682 | 36 | 12 | 32577224 | 127 | FGD4 | 121512 |
| rs7966521 | 36 | 12 | 32580484 | 127 | FGD4 | 121512 |
| rs7967302 | 36 | 12 | 32580847 | 127 | FGD4 | 121512 |
| rs4931015 | 36 | 12 | 32581981 | 127 | FGD4 | 121512 |
| rs4931016 | 36 | 12 | 32582013 | 127 | FGD4 | 121512 |
| rs11052063 | 36 | 12 | 32592406 | 127 | FGD4 | 121512 |
| rs7298165 | 36 | 12 | 32594007 | 127 | FGD4 | 121512 |
| rs17538095 | 36 | 12 | 32594051 | 127 | FGD4 | 121512 |
| rs1875059 | 36 | 12 | 32594167 | 127 | FGD4 | 121512 |
| rs4635166 | 36 | 12 | 32596175 | 127 | FGD4 | 121512 |
| rs4931637 | 36 | 12 | 32601913 | 127 | FGD4 | 121512 |
| rs10844243 | 36 | 12 | 32604402 | 127 | FGD4 | 121512 |
| rs11052069 | 36 | 12 | 32605186 | 127 | FGD4 | 121512 |
| rs10844246 | 36 | 12 | 32612704 | 127 | FGD4 | 121512 |
| rs17538775 | 36 | 12 | 32623596 | 127 | FGD4 | 121512 |
| rs904582 | 36 | 12 | 32626503 | 127 | FGD4 | 121512 |
| rs9988998 | 36 | 12 | 32639606 | 127 | FGD4 | 121512 |
| rs12823621 | 36 | 12 | 32646526 | 127 | FGD4 | 121512 |
| rs10506097 | 36 | 12 | 32653050 | 127 | FGD4 | 121512 |
| rs999840 | 36 | 12 | 32653759 | 127 | FGD4 | 121512 |
| rs10844253 | 36 | 12 | 32655451 | 127 | FGD4 | 121512 |
| rs11052110 | 36 | 12 | 32668629 | 127 | FGD4 | 121512 |
| rs17539792 | 36 | 12 | 32669156 | 127 | FGD4 | 121512 |
| rs7962152 | 36 | 12 | 32670957 | 127 | FGD4 | 121512 |
| rs4018511 | 36 | 12 | 47641303 | 127 | WNT10B | 377 |
| rs3741627 | 36 | 12 | 47645854 | 127 | WNT10B | 7480 |

APPENDIX 1-continued

SNPs genotyped

| SNP ID | Genome Build Version | Chr | Position | dbSNP Version | Gene Symbol | Gene ID |
|---|---|---|---|---|---|---|
| rs833840 | 36 | 12 | 47652417 | 127 | WNT1; WNT10B | 7480 |
| rs833839 | 36 | 12 | 47653157 | 127 | WNT1; WNT10B | 7480 |
| rs590460 | 36 | 12 | 48736243 | 127 | ACCN2 | 41 |
| rs1108923 | 36 | 12 | 48744363 | 127 | ACCN2 | 41 |
| rs706793 | 36 | 12 | 48754036 | 127 | ACCN2 | 41 |
| rs1043011 | 36 | 12 | 55151307 | 127 | GLS2 | 27165 |
| rs2638315 | 36 | 12 | 55151323 | 127 | GLS2 | 27165 |
| rs2657879 | 36 | 12 | 55151605 | 127 | GLS2 | 27165 |
| rs6581096 | 36 | 12 | 55164387 | 127 | GLS2 | 27165 |
| rs12824907 | 36 | 12 | 56228373 | 127 | DCTN2; KIF5A | 10540 |
| rs2620678 | 36 | 12 | 56249211 | 127 | KIF5A | 3798 |
| rs11172254 | 36 | 12 | 56255005 | 127 | KIF5A | 3798 |
| rs2888334 | 36 | 12 | 56262914 | 127 | KIF5A | 3798 |
| rs775250 | 36 | 12 | 56263307 | 127 | KIF5A | 3798 |
| rs1678536 | 36 | 12 | 56265457 | 127 | KIF5A | 3798 |
| rs8873 | 36 | 12 | 56266216 | 127 | KIF5A | 3798 |
| rs1545783 | 36 | 12 | 56268521 | 127 | KIF5A | 79837 |
| rs1861810 | 36 | 12 | 108709305 | 127 | TRPV4 | 59341 |
| rs3742037 | 36 | 12 | 108710762 | 127 | TRPV4 | 59341 |
| rs10735104 | 36 | 12 | 108712348 | 127 | TRPV4 | 59341 |
| rs12578919 | 36 | 12 | 108717674 | 127 | TRPV4 | 59341 |
| rs3825396 | 36 | 12 | 108719081 | 127 | TRPV4 | 59341 |
| rs3825394 | 36 | 12 | 108725221 | 127 | TRPV4 | 59341 |
| rs10850838 | 36 | 12 | 108763195 | 127 | TRPV4 | 59341 |
| rs6606743 | 36 | 12 | 108763562 | 127 | TRPV4 | 59341 |
| rs7138273 | 36 | 12 | 118107127 | 127 | HSPB8 | 26353 |
| rs2278182 | 36 | 12 | 118108718 | 127 | HSPB8 | 26353 |
| rs11038 | 36 | 12 | 118116690 | 127 | HSPB8 | 26353 |
| rs1133026 | 36 | 12 | 118116730 | 127 | HSPB8 | 26353 |
| rs10774488 | 36 | 12 | 118118995 | 127 | HSPB8 | 643737 |
| rs3916065 | 36 | 12 | 119419007 | 127 | DNCL1 | 8655 |
| rs1169288 | 36 | 12 | 119901033 | 127 | TCF1 | 6927 |
| rs1169286 | 36 | 12 | 119903439 | 127 | TCF1 | 6927 |
| rs2245407 | 36 | 12 | 119908381 | 127 | TCF1 | 6927 |
| rs12427353 | 36 | 12 | 119911284 | 127 | TCF1 | 6927 |
| rs2071190 | 36 | 12 | 119915655 | 127 | TCF1 | 6927 |
| rs1169302 | 36 | 12 | 119916685 | 127 | TCF1 | 6927 |
| rs2464196 | 36 | 12 | 119919810 | 127 | TCF1 | 6927 |
| rs2464195 | 36 | 12 | 119919858 | 127 | TCF1 | 6927 |
| rs2259816 | 36 | 12 | 119919970 | 127 | TCF1 | 6927 |
| rs3999413 | 36 | 12 | 119922321 | 127 | TCF1 | 6927 |
| rs1169310 | 36 | 12 | 119923816 | 127 | TCF1 | 6927 |
| rs2313477 | 36 | 13 | 19656323 | 127 | GJB2 | 2706 |
| rs3751385 | 36 | 13 | 19660956 | 127 | GJB2 | 2706 |
| rs4769974 | 36 | 13 | 19663831 | 127 | GJB2 | 2706 |
| rs1932429 | 36 | 13 | 19669715 | 127 | GJB2 | 2706 |
| rs7984806 | 36 | 13 | 19670687 | 127 | GJB2 | 2706 |
| rs9552104 | 36 | 13 | 19673997 | 127 | GJB2 | 2706 |
| rs12889177 | 36 | 14 | 22561169 | 127 | PSMB5 | 5693 |
| rs10138759 | 36 | 14 | 22562116 | 127 | PSMB5 | 5693 |
| rs17125731 | 36 | 14 | 22564074 | 127 | PSMB5 | 5693 |
| rs941717 | 36 | 14 | 22564827 | 127 | PSMB5 | 5693 |
| rs941718 | 36 | 14 | 22564888 | 127 | PSMB5 | 5693 |
| rs11543947 | 36 | 14 | 22573861 | 127 | PSMB5 | 5693 |
| rs4981456 | 36 | 14 | 22581197 | 127 | PSMB5 | 122706 |
| rs1390376 | 36 | 14 | 51848225 | 127 | PTGER2 | 5732 |
| rs17197 | 36 | 14 | 51864131 | 127 | PTGER2 | 5732 |
| rs17125362 | 36 | 14 | 51866579 | 127 | PTGER2 | 5732 |
| rs781697 | 36 | 14 | 51868016 | 127 | PTGER2 | 5732 |
| rs17831718 | 36 | 14 | 51869786 | 127 | PTGER2 | 5732 |
| rs10483639 | 36 | 14 | 54376207 | 127 | GCH1 | 2643 |
| rs7142517 | 36 | 14 | 54376554 | 127 | GCH1 | 2643 |
| rs841 | 36 | 14 | 54380242 | 127 | GCH1 | 2643 |
| rs17253591 | 36 | 14 | 54385166 | 127 | GCH1 | 2643 |
| rs8007201 | 36 | 14 | 54394598 | 127 | GCH1 | 2643 |
| rs17128050 | 36 | 14 | 54413629 | 127 | GCH1 | 2643 |
| rs998259 | 36 | 14 | 54424781 | 127 | GCH1 | 2643 |
| rs3783641 | 36 | 14 | 54429889 | 127 | GCH1 | 2643 |
| rs3783642 | 36 | 14 | 54429953 | 127 | GCH1 | 2643 |
| rs8007267 | 36 | 14 | 54448741 | 127 | GCH1 | 2643 |
| rs3818188 | 36 | 14 | 101515914 | 127 | DYNC1H1 | 1778 |
| rs4906172 | 36 | 14 | 101524686 | 127 | DYNC1H1 | 1778 |
| rs10132469 | 36 | 14 | 101526144 | 127 | DYNC1H1 | 1778 |
| rs8006586 | 36 | 14 | 101549929 | 127 | DYNC1H1 | 1778 |

APPENDIX 1-continued

SNPs genotyped

| SNP ID | Genome Build Version | Chr | Position | dbSNP Version | Gene Symbol | Gene ID |
|---|---|---|---|---|---|---|
| rs10129889 | 36 | 14 | 101577809 | 127 | DYNC1H1 | 1778 |
| rs1190606 | 36 | 14 | 101580181 | 127 | DYNC1H1 | 1778 |
| rs13749 | 36 | 14 | 101583980 | 127 | DYNC1H1 | 1778 |
| rs2494738 | 36 | 14 | 104317731 | 127 | AKT1 | 207 |
| rs2494743 | 36 | 14 | 104322765 | 127 | AKT1 | 207 |
| rs1130214 | 36 | 14 | 104330779 | 127 | AKT1 | 207 |
| rs1133154 | 36 | 15 | 32309849 | 127 | SLC12A6 | 51234 |
| rs4530104 | 36 | 15 | 32309971 | 127 | SLC12A6 | 51234 |
| rs6495639 | 36 | 15 | 32311528 | 127 | SLC12A6 | 9990 |
| rs4779660 | 36 | 15 | 32312287 | 127 | SLC12A6 | 9990 |
| rs4780233 | 36 | 15 | 32312327 | 127 | SLC12A6 | 9990 |
| rs16958873 | 36 | 15 | 32312880 | 127 | SLC12A6 | 9990 |
| rs4577050 | 36 | 15 | 32316240 | 127 | SLC12A6 | 9990 |
| rs17236791 | 36 | 15 | 32329898 | 127 | SLC12A6 | 9990 |
| rs17236798 | 36 | 15 | 32330164 | 127 | SLC12A6 | 9990 |
| rs2290940 | 36 | 15 | 32331760 | 127 | SLC12A6 | 9990 |
| rs2705343 | 36 | 15 | 32333213 | 127 | SLC12A6 | 9990 |
| rs2615358 | 36 | 15 | 32333743 | 127 | SLC12A6 | 9990 |
| rs7164902 | 36 | 15 | 32338374 | 127 | SLC12A6 | 9990 |
| rs7165973 | 36 | 15 | 32363058 | 127 | SLC12A6 | 9990 |
| rs347866 | 36 | 15 | 32397271 | 127 | SLC12A6 | 9990 |
| rs347867 | 36 | 15 | 32398256 | 127 | SLC12A6 | 9990 |
| rs8028600 | 36 | 15 | 32400009 | 127 | SLC12A6 | 9990 |
| rs17236840 | 36 | 15 | 32400051 | 127 | SLC12A6 | 9990 |
| rs17236847 | 36 | 15 | 32404605 | 127 | SLC12A6 | 9990 |
| rs11638692 | 36 | 15 | 32404636 | 127 | SLC12A6 | 9990 |
| rs652196 | 36 | 15 | 38163439 | 127 | BMF | 90427 |
| rs12913170 | 36 | 15 | 38163500 | 127 | BMF | 90427 |
| rs998713 | 36 | 15 | 38165759 | 127 | BMF | 90427 |
| rs546220 | 36 | 15 | 38166552 | 127 | BMF | 90427 |
| rs648289 | 36 | 15 | 38168225 | 127 | BMF | 90427 |
| rs10518679 | 36 | 15 | 38169733 | 127 | BMF | 90427 |
| rs3743129 | 36 | 15 | 38171071 | 127 | BMF | 90427 |
| rs16970349 | 36 | 15 | 38171424 | 127 | BMF | 90427 |
| rs588739 | 36 | 15 | 38172380 | 127 | BMF | 90427 |
| rs11637681 | 36 | 15 | 38175263 | 127 | BMF | 90427 |
| rs569539 | 36 | 15 | 38177086 | 127 | BMF | 90427 |
| rs11630670 | 36 | 15 | 38198132 | 127 | BMF | 90427 |
| rs1672466 | 36 | 15 | 39923280 | 127 | SPTBN5 | 8681 |
| rs1197669 | 36 | 15 | 39925748 | 127 | SPTBN5 | 8681 |
| rs1197668 | 36 | 15 | 39927706 | 127 | SPTBN5 | 51332 |
| rs1197660 | 36 | 15 | 39933228 | 127 | SPTBN5 | 51332 |
| rs2305655 | 36 | 15 | 39934931 | 127 | SPTBN5 | 51332 |
| rs2278966 | 36 | 15 | 39943104 | 127 | SPTBN5 | 51332 |
| rs3816534 | 36 | 15 | 39946402 | 127 | SPTBN5 | 51332 |
| rs4923918 | 36 | 15 | 39948235 | 127 | SPTBN5 | 51332 |
| rs12593397 | 36 | 15 | 39953792 | 127 | SPTBN5 | 51332 |
| rs2290559 | 36 | 15 | 39955692 | 127 | SPTBN5 | 51332 |
| rs747779 | 36 | 15 | 39957870 | 127 | SPTBN5 | 51332 |
| rs1197691 | 36 | 15 | 39962396 | 127 | SPTBN5 | 51332 |
| rs2280016 | 36 | 15 | 39965414 | 127 | SPTBN5 | 51332 |
| rs1124850 | 36 | 15 | 39967823 | 127 | SPTBN5 | 51332 |
| rs1618332 | 36 | 15 | 39972086 | 127 | SPTBN5 | 51332 |
| rs1197701 | 36 | 15 | 39974784 | 127 | SPTBN5 | 51332 |
| rs1672460 | 36 | 15 | 39975327 | 127 | SPTBN5 | 51332 |
| rs1672461 | 36 | 15 | 39977488 | 127 | SPTBN5 | 30844 |
| rs11636443 | 36 | 15 | 50106988 | 127 | MAPK6 | 5597 |
| rs8034167 | 36 | 15 | 50127514 | 127 | MAPK6 | 5597 |
| rs10851507 | 36 | 15 | 50137961 | 127 | MAPK6 | 5597 |
| rs11070879 | 36 | 15 | 50138955 | 127 | MAPK6 | 5597 |
| rs17612368 | 36 | 15 | 50149195 | 127 | MAPK6 | 5597 |
| rs1138465 | 36 | 15 | 87659606 | 127 | POLG | 55215 |
| rs3087374 | 36 | 15 | 87660998 | 127 | POLG | 5428 |
| rs3176208 | 36 | 15 | 87665767 | 127 | POLG | 5428 |
| rs2074885 | 36 | 15 | 87670670 | 127 | POLG | 5428 |
| rs2351000 | 36 | 15 | 87670737 | 127 | POLG | 5428 |
| rs7495044 | 36 | 15 | 87685173 | 127 | POLG | 5428 |
| rs393521 | 36 | 16 | 277679 | 127 | AXIN1 | 8312 |
| rs214247 | 36 | 16 | 289222 | 127 | AXIN1 | 8312 |
| rs214246 | 36 | 16 | 289294 | 127 | AXIN1 | 8312 |
| rs7200589 | 36 | 16 | 289332 | 127 | AXIN1 | 8312 |
| rs1204042 | 36 | 16 | 292737 | 127 | AXIN1 | 8312 |
| rs3842950 | 36 | 16 | 300318 | 127 | AXIN1 | 8312 |
| rs7359414 | 36 | 16 | 302639 | 127 | AXIN1 | 8312 |

APPENDIX 1-continued

SNPs genotyped

| SNP ID | Genome Build Version | Chr | Position | dbSNP Version | Gene Symbol | Gene ID |
|---|---|---|---|---|---|---|
| rs426884 | 36 | 16 | 315199 | 127 | AXIN1 | 8312 |
| rs11648673 | 36 | 16 | 317795 | 127 | AXIN1 | 8312 |
| rs12719801 | 36 | 16 | 321142 | 127 | AXIN1 | 8312 |
| rs12445857 | 36 | 16 | 326424 | 127 | AXIN1 | −99 |
| rs370681 | 36 | 16 | 332462 | 127 | AXIN1 | 8312 |
| rs395901 | 36 | 16 | 333343 | 127 | AXIN1 | 8312 |
| rs2885415 | 36 | 16 | 335397 | 127 | AXIN1 | 8312 |
| rs1805105 | 36 | 16 | 336265 | 127 | AXIN1 | 8312 |
| rs758033 | 36 | 16 | 337045 | 127 | AXIN1 | 8312 |
| rs17136255 | 36 | 16 | 340476 | 127 | AXIN1 | 8312 |
| rs9888749 | 36 | 16 | 348373 | 127 | AXIN1 | 8312 |
| rs7102 | 36 | 16 | 11549743 | 127 | LITAF | 9516 |
| rs9935945 | 36 | 16 | 11551132 | 127 | LITAF | 9516 |
| rs11644920 | 36 | 16 | 11552514 | 127 | LITAF | 9516 |
| rs8048403 | 36 | 16 | 11553776 | 127 | LITAF | 9516 |
| rs4280262 | 36 | 16 | 11554993 | 127 | LITAF | 9516 |
| rs11642799 | 36 | 16 | 11555637 | 127 | LITAF | 9516 |
| rs7403964 | 36 | 16 | 11557558 | 127 | LITAF | 9516 |
| rs3743582 | 36 | 16 | 11557826 | 127 | LITAF | 9516 |
| rs9937485 | 36 | 16 | 11560281 | 127 | LITAF | 9516 |
| rs8048521 | 36 | 16 | 11568203 | 127 | LITAF | 9516 |
| rs6498224 | 36 | 16 | 11576044 | 127 | LITAF | 9516 |
| rs12930096 | 36 | 16 | 11578259 | 127 | LITAF | 9516 |
| rs12444633 | 36 | 16 | 11585358 | 127 | LITAF | 9516 |
| rs1345442 | 36 | 16 | 11587031 | 127 | LITAF | 9516 |
| rs1345441 | 36 | 16 | 11587324 | 127 | LITAF | 9516 |
| rs11864737 | 36 | 16 | 30037613 | 127 | MAPK3 | 5595 |
| rs9921806 | 36 | 16 | 30040261 | 127 | MAPK3 | 5595 |
| rs11862377 | 36 | 16 | 65315471 | 127 | DYNC1LI2 | 1783 |
| rs12599882 | 36 | 16 | 65320348 | 127 | DYNC1LI2 | 1783 |
| rs2067040 | 36 | 16 | 65322310 | 127 | DYNC1LI2 | 1783 |
| rs363180 | 36 | 16 | 65350405 | 127 | DYNC1LI2 | 283847 |
| rs14178 | 36 | 16 | 66527032 | 127 | PSMB10 | 5699 |
| rs20549 | 36 | 16 | 66527431 | 127 | PSMB10 | 5699 |
| rs4986970 | 36 | 16 | 66533821 | 127 | PSMB10 | 3931 |
| rs9928594 | 36 | 16 | 79127742 | 127 | DYNLRB2 | 83657 |
| rs13338237 | 36 | 16 | 79128602 | 127 | DYNLRB2 | 83657 |
| rs10781994 | 36 | 16 | 79133210 | 127 | DYNLRB2 | 83657 |
| rs9937217 | 36 | 16 | 79140368 | 127 | DYNLRB2 | 83657 |
| rs12934612 | 36 | 16 | 79140777 | 127 | DYNLRB2 | −99 |
| rs11866734 | 36 | 16 | 79140998 | 127 | DYNLRB2 | 83657 |
| rs3212346 | 36 | 16 | 88509859 | 127 | MC1R | 4157 |
| rs3212363 | 36 | 16 | 88512942 | 127 | MC1R | 4157 |
| rs4790522 | 36 | 17 | 3416603 | 127 | TRPV1 | 7442 |
| rs16953163 | 36 | 17 | 3417989 | 127 | TRPV1 | 7442 |
| rs224546 | 36 | 17 | 3419621 | 127 | TRPV1 | 7442 |
| rs3826503 | 36 | 17 | 3421410 | 127 | TRPV1 | 7442 |
| rs877610 | 36 | 17 | 3422240 | 127 | TRPV1 | 7442 |
| rs877611 | 36 | 17 | 3422315 | 127 | TRPV1 | 7442 |
| rs17706245 | 36 | 17 | 3423740 | 127 | TRPV1 | 7442 |
| rs161364 | 36 | 17 | 3424561 | 127 | TRPV1 | 7442 |
| rs8065080 | 36 | 17 | 3427196 | 127 | TRPV1 | 7442 |
| rs17633288 | 36 | 17 | 3430534 | 127 | TRPV1 | 7442 |
| rs150908 | 36 | 17 | 3431117 | 127 | TRPV1 | 7442 |
| rs224534 | 36 | 17 | 3433451 | 127 | TRPV1 | 7442 |
| rs222747 | 36 | 17 | 3439949 | 127 | TRPV1 | 7442 |
| rs222748 | 36 | 17 | 3441110 | 127 | TRPV1 | 7442 |
| rs150846 | 36 | 17 | 3441617 | 127 | TRPV1 | 7442 |
| rs222749 | 36 | 17 | 3442123 | 127 | TRPV1 | 7442 |
| rs161385 | 36 | 17 | 3442975 | 127 | TRPV1 | 7442 |
| rs2277675 | 36 | 17 | 3447259 | 127 | TRPV1 | 7442 |
| rs12944357 | 36 | 17 | 3453368 | 127 | TRPV1 | 23729 |
| rs222741 | 36 | 17 | 3455629 | 127 | TRPV1 | 23729 |
| rs17634022 | 36 | 17 | 3455907 | 127 | TRPV1 | 23729 |
| rs224495 | 36 | 17 | 3459876 | 127 | TRPV1 | 23729 |
| rs224498 | 36 | 17 | 3466703 | 127 | TRPV1 | 23729 |
| rs2241933 | 36 | 17 | 4646905 | 127 | PSMB6 | 5694 |
| rs11654690 | 36 | 17 | 4651636 | 127 | PSMB6 | 5694 |
| rs2074222 | 36 | 17 | 7070698 | 127 | DVL2 | 1856 |
| rs222837 | 36 | 17 | 7073280 | 127 | DVL2 | 1856 |
| rs222836 | 36 | 17 | 7073886 | 127 | DVL2 | 1856 |
| rs2074216 | 36 | 17 | 7074333 | 127 | DVL2 | 1856 |
| rs17710 | 36 | 17 | 7084718 | 127 | DVL2 | 11337 |
| rs222843 | 36 | 17 | 7086705 | 127 | DVL2 | 11337 |

APPENDIX 1-continued

SNPs genotyped

| SNP ID | Genome Build Version | Chr | Position | dbSNP Version | Gene Symbol | Gene ID |
|---|---|---|---|---|---|---|
| rs230938 | 36 | 17 | 15071845 | 127 | PMP22 | 5376 |
| rs1993614 | 36 | 17 | 15072070 | 127 | PMP22 | 5376 |
| rs7538 | 36 | 17 | 15074382 | 127 | PMP22 | 5376 |
| rs13422 | 36 | 17 | 15074900 | 127 | PMP22 | 5376 |
| rs230945 | 36 | 17 | 15078058 | 127 | PMP22 | 5376 |
| rs17773165 | 36 | 17 | 15082587 | 127 | PMP22 | 5376 |
| rs3744333 | 36 | 17 | 15083480 | 127 | PMP22 | 5376 |
| rs17773227 | 36 | 17 | 15090503 | 127 | PMP22 | 5376 |
| rs230911 | 36 | 17 | 15093903 | 127 | PMP22 | 5376 |
| rs16951263 | 36 | 17 | 15101897 | 127 | PMP22 | 5376 |
| rs2072325 | 36 | 17 | 15102702 | 127 | PMP22 | 5376 |
| rs231020 | 36 | 17 | 15103114 | 127 | PMP22 | 5376 |
| rs179521 | 36 | 17 | 15113946 | 127 | PMP22 | 5376 |
| rs8065610 | 36 | 17 | 15116295 | 127 | PMP22 | 5376 |
| rs2048230 | 36 | 17 | 19216792 | 127 | MAPK7 | 5598 |
| rs2233072 | 36 | 17 | 19222421 | 127 | MAPK7 | 5598 |
| rs228271 | 36 | 17 | 34160006 | 127 | PSMB3 | 7703 |
| rs228273 | 36 | 17 | 34161649 | 127 | PSMB3 | 5691 |
| rs16968005 | 36 | 17 | 34161883 | 127 | PSMB3 | 5691 |
| rs228274 | 36 | 17 | 34162587 | 127 | PSMB3 | 5691 |
| rs228275 | 36 | 17 | 34164351 | 127 | PSMB3 | 5691 |
| rs65926 | 36 | 17 | 34169959 | 127 | PSMB3 | 5691 |
| rs764190 | 36 | 17 | 34170125 | 127 | PSMB3 | 5691 |
| rs1043515 | 36 | 17 | 34175722 | 127 | PSMB3 | 8396 |
| rs3744070 | 36 | 17 | 34177865 | 127 | PSMB3 | 8396 |
| rs7213337 | 36 | 17 | 37132954 | 127 | HAP1 | 9001 |
| rs4523977 | 36 | 17 | 37136876 | 127 | HAP1 | 9001 |
| rs11867808 | 36 | 17 | 37137198 | 127 | HAP1 | 9001 |
| rs4796691 | 36 | 17 | 37137315 | 127 | HAP1 | 9001 |
| rs7224601 | 36 | 17 | 37148507 | 127 | HAP1 | 9001 |
| rs199505 | 36 | 17 | 42214571 | 127 | WNT3 | 7473 |
| rs916888 | 36 | 17 | 42218292 | 127 | WNT3 | 7473 |
| rs199500 | 36 | 17 | 42218572 | 127 | WNT3 | 7473 |
| rs2074405 | 36 | 17 | 42221161 | 127 | WNT3 | 7473 |
| rs199497 | 36 | 17 | 42221762 | 127 | WNT3 | 7473 |
| rs199496 | 36 | 17 | 42221887 | 127 | WNT3 | 7473 |
| rs11658976 | 36 | 17 | 42221965 | 127 | WNT3 | 7473 |
| rs11655598 | 36 | 17 | 42223260 | 127 | WNT3 | 7473 |
| rs12452064 | 36 | 17 | 42223353 | 127 | WNT3 | 7473 |
| rs199494 | 36 | 17 | 42224229 | 127 | WNT3 | 7473 |
| rs10514911 | 36 | 17 | 42233432 | 127 | WNT3 | 7473 |
| rs7207916 | 36 | 17 | 42234514 | 127 | WNT3 | 7473 |
| rs11653738 | 36 | 17 | 42242117 | 127 | WNT3 | 7473 |
| rs3933652 | 36 | 17 | 42243714 | 127 | WNT3 | 7473 |
| rs3933653 | 36 | 17 | 42243741 | 127 | WNT3 | 7473 |
| rs3916033 | 36 | 17 | 42244702 | 127 | WNT3 | 7473 |
| rs3851781 | 36 | 17 | 42246300 | 127 | WNT3 | 7473 |
| rs7220040 | 36 | 17 | 42280547 | 127 | WNT9B | 7484 |
| rs12602434 | 36 | 17 | 42283052 | 127 | WNT9B | 7484 |
| rs12150651 | 36 | 17 | 42288568 | 127 | WNT9B | 7484 |
| rs2165846 | 36 | 17 | 42296365 | 127 | WNT9B | 7484 |
| rs12952746 | 36 | 17 | 42298412 | 127 | WNT9B | 7484 |
| rs6504591 | 36 | 17 | 42299827 | 127 | WNT9B | 7484 |
| rs11079740 | 36 | 17 | 42304099 | 127 | WNT9B | 7484 |
| rs4968281 | 36 | 17 | 42305121 | 127 | WNT9B | 7484 |
| rs1530364 | 36 | 17 | 42306776 | 127 | WNT9B | 7484 |
| rs8065435 | 36 | 17 | 53512616 | 127 | DYNLL2 | 729460 |
| rs8069790 | 36 | 17 | 53513244 | 127 | DYNLL2 | 729460 |
| rs11079337 | 36 | 17 | 53517495 | 127 | DYNLL2 | 729460 |
| rs9900038 | 36 | 17 | 53524762 | 127 | DYNLL2 | 140735 |
| rs2333091 | 36 | 17 | 53525967 | 127 | DYNLL2 | 140735 |
| rs4293 | 36 | 17 | 58909398 | 127 | ACE | 1636 |
| rs4309 | 36 | 17 | 58913655 | 127 | ACE | 1636 |
| rs4311 | 36 | 17 | 58914495 | 127 | ACE | 1636 |
| rs4343 | 36 | 17 | 58919763 | 127 | ACE | 1636 |
| rs4362 | 36 | 17 | 58927493 | 127 | ACE | 1636 |
| rs4461142 | 36 | 17 | 58931780 | 127 | ACE | 1636 |
| rs4459610 | 36 | 17 | 58938452 | 127 | ACE | 1636 |
| rs8066276 | 36 | 17 | 58942997 | 127 | ACE | 1636 |
| rs4611524 | 36 | 17 | 58945384 | 127 | ACE | 1636 |
| rs12451328 | 36 | 17 | 58950280 | 127 | ACE | 1636 |
| rs6504234 | 36 | 17 | 59918318 | 127 | POLG2 | 11232 |
| rs1427463 | 36 | 17 | 59923044 | 127 | POLG2 | 11232 |
| rs9897606 | 36 | 17 | 59923629 | 127 | POLG2 | 11232 |

APPENDIX 1-continued

SNPs genotyped

| SNP ID | Genome Build Version | Chr | Position | dbSNP Version | Gene Symbol | Gene ID |
|---|---|---|---|---|---|---|
| rs10512502 | 36 | 17 | 59925471 | 127 | POLG2 | 1655 |
| rs1140409 | 36 | 17 | 59927132 | 127 | POLG2 | 1655 |
| rs16947824 | 36 | 17 | 59931967 | 127 | POLG2 | 1655 |
| rs1991401 | 36 | 17 | 59932897 | 127 | POLG2 | 1655 |
| rs2004887 | 36 | 17 | 77090696 | 127 | ACTG1 | 71 |
| rs7342974 | 36 | 17 | 77098594 | 127 | ACTG1 | 71 |
| rs875120 | 36 | 18 | 27421062 | 127 | TTR | 7276 |
| rs3764478 | 36 | 18 | 27424481 | 127 | TTR | 7276 |
| rs1800458 | 36 | 18 | 27426863 | 127 | TTR | 7276 |
| rs4444423 | 36 | 18 | 46338134 | 127 | MAPK4 | 5596 |
| rs11082830 | 36 | 18 | 46345270 | 127 | MAPK4 | 5596 |
| rs3853680 | 36 | 18 | 46350202 | 127 | MAPK4 | 5596 |
| rs8089517 | 36 | 18 | 46350750 | 127 | MAPK4 | 5596 |
| rs11665303 | 36 | 18 | 46357790 | 127 | MAPK4 | 5596 |
| rs753328 | 36 | 18 | 46362006 | 127 | MAPK4 | 5596 |
| rs11082832 | 36 | 18 | 46369429 | 127 | MAPK4 | 5596 |
| rs4939989 | 36 | 18 | 46369453 | 127 | MAPK4 | 5596 |
| rs11660097 | 36 | 18 | 46395615 | 127 | MAPK4 | 5596 |
| rs1561261 | 36 | 18 | 46395655 | 127 | MAPK4 | 5596 |
| rs11664092 | 36 | 18 | 46396472 | 127 | MAPK4 | 5596 |
| rs3867257 | 36 | 18 | 46400046 | 127 | MAPK4 | 5596 |
| rs4939992 | 36 | 18 | 46406082 | 127 | MAPK4 | 5596 |
| rs7227542 | 36 | 18 | 46406920 | 127 | MAPK4 | 5596 |
| rs9960447 | 36 | 18 | 46408176 | 127 | MAPK4 | 5596 |
| rs11875289 | 36 | 18 | 46414032 | 127 | MAPK4 | 5596 |
| rs2118370 | 36 | 18 | 46415542 | 127 | MAPK4 | 5596 |
| rs8091136 | 36 | 18 | 46417885 | 127 | MAPK4 | 5596 |
| rs17804574 | 36 | 18 | 46419749 | 127 | MAPK4 | 5596 |
| rs3894010 | 36 | 18 | 46421235 | 127 | MAPK4 | 5596 |
| rs3867260 | 36 | 18 | 46422257 | 127 | MAPK4 | 5596 |
| rs893320 | 36 | 18 | 46424976 | 127 | MAPK4 | 5596 |
| rs4939998 | 36 | 18 | 46425665 | 127 | MAPK4 | 5596 |
| rs4939999 | 36 | 18 | 46427395 | 127 | MAPK4 | 5596 |
| rs9953685 | 36 | 18 | 46435944 | 127 | MAPK4 | 5596 |
| rs3752085 | 36 | 18 | 46444269 | 127 | MAPK4 | 5596 |
| rs3752087 | 36 | 18 | 46444438 | 127 | MAPK4 | 5596 |
| rs12607365 | 36 | 18 | 46447672 | 127 | MAPK4 | 5596 |
| rs9956244 | 36 | 18 | 46449556 | 127 | MAPK4 | 5596 |
| rs1893489 | 36 | 18 | 46449659 | 127 | MAPK4 | 5596 |
| rs1893490 | 36 | 18 | 46449799 | 127 | MAPK4 | 5596 |
| rs12961853 | 36 | 18 | 46466397 | 127 | MAPK4 | 5596 |
| rs1545129 | 36 | 18 | 46474330 | 127 | MAPK4 | 5596 |
| rs17742551 | 36 | 18 | 46474454 | 127 | MAPK4 | 5596 |
| rs17662824 | 36 | 18 | 46475799 | 127 | MAPK4 | −99 |
| rs8096108 | 36 | 18 | 46476874 | 127 | MAPK4 | 5596 |
| rs894768 | 36 | 18 | 46477656 | 127 | MAPK4 | 5596 |
| rs4260159 | 36 | 18 | 46483873 | 127 | MAPK4 | 5596 |
| rs6508027 | 36 | 18 | 46484275 | 127 | MAPK4 | 5596 |
| rs7227230 | 36 | 18 | 46484894 | 127 | MAPK4 | 5596 |
| rs9948424 | 36 | 18 | 46487076 | 127 | MAPK4 | 5596 |
| rs4939642 | 36 | 18 | 46488427 | 127 | MAPK4 | 5596 |
| rs11665501 | 36 | 18 | 46489084 | 127 | MAPK4 | 5596 |
| rs11665570 | 36 | 18 | 46489323 | 127 | MAPK4 | 5596 |
| rs12959952 | 36 | 18 | 46494835 | 127 | MAPK4 | 5596 |
| rs7240429 | 36 | 18 | 46497316 | 127 | MAPK4 | 5596 |
| rs4940005 | 36 | 18 | 46497589 | 127 | MAPK4 | 5596 |
| rs17662967 | 36 | 18 | 46500216 | 127 | MAPK4 | 5596 |
| rs3794900 | 36 | 18 | 46500325 | 127 | MAPK4 | 5596 |
| rs1807382 | 36 | 18 | 46508173 | 127 | MAPK4 | 5596 |
| rs7242442 | 36 | 18 | 46515455 | 127 | MAPK4 | 5596 |
| rs9635955 | 36 | 18 | 46517113 | 127 | MAPK4 | 5596 |
| rs1261084 | 36 | 18 | 51041158 | 127 | TCF4 | 6925 |
| rs1261070 | 36 | 18 | 51054083 | 127 | TCF4 | 6925 |
| rs10515969 | 36 | 18 | 51054812 | 127 | TCF4 | 6925 |
| rs1942265 | 36 | 18 | 51066565 | 127 | TCF4 | 6925 |
| rs1261134 | 36 | 18 | 51082761 | 127 | TCF4 | 6925 |
| rs1261115 | 36 | 18 | 51091526 | 127 | TCF4 | 6925 |
| rs3794894 | 36 | 18 | 51119198 | 127 | TCF4 | 6925 |
| rs1440475 | 36 | 18 | 51130347 | 127 | TCF4 | 6925 |
| rs10515970 | 36 | 18 | 51131633 | 127 | TCF4 | 6925 |
| rs11659559 | 36 | 18 | 51156932 | 127 | TCF4 | 6925 |
| rs1660242 | 36 | 18 | 51189674 | 127 | TCF4 | 6925 |
| rs1788025 | 36 | 18 | 51199676 | 127 | TCF4 | 6925 |
| rs9958125 | 36 | 18 | 51204583 | 127 | TCF4 | 6925 |

APPENDIX 1-continued

SNPs genotyped

| SNP ID | Genome Build Version | Chr | Position | dbSNP Version | Gene Symbol | Gene ID |
|---|---|---|---|---|---|---|
| rs11152363 | 36 | 18 | 51208186 | 127 | TCF4 | 6925 |
| rs2119292 | 36 | 18 | 51233972 | 127 | TCF4 | 6925 |
| rs2919451 | 36 | 18 | 51235298 | 127 | TCF4 | 6925 |
| rs12963463 | 36 | 18 | 51250091 | 127 | TCF4 | 6925 |
| rs7231748 | 36 | 18 | 51260033 | 127 | TCF4 | 6925 |
| rs1452789 | 36 | 18 | 51266877 | 127 | TCF4 | 6925 |
| rs2924321 | 36 | 18 | 51276433 | 127 | TCF4 | 6925 |
| rs2924329 | 36 | 18 | 51286892 | 127 | TCF4 | 6925 |
| rs17596267 | 36 | 18 | 51292535 | 127 | TCF4 | 6925 |
| rs7233312 | 36 | 18 | 51294571 | 127 | TCF4 | 6925 |
| rs2958183 | 36 | 18 | 51301074 | 127 | TCF4 | 6925 |
| rs9960767 | 36 | 18 | 51306000 | 127 | TCF4 | 6925 |
| rs2924333 | 36 | 18 | 51307227 | 127 | TCF4 | 6925 |
| rs4801157 | 36 | 18 | 51315691 | 127 | TCF4 | 6925 |
| rs2958188 | 36 | 18 | 51316957 | 127 | TCF4 | 6925 |
| rs3017183 | 36 | 18 | 51319241 | 127 | TCF4 | 6925 |
| rs17512480 | 36 | 18 | 51324171 | 127 | TCF4 | 6925 |
| rs2924338 | 36 | 18 | 51326785 | 127 | TCF4 | 6925 |
| rs12956276 | 36 | 18 | 51326964 | 127 | TCF4 | 6925 |
| rs17597288 | 36 | 18 | 51328206 | 127 | TCF4 | 6925 |
| rs9964328 | 36 | 18 | 51328772 | 127 | TCF4 | 6925 |
| rs12606243 | 36 | 18 | 51335784 | 127 | TCF4 | 6925 |
| rs627685 | 36 | 18 | 51337090 | 127 | TCF4 | 6925 |
| rs4572488 | 36 | 18 | 51349604 | 127 | TCF4 | 6925 |
| rs9636107 | 36 | 18 | 51351115 | 127 | TCF4 | 6925 |
| rs1452787 | 36 | 18 | 51358205 | 127 | TCF4 | 6925 |
| rs17089887 | 36 | 18 | 51359254 | 127 | TCF4 | 6925 |
| rs613872 | 36 | 18 | 51361300 | 127 | TCF4 | 6925 |
| rs658977 | 36 | 18 | 51364885 | 127 | TCF4 | 6925 |
| rs13381608 | 36 | 18 | 51410144 | 127 | TCF4 | 6925 |
| rs590076 | 36 | 18 | 51411730 | 127 | TCF4 | 6925 |
| rs11672431 | 36 | 19 | 10684940 | 127 | DNM2 | 81890 |
| rs892086 | 36 | 19 | 10698677 | 127 | DNM2 | 1785 |
| rs11670097 | 36 | 19 | 10738127 | 127 | DNM2 | 1785 |
| rs2043332 | 36 | 19 | 10752239 | 127 | DNM2 | 1785 |
| rs4296360 | 36 | 19 | 10755240 | 127 | DNM2 | 1785 |
| rs11666111 | 36 | 19 | 10761633 | 127 | DNM2 | 1785 |
| rs7254425 | 36 | 19 | 10763389 | 127 | DNM2 | 1785 |
| rs1610095 | 36 | 19 | 10765689 | 127 | DNM2 | 1785 |
| rs2278444 | 36 | 19 | 10765700 | 127 | DNM2 | 1785 |
| rs2287029 | 36 | 19 | 10777684 | 127 | DNM2 | 1785 |
| rs2419233 | 36 | 19 | 13184759 | 127 | CACNA1A | 773 |
| rs4926143 | 36 | 19 | 13186733 | 127 | CACNA1A | 773 |
| rs1865033 | 36 | 19 | 13193467 | 127 | CACNA1A | 773 |
| rs3816027 | 36 | 19 | 13196432 | 127 | CACNA1A | 773 |
| rs3765012 | 36 | 19 | 13206657 | 127 | CACNA1A | 773 |
| rs10421681 | 36 | 19 | 13210110 | 127 | CACNA1A | 773 |
| rs4926240 | 36 | 19 | 13212594 | 127 | CACNA1A | 773 |
| rs12462609 | 36 | 19 | 13213965 | 127 | CACNA1A | 773 |
| rs12052059 | 36 | 19 | 13216068 | 127 | CACNA1A | 773 |
| rs12611029 | 36 | 19 | 13216633 | 127 | CACNA1A | 773 |
| rs12611099 | 36 | 19 | 13219672 | 127 | CACNA1A | 773 |
| rs8112821 | 36 | 19 | 13222618 | 127 | CACNA1A | 773 |
| rs8103699 | 36 | 19 | 13225012 | 127 | CACNA1A | 773 |
| rs4926242 | 36 | 19 | 13229031 | 127 | CACNA1A | 773 |
| rs2074880 | 36 | 19 | 13233631 | 127 | CACNA1A | 773 |
| rs16031 | 36 | 19 | 13234477 | 127 | CACNA1A | 773 |
| rs7249323 | 36 | 19 | 13238865 | 127 | CACNA1A | 773 |
| rs11085840 | 36 | 19 | 13241883 | 127 | CACNA1A | 773 |
| rs12973989 | 36 | 19 | 13242001 | 127 | CACNA1A | 773 |
| rs7251409 | 36 | 19 | 13242991 | 127 | CACNA1A | 773 |
| rs4926248 | 36 | 19 | 13244313 | 127 | CACNA1A | 773 |
| rs4926250 | 36 | 19 | 13244718 | 127 | CACNA1A | 773 |
| rs16030 | 36 | 19 | 13248904 | 127 | CACNA1A | 773 |
| rs10424916 | 36 | 19 | 13253865 | 127 | CACNA1A | 773 |
| rs4926261 | 36 | 19 | 13268095 | 127 | CACNA1A | 773 |
| rs16018 | 36 | 19 | 13272482 | 127 | CACNA1A | 773 |
| rs16016 | 36 | 19 | 13275594 | 127 | CACNA1A | 773 |
| rs8182538 | 36 | 19 | 13277170 | 127 | CACNA1A | 773 |
| rs11878230 | 36 | 19 | 13278011 | 127 | CACNA1A | 773 |
| rs16015 | 36 | 19 | 13279707 | 127 | CACNA1A | 773 |
| rs2292033 | 36 | 19 | 13288544 | 127 | CACNA1A | 773 |
| rs2419248 | 36 | 19 | 13292486 | 127 | CACNA1A | 773 |
| rs10421428 | 36 | 19 | 13294348 | 127 | CACNA1A | 773 |

APPENDIX 1-continued

SNPs genotyped

| SNP ID | Genome Build Version | Chr | Position | dbSNP Version | Gene Symbol | Gene ID |
|---|---|---|---|---|---|---|
| rs11085843 | 36 | 19 | 13302371 | 127 | CACNA1A | 773 |
| rs10407711 | 36 | 19 | 13303779 | 127 | CACNA1A | 773 |
| rs2248069 | 36 | 19 | 13306208 | 127 | CACNA1A | 773 |
| rs10424440 | 36 | 19 | 13317368 | 127 | CACNA1A | 773 |
| rs4926155 | 36 | 19 | 13321244 | 127 | CACNA1A | 773 |
| rs1742 | 36 | 19 | 13322447 | 127 | CACNA1A | 773 |
| rs4926278 | 36 | 19 | 13326001 | 127 | CACNA1A | 773 |
| rs12985786 | 36 | 19 | 13328036 | 127 | CACNA1A | 773 |
| rs16007 | 36 | 19 | 13331316 | 127 | CACNA1A | 773 |
| rs10419009 | 36 | 19 | 13335397 | 127 | CACNA1A | 773 |
| rs4926281 | 36 | 19 | 13342892 | 127 | CACNA1A | 773 |
| rs11670018 | 36 | 19 | 13344914 | 127 | CACNA1A | 773 |
| rs2900918 | 36 | 19 | 13366333 | 127 | CACNA1A | 773 |
| rs8109003 | 36 | 19 | 13379462 | 127 | CACNA1A | 773 |
| rs8113506 | 36 | 19 | 13380929 | 127 | CACNA1A | 773 |
| rs4926285 | 36 | 19 | 13392611 | 127 | CACNA1A | 773 |
| rs1019472 | 36 | 19 | 13394483 | 127 | CACNA1A | 773 |
| rs752079 | 36 | 19 | 13395127 | 127 | CACNA1A | 773 |
| rs4926286 | 36 | 19 | 13395236 | 127 | CACNA1A | 773 |
| rs4926287 | 36 | 19 | 13398717 | 127 | CACNA1A | 773 |
| rs1422259 | 36 | 19 | 13400602 | 127 | CACNA1A | 773 |
| rs8109635 | 36 | 19 | 13413673 | 127 | CACNA1A | 773 |
| rs1363346 | 36 | 19 | 13416209 | 127 | CACNA1A | 773 |
| rs12609229 | 36 | 19 | 13417718 | 127 | CACNA1A | 773 |
| rs7254385 | 36 | 19 | 13417728 | 127 | CACNA1A | 773 |
| rs933649 | 36 | 19 | 13418907 | 127 | CACNA1A | 773 |
| rs11882861 | 36 | 19 | 13423225 | 127 | CACNA1A | 773 |
| rs4926289 | 36 | 19 | 13431005 | 127 | CACNA1A | 773 |
| rs10422148 | 36 | 19 | 13432311 | 127 | CACNA1A | 773 |
| rs1363345 | 36 | 19 | 13435131 | 127 | CACNA1A | 773 |
| rs4926290 | 36 | 19 | 13437174 | 127 | CACNA1A | 773 |
| rs17777900 | 36 | 19 | 13443311 | 127 | CACNA1A | 773 |
| rs12985705 | 36 | 19 | 13443682 | 127 | CACNA1A | 773 |
| rs8113488 | 36 | 19 | 13444694 | 127 | CACNA1A | 773 |
| rs8104676 | 36 | 19 | 13446915 | 127 | CACNA1A | 773 |
| rs10411263 | 36 | 19 | 13448926 | 127 | CACNA1A | 773 |
| rs12609735 | 36 | 19 | 13449516 | 127 | CACNA1A | 773 |
| rs2112461 | 36 | 19 | 13451331 | 127 | CACNA1A | 773 |
| rs2112460 | 36 | 19 | 13451412 | 127 | CACNA1A | 773 |
| rs10412211 | 36 | 19 | 13452542 | 127 | CACNA1A | 773 |
| rs1862259 | 36 | 19 | 13452949 | 127 | CACNA1A | 773 |
| rs10409870 | 36 | 19 | 13455537 | 127 | CACNA1A | 773 |
| rs1120559 | 36 | 19 | 13460576 | 127 | CACNA1A | 773 |
| rs10409910 | 36 | 19 | 13463461 | 127 | CACNA1A | 773 |
| rs7250452 | 36 | 19 | 13464731 | 127 | CACNA1A | 773 |
| rs5021327 | 36 | 19 | 13471112 | 127 | CACNA1A | 773 |
| rs2419724 | 36 | 19 | 13483767 | 127 | CACNA1A | 773 |
| rs1961721 | 36 | 19 | 13484761 | 127 | CACNA1A | 773 |
| rs10416904 | 36 | 19 | 14439813 | 127 | PTGER1 | 5585 |
| rs1042728 | 36 | 19 | 14442063 | 127 | PTGER1 | 5585 |
| rs2287699 | 36 | 19 | 14451612 | 127 | PTGER1 | 10755 |
| rs2241357 | 36 | 19 | 14451919 | 127 | PTGER1 | 10755 |
| rs3730051 | 36 | 19 | 45436537 | 127 | AKT2 | 208 |
| rs7247515 | 36 | 19 | 45447755 | 127 | AKT2 | 208 |
| rs12460555 | 36 | 19 | 45464304 | 127 | AKT2 | 208 |
| rs16974157 | 36 | 19 | 45464764 | 127 | AKT2 | 208 |
| rs1991823 | 36 | 19 | 45472165 | 127 | AKT2 | 208 |
| rs268674 | 36 | 19 | 45592705 | 127 | PRX | 57716 |
| rs3745202 | 36 | 19 | 45592851 | 127 | PRX | 57716 |
| rs268673 | 36 | 19 | 45593336 | 127 | PRX | 57716 |
| rs1981958 | 36 | 19 | 45599248 | 127 | PRX | 57716 |
| rs16974263 | 36 | 19 | 45605379 | 127 | PRX | 57716 |
| rs268666 | 36 | 19 | 45610005 | 127 | PRX | 57716 |
| rs268664 | 36 | 19 | 45612936 | 127 | PRX | 57716 |
| rs4150992 | 36 | 19 | 45620784 | 127 | PRX | 29950 |
| rs2613843 | 36 | 19 | 45661043 | 127 | SPTBN4 | 645 |
| rs4803342 | 36 | 19 | 45674215 | 127 | SPTBN4 | 57731 |
| rs10401458 | 36 | 19 | 45678404 | 127 | SPTBN4 | 57731 |
| rs1993726 | 36 | 19 | 45688331 | 127 | SPTBN4 | 57731 |
| rs7258710 | 36 | 19 | 45689952 | 127 | SPTBN4 | 57731 |
| rs814536 | 36 | 19 | 45695894 | 127 | SPTBN4 | 57731 |
| rs17656487 | 36 | 19 | 45695915 | 127 | SPTBN4 | 57731 |
| rs17656504 | 36 | 19 | 45698266 | 127 | SPTBN4 | 57731 |
| rs814526 | 36 | 19 | 45699889 | 127 | SPTBN4 | 57731 |

APPENDIX 1-continued

SNPs genotyped

| SNP ID | Genome Build Version | Chr | Position | dbSNP Version | Gene Symbol | Gene ID |
|---|---|---|---|---|---|---|
| rs814528 | 36 | 19 | 45706762 | 127 | SPTBN4 | 57731 |
| rs814534 | 36 | 19 | 45711905 | 127 | SPTBN4 | 57731 |
| rs10410907 | 36 | 19 | 45724949 | 127 | SPTBN4 | 57731 |
| rs814501 | 36 | 19 | 45730414 | 127 | SPTBN4 | 57731 |
| rs843777 | 36 | 19 | 45748632 | 127 | SPTBN4 | 57731 |
| rs1165838 | 36 | 19 | 45767830 | 127 | SPTBN4 | 57731 |
| rs2290682 | 36 | 19 | 45775284 | 127 | SPTBN4 | 92799 |
| rs450819 | 36 | 19 | 45777854 | 127 | SPTBN4 | 92799 |
| rs3745233 | 36 | 19 | 47425705 | 127 | GSK3A | 2931 |
| rs2302485 | 36 | 19 | 47432964 | 127 | GSK3A | 2931 |
| rs6087861 | 36 | 20 | 30333587 | 127 | KIF3B | 9371 |
| rs13037236 | 36 | 20 | 30379122 | 127 | KIF3B | 9371 |
| rs1029116 | 36 | 20 | 30382844 | 127 | KIF3B | 9371 |
| rs2151437 | 36 | 20 | 30384608 | 127 | KIF3B | 9371 |
| rs3813921 | 36 | 20 | 30385507 | 127 | KIF3B | 9371 |
| rs14353 | 36 | 20 | 30386059 | 127 | KIF3B | 9371 |
| rs13111 | 36 | 20 | 30386060 | 127 | KIF3B | 9371 |
| rs8116198 | 36 | 20 | 32577862 | 127 | DNCL2A | 83658 |
| rs13044031 | 36 | 20 | 32586696 | 127 | DNCL2A | 83658 |
| rs2281695 | 36 | 20 | 32592825 | 127 | DNCL2A | 83658 |
| rs6088519 | 36 | 20 | 32595852 | 127 | DNCL2A | 84557 |
| rs6088520 | 36 | 20 | 32596025 | 127 | DNCL2A | 84557 |
| rs2424994 | 36 | 20 | 32596578 | 127 | DNCL2A | 84557 |
| rs6090041 | 36 | 20 | 62183120 | 127 | OPRL1 | 4987 |
| rs6090043 | 36 | 20 | 62188374 | 127 | OPRL1 | 198437 |
| rs2229205 | 36 | 20 | 62199875 | 127 | OPRL1 | 4987 |
| rs6089789 | 36 | 20 | 62202436 | 127 | OPRL1 | 4987 |
| rs4646310 | 36 | 22 | 18308806 | 127 | COMT | 10587 |
| rs2020917 | 36 | 22 | 18308884 | 127 | COMT | 10587 |
| rs933271 | 36 | 22 | 18311407 | 127 | COMT | 10587 |
| rs740603 | 36 | 22 | 18325177 | 127 | COMT | 1312 |
| rs4646312 | 36 | 22 | 18328337 | 127 | COMT | 1312 |
| rs4680 | 36 | 22 | 18331271 | 127 | COMT | 1312 |
| rs4646316 | 36 | 22 | 18332132 | 127 | COMT | 1312 |
| rs165774 | 36 | 22 | 18332561 | 127 | COMT | 1312 |
| rs174696 | 36 | 22 | 18333176 | 127 | COMT | 1312 |
| rs9332377 | 36 | 22 | 18335692 | 127 | COMT | 1312 |
| rs165815 | 36 | 22 | 18339473 | 127 | COMT | 421 |
| rs2518823 | 36 | 22 | 18340188 | 127 | COMT | 421 |
| rs2240713 | 36 | 22 | 18341101 | 127 | COMT | 421 |
| rs2276008 | 36 | 22 | 20444036 | 127 | MAPK1 | 5594 |
| rs6928 | 36 | 22 | 20445004 | 127 | MAPK1 | 5594 |
| rs9340 | 36 | 22 | 20445353 | 127 | MAPK1 | 5594 |
| rs3810610 | 36 | 22 | 20445498 | 127 | MAPK1 | 5594 |
| rs13515 | 36 | 22 | 20445886 | 127 | MAPK1 | 5594 |
| rs13943 | 36 | 22 | 20446202 | 127 | MAPK1 | 5594 |
| rs1063311 | 36 | 22 | 20446467 | 127 | MAPK1 | 5594 |
| rs2298432 | 36 | 22 | 20453189 | 127 | MAPK1 | 5594 |
| rs3729910 | 36 | 22 | 20492126 | 127 | MAPK1 | 5594 |
| rs8141815 | 36 | 22 | 20521585 | 127 | MAPK1 | 5594 |
| rs12172554 | 36 | 22 | 20525075 | 127 | MAPK1 | 5594 |
| rs5755694 | 36 | 22 | 20530530 | 127 | MAPK1 | 5594 |
| rs9610470 | 36 | 22 | 20539139 | 127 | MAPK1 | 5594 |
| rs8141793 | 36 | 22 | 23157079 | 127 | ADORA2A | 646023 |
| rs11704811 | 36 | 22 | 23163164 | 127 | ADORA2A | 135 |
| rs4822489 | 36 | 22 | 23163760 | 127 | ADORA2A | 135 |
| rs17004920 | 36 | 22 | 23164564 | 127 | ADORA2A | 135 |
| rs2236624 | 36 | 22 | 23166024 | 127 | ADORA2A | 135 |
| rs1555048 | 36 | 22 | 49030475 | 127 | MAPK12 | 83933 |
| rs1076649 | 36 | 22 | 49039645 | 127 | MAPK11; MAPK12 | 6300 |
| rs2272857 | 36 | 22 | 49041795 | 127 | MAPK11; MAPK12 | 6300 |
| rs2076139 | 36 | 22 | 49046788 | 127 | MAPK11; MAPK12 | 5600 |
| rs2235356 | 36 | 22 | 49052476 | 127 | MAPK11 | 5600 |
| rs6010226 | 36 | 22 | 49056743 | 127 | MAPK11 | 23654 |
| rs131815 | 36 | 22 | 49306474 | 127 | ECGF1 | 29781 |
| rs140524 | 36 | 22 | 49307548 | 127 | ECGF1 | 29781 |
| rs140523 | 36 | 22 | 49309648 | 127 | ECGF1 | 9997 |
| rs140522 | 36 | 22 | 49318132 | 127 | ECGF1 | 440836 |
| rs131794 | 36 | 22 | 49318618 | 127 | ECGF1 | 440836 |
| rs5770871 | 36 | 22 | 49325128 | 127 | ECGF1 | 440836 |
| rs6525485 | 36 | X | 70359570 | 127 | GJB1 | 2705 |
| rs7057082 | 36 | X | 70362347 | 127 | GJB1 | 2705 |
| rs752081 | 36 | X | 70366527 | 127 | GJB1 | 2705 |
| rs521895 | 36 | X | 102923068 | 127 | PLP1 | 5354 |

APPENDIX 1-continued

SNPs genotyped

| SNP ID | Genome Build Version | Chr | Position | dbSNP Version | Gene Symbol | Gene ID |
|---|---|---|---|---|---|---|
| rs17003884 | 36 | X | 102923122 | 127 | PLP1 | 5354 |
| rs2233696 | 36 | X | 102927056 | 127 | PLP1 | 5354 |
| rs2294152 | 36 | X | 102930390 | 127 | PLP1 | 5354 |
| rs7055303 | 36 | X | 106750252 | 127 | PRPS1 | 5631 |
| rs13440633 | 36 | X | 106752682 | 127 | PRPS1 | 5631 |
| rs12116382 | 36 | X | 106754652 | 127 | PRPS1 | 5631 |
| rs5962867 | 36 | X | 106756861 | 127 | PRPS1 | 5631 |
| rs1924215 | 36 | X | 106757459 | 127 | PRPS1 | 5631 |
| rs1924216 | 36 | X | 106757741 | 127 | PRPS1 | 5631 |
| rs10521515 | 36 | X | 106760120 | 127 | PRPS1 | 5631 |
| rs10217967 | 36 | X | 106762523 | 127 | PRPS1 | 5631 |
| rs5962868 | 36 | X | 106765295 | 127 | PRPS1 | 5631 |
| rs7886132 | 36 | X | 106766918 | 127 | PRPS1 | 5631 |
| rs16985261 | 36 | X | 106767665 | 127 | PRPS1 | 5631 |
| rs5962873 | 36 | X | 106784625 | 127 | PRPS1 | 5631 |

MtSNP Genotyped and Imputed

| SNP or Haplogroup | Position (rCRSa) | SNP Type | Call rate | MAF |
|---|---|---|---|---|
| mt10034 | 10034 | Genotyped | 1.000 | 0.034 |
| mt10044 | 10044 | Imputed | 1.000 | 0.000 |
| mt10084 | 10084 | Genotyped | 1.000 | 0.007 |
| mt10238 | 10238 | Imputed | 1.000 | 0.040 |
| mt10398 | 10398 | Imputed | 1.000 | 0.181 |
| mt10463 | 10463 | Imputed | 0.945 | 0.128 |
| mt10550 | 10550 | Imputed | 1.000 | 0.047 |
| mt10876 | 10876 | Imputed | 0.984 | 0.007 |
| mt10915 | 10915 | Genotyped | 1.000 | 0.027 |
| mt11251 | 11251 | Imputed | 0.945 | 0.241 |
| mt11299 | 11299 | Imputed | 1.000 | 0.047 |
| mt11377 | 11377 | Genotyped | 1.000 | 0.007 |
| mt11467 | 11467 | Imputed | 0.992 | 0.228 |
| mt11470 | 11470 | Imputed | 1.000 | 0.013 |
| mt11485 | 11485 | Genotyped | 1.000 | 0.020 |
| mt11674 | 11674 | Genotyped | 1.000 | 0.020 |
| mt11719 | 11719 | Genotyped | 0.997 | 0.470 |
| mt11812 | 11812 | Genotyped | 0.945 | 0.064 |
| mt11840 | 11840 | Imputed | 1.000 | 0.007 |
| mt1189 | 1189 | Genotyped | 1.000 | 0.040 |
| mt11914 | 11914 | Genotyped | 0.934 | 0.065 |
| mt11947 | 11947 | Imputed | 1.000 | 0.020 |
| mt12007 | 12007 | Genotyped | 0.937 | 0.043 |
| mt12239 | 12239 | Imputed | 1.000 | 0.000 |
| mt12308 | 12308 | Imputed | 0.992 | 0.228 |
| mt12372 | 12372 | Genotyped | 0.992 | 0.228 |
| mt12414 | 12414 | Genotyped | 1.000 | 0.020 |
| mt1243 | 1243 | Imputed | 1.000 | 0.020 |
| mt12501 | 12501 | Imputed | 1.000 | 0.054 |
| mt12612 | 12612 | Imputed | 1.000 | 0.081 |
| mt12618 | 12618 | Imputed | 1.000 | 0.013 |
| mt12633 | 12633 | Genotyped | 1.000 | 0.060 |
| mt12669 | 12669 | Imputed | 1.000 | 0.000 |
| mt12705 | 12705 | Genotyped | 1.000 | 0.087 |
| mt13020 | 13020 | Genotyped | 0.984 | 0.007 |
| mt13105 | 13105 | Genotyped | 0.989 | 0.014 |
| mt13368 | 13368 | Imputed | 0.945 | 0.128 |
| mt13617 | 13617 | Imputed | 1.000 | 0.101 |
| mt13708 | 13708 | Genotyped | 1.000 | 0.107 |
| mt13734 | 13734 | Genotyped | 1.000 | 0.007 |
| mt13740 | 13740 | Imputed | 1.000 | 0.007 |
| mt13780 | 13780 | Imputed | 1.000 | 0.040 |
| mt13879 | 13879 | Genotyped | 1.000 | 0.007 |
| mt13934 | 13934 | Genotyped | 1.000 | 0.020 |
| mt13965 | 13965 | Genotyped | 0.997 | 0.007 |
| mt13966 | 13966 | Genotyped | 1.000 | 0.013 |
| mt14022 | 14022 | Imputed | 1.000 | 0.000 |
| mt14167 | 14167 | Imputed | 1.000 | 0.047 |
| mt14182 | 14182 | Genotyped | 1.000 | 0.060 |
| mt14233 | 14233 | Imputed | 0.945 | 0.064 |
| mt14365 | 14365 | Imputed | 1.000 | 0.007 |
| mt1438 | 1438 | Imputed | 1.000 | 0.020 |
| mt14470 | 14470 | Genotyped | 0.997 | 0.020 |
| mt14582 | 14582 | Imputed | 1.000 | 0.007 |
| mt14687 | 14687 | Imputed | 0.997 | 0.007 |
| mt14766 | 14766 | Imputed | 0.997 | 0.470 |
| mt14793 | 14793 | Genotyped | 0.997 | 0.040 |
| mt14798 | 14798 | Genotyped | 1.000 | 0.101 |
| mt14905 | 14905 | Imputed | 0.945 | 0.128 |
| mt15043 | 15043 | Genotyped | 1.000 | 0.060 |
| mt15218 | 15218 | Genotyped | 1.000 | 0.020 |
| mt15257 | 15257 | Genotyped | 1.000 | 0.013 |
| mt15452 | 15452 | Imputed | 0.995 | 0.215 |
| mt15607 | 15607 | Imputed | 0.945 | 0.128 |
| mt15746 | 15746 | Imputed | 1.000 | 0.000 |
| mt15758 | 15758 | Genotyped | 1.000 | 0.013 |
| mt15784 | 15784 | Genotyped | 1.000 | 0.000 |
| mt15833 | 15833 | Genotyped | 1.000 | 0.020 |
| mt15884 | 15884 | Genotyped | 1.000 | 0.013 |
| mt15904 | 15904 | Imputed | 0.997 | 0.060 |
| mt15907 | 15907 | Imputed | 0.984 | 0.007 |
| mt15924 | 15924 | Genotyped | 0.997 | 0.060 |
| mt15928 | 15928 | Imputed | 0.945 | 0.128 |

The invention claimed is:

1. A method of treating a patient with cancer, the method comprising:
    a. performing an assay on the patient's DNA to determine the presence or absence of a biomarker; wherein said biomarker is selected from the group consisting of a homozygous genotype of the minor allele, G, of rs4553808, a homozygous genotype of the minor allele, G, of rs1474642, a homozygous genotype of the minor allele, G, of rs12568757, a homozygous genotype of the minor allele, A, of rs11974610, 1 or 2 copies of the minor allele, G, of rs916758 and 1 or 2 copies of the minor allele, T, of rs1261134; and,
    b. administering bortezomib to the patient lacking said biomarker.

2. The method of claim 1, wherein said biomarker is the homozygous genotype of the minor allele, G, of rs4553808.

3. The method of claim 1, wherein said biomarker is the homozygous genotype of the minor allele, G, of rs1474642.

4. The method of claim 1, wherein said biomarker is the homozygous genotype of the minor allele, G, of rs12568757.

5. The method of claim 1, wherein said biomarker is the homozygous genotype of the minor allele, A, of rs11974610.

6. The method of claim 1, wherein said biomarker is 1 or 2 copies of the minor allele, G, of rs916758.

7. The method of claim 1, wherein said biomarker is 1 or 2 copies of the minor allele, T, of rs1261134.

\* \* \* \* \*